(12) United States Patent
Kawanishi et al.

(10) Patent No.: US 7,647,844 B2
(45) Date of Patent: *Jan. 19, 2010

(54) DEVICE AND METHOD OF DETECTING FLOW RATE/LIQUID KIND, AND DEVICE AND METHOD OF DETECTING LIQUID KIND

(75) Inventors: Toshiaki Kawanishi, Ageo (JP); Takayuki Takahata, Ageo (JP); Kenji Tomonari, Ageo (JP); Kiyoshi Yamagishi, Ageo (JP); Atsushi Koike, Ageo (JP); Akiko Kubota, Ageo (JP); Shin-ichi Inoue, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 17 days.

This patent is subject to a terminal disclaimer.

(21) Appl. No.: 11/956,650

(22) Filed: Dec. 14, 2007

(65) Prior Publication Data
US 2009/0000396 A1 Jan. 1, 2009

Related U.S. Application Data

(63) Continuation-in-part of application No. 10/564,331, filed as application No. PCT/JP2004/009853 on Jul. 9, 2004, now Pat. No. 7,377,185.

(30) Foreign Application Priority Data

Jul. 11, 2003 (JP) ............... 2003-195694
Jul. 24, 2003 (JP) ............... 2003-201142

(51) Int. Cl.
*G01F 1/708* (2006.01)
*G01F 1/68* (2006.01)

(52) U.S. Cl. ............... 73/861.95; 73/202.5; 73/204.15; 73/204.26

(58) Field of Classification Search .............. 73/861.95, 73/202.5
See application file for complete search history.

(56) References Cited

U.S. PATENT DOCUMENTS 3,192,473 A 6/1965 Marsh (Continued)

FOREIGN PATENT DOCUMENTS

EP 1227304 A1 7/2002

(Continued)

*Primary Examiner*—Harshad Patel
(74) *Attorney, Agent, or Firm*—The Webb Law Firm

(57) ABSTRACT

A flow rate/liquid type detecting method for detecting the flow rate of a fluid and, at the same time, detecting any one of or both the type of the fluid and the concentration of the fluid, characterized in that, by using a flow rate/liquid type detecting apparatus comprising: a main passage through which a fluid to be detected flows, an auxiliary passage branched from the main passage, and a flow rate/liquid type detecting sensor device provided in the auxiliary passage, is provided, and in conducting any one of or both the detection of the type of the fluid and the detection of the concentration of the fluid, the auxiliary passage opening/closing valve is closed, and the fluid is allowed to temporarily stay within the flow rate/liquid type detecting sensor device to conduct any one of or both the detection of the liquid type and the detection of the concentration, and in detecting the flow rate of the fluid detected, the auxiliary passage opening/closing valve is opened to allow the fluid to flow into the flow rate/liquid type detecting sensor device to detect the flow rate.

58 Claims, 24 Drawing Sheets

U.S. PATENT DOCUMENTS

| | | |
|---|---|---|
| 3,705,626 A | 12/1972 | Glenn, Jr. et al. |
| 4,961,348 A | 10/1990 | Bonne |
| 5,182,942 A | 2/1993 | Hartel et al. |
| 5,223,783 A | 6/1993 | Wilis |
| 5,452,084 A | 9/1995 | Mitchell et al. |
| 5,622,223 A | 4/1997 | Vasquez |
| 7,058,532 B1 | 6/2006 | Yamagishi et al. |
| 7,152,582 B2 * | 12/2006 | Takahata et al. ....... 123/406.12 |
| 7,168,300 B2 * | 1/2007 | Kawanishi et al. ......... 73/61.46 |
| 7,377,185 B2 * | 5/2008 | Kawanishi et al. ....... 73/861.95 |
| 2003/0106380 A1 | 6/2003 | Bonne et al. |

FOREIGN PATENT DOCUMENTS

| | | |
|---|---|---|
| EP | 1227305 A1 | 7/2002 |

* cited by examiner

DEVICE AND METHOD OF DETECTING FLOW RATE/LIQUID KIND, AND DEVICE AND METHOD OF DETECTING LIQUID KIND

CROSS-REFERENCE TO RELATED APPLICATIONS

This application is a continuation-in-part application of U.S. patent application Ser. No. 10/564,331 filed Jan. 11, 2006, now U.S. Pat. No. 7,377,185 which is the national phase of PCT/JP2004/009853 filed Jul. 9, 2004.

TECHNICAL FIELD

The present invention relates to a flow rate/liquid type detecting apparatus and a flow rate/liquid type detecting method for detecting the type, concentration and flow rate of fluids, for example, gasoline or a light oil as a fuel in automobiles, and organic solutions in plants and the like, and a liquid type detecting apparatus and a liquid type detecting method.

BACKGROUND ART

Automotive exhaust gases contain contaminants such as unburned hydrocarbons (HCs), NOx gases, and SOx gases. An attempt to reduce these contaminants has hitherto been made, for example, by a method in which, for SOx, S in gasoline is removed, or unburned HCs are burned in the presence of a catalyst.

Specifically, as shown in FIG. 17, in an automotive system 100, air is introduced through an automatic element (filter) 102, is then passed through an air flow rate sensor 104, and is fed into an engine 106. On the other hand, a gasoline within a fuel tank 108 is fed through a fuel pump 110 into the engine 106.

Further, the automotive system 100 is constructed so that, based on the results of detection with an A/F sensor 112, fuel injection in the engine 106 is controlled by a fuel injection control device 114 so that the air-fuel ratio is brought to a predetermined theoretical air-fuel ratio.

An exhaust gas from the engine 106 is fed into a catalyst device 116 where hydrocarbons (HCs) contained in the exhaust gas are burned. The exhaust gas is then passed through an oxygen concentration sensor 118 and is discharged as an exhaust gas.

DISCLOSURE OF THE INVENTION

Problems to be Solved by the Invention

In the above automotive system, as shown in FIG. 18, various gasolines different from each other in distillation properties (different from each other in easiness in evaporation) are sold around the world.

Specifically, FIG. 18 shows distillation properties of gasolines, that is, the relationship between % distillate and temperature. For example, 50% (T50) on the abscissa indicates the temperature (° C.) at which 50% of various gasolines are evaporated.

As shown in FIG. 18, for example, as compared with standard gasoline No. 3, gasoline A2 is the heaviest (difficult to evaporate) gasoline, and gasoline No. 7 is the lightest (easy to evaporate) gasoline.

Accordingly, as shown in Table 1 below, for example, in an automobile regulated so that, for standard gasoline No. 3, the air-fuel ratio is a theoretical one, when standard gasoline No. 3 is replaced with the heavier gasoline A2, in particular, the torque is insufficient when an engine is started, particularly when an engine in which a catalyst device is not in a warmed state is started, although the content of HCs in the exhaust gas is low.

On the contrary, when gasoline No. 7 which is a lighter gasoline is used, the air-fuel ratio exceeds the theoretical air-fuel ratio although the torque is satisfactory. In this case, in particular, when an engine is started, particularly when an engine in which a catalyst device is not in a warmed state is started, the content of HCs in the exhaust gas is so large that the influence on the environment is disadvantageously large.

TABLE 1

| Regulation gasoline | Gasoline used | Torque | Exhaust gas (HC) |
|---|---|---|---|
| No. 3 | No. 3 | ○ | ○ |
| No. 3 | A2 | x | ○ |
| No. 3 | No. 7 | ○ | x |

In patent document 1 (Japanese Laid-Open Patent Publication No. Hei 11 (1999)-153561), the present inventors have already proposed a fluid detecting method which comprises energizing a heating element to generate heat, heating a temperature detector with this heat, giving a thermal influence on thermal transfer from the heating element to the temperature detector by the fluid to be detected, and judging the type of the fluid to be detected based on electrical output corresponding to the electrical resistance of the temperature detector. In this method, energization of the heating element is periodically carried out.

In this fluid detection method, however, since the heating element should be periodically energized (using multipulses), a lot of time is required for the detection and, consequently, it is difficult to instantaneously detect the fluid. Further, in this method, for example, fluid detection can be carried out using representative values for substances considerably different from each other in properties, for example, for water, air, and oil. However, for the detection between the above gasolines which have considerably mutually close properties, accurate and rapid detection are difficult.

On the other hand, in consideration of the influence of NOx in an exhaust gas on environment, for example, in order to reduce Nox in the exhaust gas from an automotive fuel such as gasoline or light oils, a method has recently been proposed in which a urea solution is fed into a catalyst device 116 to reduce NOx into $N_2$ gas which is an unharmful gas.

Specifically, as shown in FIG. 19, an automotive system 100 is constructed so that a urea solution is supplied, through a urea solution feed mechanism 130 comprising a urea solution tank 132 storing a urea solution, a urea pump 134, and a urea spray device 136 for spraying a urea solution supplied from the urea pump 134 toward the upstream side of a catalyst device 116, to the upstream side of the catalyst device 116.

In this automotive system, in order to efficiently cause a reduction reaction on the upstream side of the catalyst device 116 without causing solidification of the urea solution, for example, the urea solution preferably comprises 32.5% of urea and 67.5% of $H_2O$.

For this reason, in the prior art technique, an NOx sensor 140 and an NOx sensor 142 are provided respectively on the upstream side and downstream side of the catalyst device 116 to measure the concentration of NOx and thus to judge whether or not the concentration of urea sprayed toward the upstream side of the catalyst device 116 is constant.

However, since, the NOx sensors 140, 142 measure the urea concentration based on the results of a reduction in NOx, it is impossible to previously detect the concentration of urea within the urea solution tank 132 or urea to be sprayed. Further, the sensitivity of the NOx sensors 140, 142 was not so good.

Further, in all the above automotive systems using gasoline and a urea solution, grasping the flow rate and liquid type of gasoline and the flow rate and concentration of the urea solution is important for controlling an engine and a catalyst device to reduce HCs and NOx.

Regarding an apparatus for detecting the flow rate of this fluid, patent document 2 (Japanese Laid-Open Patent Publication No. Hei 11 (1999)-118566) proposes a thermal type flow sensor that uses an indirectly heated flow sensor using a thin-film element and an electric circuit including a bridge circuit for obtaining electrical output corresponding to the flow rate of the fluid, and detects the flow rate of the fluid to be detected by taking advantage of voltage applied to a heating element.

However, in the flow sensor disclosed in patent document 2 (Japanese Laid-Open Patent Publication No. Hei 11 (1999)-118566), although the flow rate of the fluid can be detected, the detection of the liquid type and concentration of the fluid simultaneously with the detection of the flow rate of the fluid is impossible.

Accordingly, in order to grasp the flow rate and type of gasoline and the flow rate and concentration of a urea solution, in addition to the above detecting apparatus for detecting the type of gasoline and apparatus for measuring the concentration of the urea solution, a flow rate measuring apparatus as disclosed in patent document 2 (Japanese Laid-Open Patent Publication No. Hei 11 (1999)-118566) should be separately provided, often leading to an increase in size of the system.

As with the automotive system using the above fluid, systems using kerosene and plants using a solution of a substance dissolved in an organic solvent requires the detection of flow rate and concentration, posing the same problem.

Patent document 1: Japanese Laid-Open Patent Publication No. Hei 11 (1999)-153561 (particularly, see paragraphs [0042] to [0049])

Patent document 2: Japanese Laid-Open Patent Publication No. Hei 11 (1999)-118566

Under these circumstances, an object of the present invention is to provide a flow rate/liquid type detecting apparatus and a flow rate/liquid type detecting method that can detect the flow rate of a fluid and, at the same time, can detect the liquid type and concentration of the fluid in a compact, accurate and rapid manner.

Another object of the present invention is to provide a flow rate/liquid type detecting apparatus for an automobile and a flow rate/liquid type detecting method for an automobile, using the above flow rate/liquid type detecting apparatus and flow rate/liquid type detecting method.

A further object of the present invention is to provide an automotive exhaust gas reducing apparatus and an automotive exhaust gas reducing method, using the above flow rate/liquid type detecting apparatus and flow rate/liquid type detecting method, that can efficiently reduce the exhaust gas and can improve fuel consumption.

Further, under the above circumstances, another object of the present invention is to provide a liquid type detecting apparatus and a liquid type detecting method that can detect the liquid type and concentration of the fluid in a compact, accurate and rapid manner.

Still another object of the present invention is to provide a liquid type detecting apparatus for an automobile and a liquid type detecting method for an automobile, using the above liquid type detecting apparatus and liquid type detecting method.

A further object of the present invention is to provide an automotive exhaust gas reducing apparatus and an automotive exhaust gas reducing method, using the above liquid type detecting apparatus and liquid type detecting method, that can efficiently reduce the exhaust gas and can improve fuel consumption.

SUMMARY OF THE INVENTION

The present invention has been made with a view to solving the above problems of the prior art and to attaining the objects of the present invention, and according to the present invention, there is provided a flow rate/liquid type detecting apparatus for detecting at least one among the flow rate of a fluid, the type of the fluid, and the concentration of the fluid, comprising:

a main passage through which a fluid to be detected flows;

an auxiliary passage branched from said main passage;

a flow rate/liquid type detecting sensor device provided in said auxiliary passage;

an auxiliary passage control mechanism provided in said auxiliary passage, for controlling the flow of the fluid to be detected into said flow rate/liquid type detecting sensor device; and a control unit for controlling said flow rate/liquid detecting sensor device and said auxiliary passage control mechanism, said control unit being constructed so as to conduct control in such a manner that;

in conducting any one of or both the detection of the type of said fluid to be detected and the detection of the concentration of said fluid to be detected, said auxiliary passage control mechanism is closed, and said fluid to be detected is allowed to temporarily stay within said flow rate/liquid type detecting sensor device to conduct any one of or both the detection of the liquid type and the detection of the concentration, and in detecting the flow rate of the fluid to be detected, said auxiliary passage control mechanism is opened to allow the fluid to be detected to flow into said flow rate/liquid detecting sensor device to detect the flow rate, and said flow rate/liquid type detecting sensor device comprises;

a flow rate/liquid type detecting chamber for allowing the fluid to be detected which has been introduced into a flow rate/liquid type detecting sensor device body to temporarily stay therein, a flow rate/liquid type detecting sensor heater provided within said flow rate/liquid type detecting chamber, and said flow rate/liquid type detecting apparatus is constructed so that;

in conducting any one of or both the detection of the type of said fluid to be detected and the detection of the concentration of said fluid to be detected, a pulse voltage is applied to said flow rate/liquid type detecting sensor heater for a predetermined period of time, the fluid to be detected which temporarily stays within said flow rate/liquid type detecting chamber is heated with said flow rate/liquid type detecting sensor heater, and any one of or both the liquid type of the fluid and the concentration of the fluid are detected, by a voltage output difference $V_0$, corresponding to a difference in temperature between the initial temperature and the peak temperature of said flow rate/liquid type detecting liquid temperature sensor, in detecting the flow rate of said fluid to be detected, a pulse voltage is applied to said flow rate/liquid type detecting sensor heater for a predetermined period of time, the fluid to be detected which flows through said flow rate/liquid type detecting chamber is heated with said flow rate/liquid type detecting sensor heater, and the flow rate is detected, by a voltage output difference V0, corresponding to a difference in temperature between the initial temperature and the peak temperature of said flow rate/liquid type detecting sensor heater.

Further, according to the present invention, there is provided a flow rate/liquid type detecting method for detecting at least one among the flow rate of a fluid, the type of the fluid, and the concentration of the fluid, characterized in that:

by using a flow rate/liquid type detecting apparatus comprising;

a main passage through which a fluid to be detected flows;
an auxiliary passage branched from said main passage; and
a flow rate/liquid type detecting sensor device comprises:
a flow rate/liquid type detecting chamber for allowing the fluid to be detected which has been introduced into a flow rate/liquid type detecting sensor device body to temporarily stay therein,
a flow rate/liquid type detecting sensor heater provided within said flow rate/liquid type detecting chamber, and in conducting any one of or both the detection of the type of said fluid to be detected and the detection of the concentration of said fluid to be detected, said auxiliary passage control mechanism is closed, and said fluid to be detected is allowed to temporarily stay within said flow rate/liquid type detecting sensor device, applying a pulse voltage to said flow rate/liquid type detecting sensor heater for a predetermined period of time, heating with the heater, the fluid to be detected which temporarily stays within said flow rate/liquid type detecting chamber, detecting any one of or both the liquid type of the fluid the concentration of the fluid, by a voltage output difference V0, corresponding to a difference in temperature between the initial temperature and the peak temperature of said flow rate/liquid type detecting sensor heater, in detecting the flow rate of the fluid to be detected, said auxiliary passage control mechanism is opened to allow the fluid to be detected to flow into said flow rate/liquid detecting sensor device, applying a pulse voltage to said flow rate/liquid type detecting sensor heater for a predetermined period of time, heating with the heater, the fluid to be detected which temporarily stays within said flow rate/liquid type detecting chamber, detecting any one of or both the liquid type of the fluid the concentration of the fluid, by a voltage output difference V0, corresponding to a difference in temperature between the initial temperature and the peak temperature of said flow rate/liquid type detecting sensor heater.

According to the above construction, in conducting any one of or both the detection of the type of said fluid to be detected and the detection of the concentration of said fluid to be detected, any one of or both the detection of the liquid type and the detection of the concentration can be carried out in an accurate and rapid manner by closing the auxiliary passage control mechanism and allowing the fluid to be detected to temporarily stay within said flow rate/liquid type detecting sensor device.

On the other hand, in detecting the flow rate of the fluid to be detected, the flow rate can be detected by opening the auxiliary passage control mechanism and allowing the fluid to be detected to flow into the flow rate/liquid type detecting sensor device.

Thus, the liquid type and concentration of a fluid can also be detected simultaneously with the detection of the flow rate of the fluid in an accurate and rapid manner. Further, simultaneous detection of the flow rate of the fluid and the detection of the liquid type and concentration of the fluid can be realized in a single flow rate/liquid type detecting apparatus. Therefore, detection in a compact manner can be realized, and, for example, when this is applied to an automotive system, the whole system can be rendered compact.

Further, what is required is only to apply a pulse voltage for a predetermined period of time. Therefore, the type and concentration of a fluid such as gasoline can be detected in an accurate and rapid manner by heating for a short period of time, and, further, without heating the fluid to a temperature at which the fluid ignites.

Specifically, since the above construction utilizes a correlation between the kinematic viscosity of the fluid and the sensor output, utilizes natural convection, and one pulse applied voltage, the type and concentration of the fluid can be detected in an accurate and rapid manner.

The present invention is characterized in that a non-return valve is provided on the downstream side of said flow rate/liquid type detecting sensor device in said auxiliary passage.

As described above, the non-return valve is provided on the downstream side of the flow rate/liquid type detecting sensor device in the auxiliary passage. Therefore, if backward flow is caused, for example, due to the occurrence of pulsating flow depending upon the type of a pump as a liquid feed device for the flow of a fluid, and the type of a drive system, this backward flow can be prevented.

Since the backward flow of the fluid within the flow rate/liquid type detecting sensor device can be prevented, the detection of liquid type, the detection of concentration, and the detection of flow rate can be carried out in an accurate and rapid manner without undergoing the influence of backward flow of the fluid.

The present invention is characterized in that a main passage control mechanism for controlling the flow of said fluid to be detected into said main passage is provided in said main passage.

The flow rate/liquid type detecting apparatus according to the present invention is characterized in that said control unit is constructed so as to conduct control in such a manner that:

when the flow rate of said fluid to be detected is small, said main passage control mechanism is closed, and when the flow rate of said fluid to be detected is large, said main passage control mechanism is opened.

The flow rate/liquid type detecting method according to the present invention is characterized in that control is carried out so that, when the flow rate of said fluid to be detected is small, said main passage control mechanism is closed, and when the flow rate of said fluid to be detected is large, said main passage control mechanism is opened.

When the flow rate of the fluid to be detected is small, closing of the main passage control mechanism allows the fluid to be detected to flow into the auxiliary passage to ensure the flow rate of the fluid necessary for the detection in the flow rate/liquid type detecting sensor device.

On the other hand, when the flow rate of the fluid to be detected is large, opening of the main passage control mechanism allows the fluid to flow into the main passage to lower the flow rate of the fluid which flows into the auxiliary passage and thus to ensure the flow rate of the fluid necessary for the detection in the flow rate/liquid type detecting sensor device.

Accordingly, the present invention can be utilized even when the dynamic range of the flow rate is large, and, thus, it is possible to provide a flow rate/liquid type detecting apparatus and a flow rate/liquid type detecting method with a wide sensitivity range.

Further, the present invention is characterized in that an orifice is provided in the main passage.

Since an orifice is provided in the main passage, even when the pressure loss within the main passage is so small that the fluid is less likely to flow into the auxiliary passage, the pressure loss in the main passage can be increased by the orifice. As a result, the fluid can be allowed to flow at a given flow rate necessary for detection into the auxiliary passage and, thus, the above detection can be reliably carried out.

Further, the present invention is characterized in that the voltage output difference $V0$ is the difference in voltage between an average initial voltage $V1$, which is determined by sampling the initial voltage before the application of said pulse voltage by a predetermined number of times, and an average peak voltage $V2$, which is determined by sampling the peak voltage after the application of said pulse voltage by a predetermined number of times, that is, $$V0=V2-V1.$$

When the above construction is utilized, the voltage output difference $V0$ can be accurately determined based on the average value of a predetermined number of times of sampling for one pulse applied voltage. Therefore, the type, concentration and flow rate of a fluid can be detected in an accurate and rapid manner.

The flow rate/liquid type detecting apparatus according to the present invention is characterized in that said control unit is constructed so that:

based on calibration curve data as a correlation between temperature and voltage output difference, for predetermined reference fluids previously stored in said control unit, any one of or both the liquid type and concentration of said fluid to be detected are detected using said voltage output difference $V0$ obtained for said fluid to be detected.

The flow rate/liquid type detecting method for gasoline according to the present invention is characterized in that:

based on calibration curve data as a correlation between temperature and voltage output difference, for predetermined reference fluids previously stored in said control unit, any one of or both the liquid type and concentration of said fluid to be detected are detected using said voltage output difference $V0$ obtained for said fluid to be detected.

According to the above construction, based on previously stored calibration curve data as a correlation between temperature and voltage output difference, for predetermined reference fluids, the type and concentration of the fluid are detected using the voltage output difference $V0$ obtained for the fluid to be detected. Therefore, the type and concentration of a fluid can be detected in a more accurate and rapid manner.

The flow rate/liquid type detecting apparatus according to the present invention is characterized in that said control unit is constructed so that:

a voltage output Vout for the voltage output difference $V0$ at a measuring temperature for said fluid to be detected is corrected in a correlation with the output voltage for the voltage output difference at the measuring temperature for a predetermined threshold reference fluid.

The flow rate/liquid type detecting method according to the present invention is characterized in that:

a voltage output Vout for the voltage output difference $V0$ at a measuring temperature for said fluid to be detected is corrected in a correlation with the output voltage for the voltage output difference at the measuring temperature for a predetermined threshold reference fluid.

By adopting such a construction, a voltage output Vout for the voltage output difference $V0$ at a measuring temperature for said fluid to be detected is corrected in a correlation with the output voltage for the voltage output difference at the measuring temperature for a predetermined threshold reference fluid. Therefore, the influence of the temperature on the voltage output difference $V0$ can be eliminated to impart a more accurate correlation between the voltage output Vout and the properties of gasoline. As a result, the type, concentration and flow rate of the fluid can be detected in a more accurate and rapid manner.

The flow rate/liquid type detecting apparatus according to the present invention is characterized in that said control unit is constructed so that:

based on calibration curve data as a correlation between temperature and voltage output difference, for predetermined reference fluids previously stored in said control unit, the flow rate of said fluid to be detected is detected using said voltage output difference $V0$ obtained for said fluid to be detected.

The flow rate/liquid type detecting method according to the present invention is characterized in that:

based on previously stored calibration curve data as a correlation between temperature and voltage output difference for predetermined reference fluids, the flow rate of said fluid to be detected is detected using said voltage output difference $V0$ obtained for said fluid to be detected.

According to the above construction, based on previously stored calibration curve data as a correlation between temperature and voltage output difference for predetermined reference fluids, the flow rate of the fluid is detected using said voltage output difference $V0$ obtained for said fluid to be detected, Therefore, the flow rate of a fluid can be detected in a more accurate and rapid manner.

Furthermore, the present invention is characterized in that said flow rate/liquid type detecting sensor heater is constructed so as to come into contact with the fluid to be detected through said metallic fin.

By adopting such a construction, the flow rate/liquid type detecting sensor heater does not come into direct contact with a fluid to be detected. Therefore, malfunction derived from a deterioration with the elapse of time or the presence of foreign matter or the like in the fluid does not occur. Consequently, the type, concentration and flow rate of the fluid can be detected in an accurate and rapid manner.

The flow rate/liquid type detecting apparatus for an automobile according to the present invention is adapted for the detection of the flow rate and type of gasoline or a light oil and is characterized in that:

any of the above flow rate/liquid type detecting apparatuses is provided within a fuel tank or on the upstream side or downstream side of a fuel pump.

The flow rate/liquid type detecting method for an automobile according to the present invention is adapted for detecting the flow rate and type of gasoline or a light oil, comprising:

detecting the flow rate and type of said gasoline or light oil within a fuel tank or on the upstream side or downstream side of a fuel pump, by using any of the above flow rate/liquid type detecting methods.

By adopting such a construction, in automobiles, the type of gasoline or a light oil can be detected in an accurate and rapid manner.

The automotive exhaust gas reduction apparatus according to the present invention is adapted for reducing an exhaust gas from an automobile, comprising:

any of the above flow rate/liquid type detecting apparatuses, which is provided within a fuel tank or on the upstream side or downstream side of a fuel pump; and an ignition timing control unit for regulating ignition timing based on the flow rate and type of the gasoline or light oil, which is detected by said flow rate/liquid type detecting apparatus.

The automotive exhaust gas reduction method according to the present invention is adopted for reducing an exhaust gas from an automobile, comprising the steps of:

detecting the flow rate and type of the gasoline or light oil within a fuel tank or on the upstream side or downstream side of a fuel pump, by using any of the above flow rate/liquid type detecting methods, and regulating an ignition timing based on the flow rate and type of the gasoline or light oil which is detected by said flow rate/liquid type detecting apparatus.

By adopting such a construction, ignition timing can be adjusted based on the results of detection of the flow rate and type of gasoline or a light oil. Therefore, proper ignition timing depending upon the flow rate and type of gasoline or a light oil can be provided.

Accordingly, in particular, even when an engine is started, particularly when an engine in which a catalyst device is not in a warmed state is started, the content of HCs and NOx in the exhaust gas can be reduced, and, at the same time, fuel consumption can be improved, without causing a reduction in torque.

The automotive exhaust gas reduction apparatus according to the present invention is adopted for reducing an exhaust gas from an automobile, comprising:

any of the above flow rate/liquid type detecting apparatuses, which is provided within a fuel tank or on the upstream side or downstream side of a fuel pump; and a gasoline or light oil compression control unit for regulating the compression ratio of the gasoline or light oil based on the flow rate and type of the gasoline or light oil, which is detected by said flow rate/liquid type detecting apparatus.

The automotive exhaust gas reduction method according to the present invention is adopted for reducing an exhaust gas from an automobile, comprising the steps of:

detecting the flow rate and type of the gasoline or light oil within a fuel tank or on the upstream side or downstream side of a fuel pump, by using any of the above flow rate/liquid type detecting methods, and regulating the compression ratio of the gasoline based on the flow rate and type of the gasoline or light oil which is detected by said flow rate/liquid type detecting apparatus.

By adopting such a construction, the compression ratio of gasoline or a light oil can be adjusted based on the results of detection of the flow rate and type of gasoline or a light oil. Therefore, proper compression ratio of gasoline or a light oil depending upon the type of gasoline can be provided.

Accordingly, in particular, even when an engine is started, particularly when an engine in which a catalyst device is not in a warmed state is started, the content of HCs and NOx in the exhaust gas can be reduced, and, at the same time, fuel consumption can be improved, without causing a reduction in torque.

The automotive exhaust gas reduction apparatus according to the present invention is adopted for reducing an exhaust gas from an automobile, comprising:

a urea solution feed mechanism for feeding a urea solution to the upstream side of a catalyst device, said urea solution feed mechanism comprising a urea solution tank for storing a urea solution, a urea pump, a urea spray device for spraying the urea solution, which is supplied from said urea pump, toward the upstream side of said catalyst device, and any of the above flow rate/liquid type detecting apparatuses, which is provided within said urea tank or on the upstream side or downstream side of said urea pump.

The automotive exhaust gas reduction method according to the present invention is adapted for reducing an exhaust gas from an automobile, comprising the steps of:

supplying a urea solution to the upstream side of the catalyst device, through a urea solution feed mechanism comprising a urea solution tank for storing a urea solution, a urea pump, and a urea spray device for spraying the urea solution, which is supplied from said urea pump, toward the upstream side of said catalyst device, and detecting the flow rate and urea concentration of the urea solution within said urea tank or on the upstream side or downstream side of said urea pump, by using any of the above flow rate/liquid type detecting methods.

According to the above construction, in order to efficiently cause a reduction reaction on the upstream side of the catalyst device without causing solidification of the urea solution, whether or not, for example, the urea solution comprises 32.5% of urea and 67.5% of $H_2O$ can be judged in an accurate and rapid manner.

Therefore, the urea concentration of the urea solution in the urea tank can be kept at a predetermined concentration, and, thus, the NOx in the exhaust gas can be decreased to a very low level by reduction.

Further, the present invention has been made with a view to solving the above problems of the prior art and attaining the object of the present invention, and the liquid type detecting apparatus according to the present invention is adapted for detecting any one of or both the liquid type and concentration of a fluid, comprising:

a liquid type detecting chamber for allowing a fluid to be detected which has been introduced into a liquid type detecting apparatus body to temporarily stay therein, a liquid type detecting sensor disposed within said liquid type detecting chamber, and a flow control plate provided within said liquid type detecting chamber so as to surround said liquid type detecting sensor.

said liquid type detecting sensor comprises:

a liquid type detecting sensor heater provided within said liquid type detecting chamber, and in conducting any one of or both the detection of the type of said fluid to be detected and the detection of the concentration of said fluid to be detected, a pulse voltage is applied to said liquid type detecting sensor heater for a predetermined period of time to heat, the fluid to be detected which temporarily stays within said liquid type detecting chamber is heated with aid liquid type detecting sensor heater, and any one of or both the liquid type of the fluid and the concentration of the fluid are detected, by a voltage output difference V0, corresponding to a difference in temperature between the initial temperature and the peak temperature of said liquid type detecting liquid temperature sensor.

Further, the liquid type detecting method according to the present invention is adapted for detecting any one of or both the liquid type and concentration of a fluid, comprising the steps of:

providing a liquid type detecting apparatus comprising;

a liquid type detecting chamber for allowing a fluid to be detected which has been introduced into a liquid type detecting apparatus body to temporarily stay therein, a liquid type detecting sensor disposed within said liquid type detecting chamber, and a flow control plate provided within said liquid type detecting chamber so as to surround said liquid type detecting sensor, and in conducting any one of or both the detection of the type of said fluid to be detected and the detection of the concentration of said fluid to be detected, a pulse voltage is applied to said liquid type detecting sensor heater for a predetermined period of time to heat, the fluid to be detected which temporarily stays within said liquid type detecting chamber is heated with said liquid type detecting sensor heater, and any one of or both the liquid type of the fluid and the concentration of the fluid are detected, by a voltage output difference $V_0$, corresponding to a difference in temperature between the initial temperature and the peak temperature of said liquid type detecting liquid temperature sensor.

According to the above construction, in the case where the introduction of the fluid to be detected into the liquid type detecting apparatus body is stopped to allow the fluid to be detected to temporarily stay within the liquid type detecting chamber, the flow of the fluid to be detected within the liquid type detecting chamber is suppressed by the flow control plate. As a result, the flow of the fluid to be detected around the liquid type detecting sensor, which is located within the flow control plate surrounded by this flow control plate, is instantaneously stopped.

Therefore, in detecting the liquid type and concentration with the liquid type detecting sensor, the flow of the fluid to be detected does not occur, and, further, turbulence of the fluid to be detected by the vibration does not occur. Thus, the influence on the detection of the liquid type and concentration of the fluid to be detected can be prevented. Consequently, the liquid type and concentration of the fluid to be detected can be accurately measured.

Further, since a liquid type detecting chamber is provided, the amount of stay of the fluid to be detected is increased. Therefore, the type and concentration of the fluid to be detected can be accurately detected without undergoing the influence of ambient environment such as external temperature.

Accordingly, when the present invention is applied, for example, to fluids such as automotive gasoline and light oils, upon stop of an automobile, for example, due to waiting for a signal, a fuel pump can be stopped and the liquid type and concentration of the fluid to be detected can be instantaneously detected. In this case, after the completion of the detection, the fuel pump can be started to again start the automobile. Therefore, the detection is not an obstacle to the driving of the automobile.

Further, what is required is only to apply a pulse voltage for a predetermined period of time. Therefore, the type and concentration of a fluid such as gasoline can be detected in an accurate and rapid manner by heating for a short period of time, and, further, without heating the fluid to a temperature at which the fluid ignites.

Specifically, since the above construction utilizes a correlation between the kinematic viscosity of the fluid and the sensor output, utilizes natural convection, and one pulse applied voltage, the type and concentration of the fluid can be detected in an accurate and rapid manner.

Further, the present invention is characterized in that said flow control plate has a fluid inflow port confronted with a fluid introduction port in said liquid type detecting chamber and a fluid outflow port confronted with a fluid discharge port in said liquid type detecting chamber.

According to the above construction, the fluid to be detected is reliably introduced, from the fluid introduction port in the liquid type detecting chamber, into the flow control plate surrounded by the flow control plate, through the fluid inflow port in the flow control plate and reliably enters the circumference of the liquid type detecting sensor located within the fluid control plate. As a result, the liquid type and concentration of the fluid to be detected can be detected with the liquid type detecting sensor.

After the detection of the liquid type and concentration of the fluid to be detected with the liquid type detecting sensor, the fluid after the detection can be reliably discharged from the liquid discharge port in the liquid type detecting chamber through the fluid outflow port in the flow control plate. Therefore, the detection of the fluid to be detected can be successively carried out with good accuracy.

Further, in this detection, air mixed into the fluid to be detected can be reliably discharged from the fluid discharge port in the liquid type detecting chamber through the fluid outflow port in the flow control plate. Therefore, air does not stay around the liquid type detecting sensor, and the influence on the detection can be prevented, contributing to accurate detection.

The present invention is characterized in that the fluid introduction port in said liquid type detecting chamber and the fluid inflow port in said flow control plate are spaced from each other by a predetermined distance, and the fluid discharge port in said liquid type detecting chamber and the fluid outflow port in said flow control plate are spaced from each other by a predetermined distance.

Since the fluid introduction port in the liquid type detecting chamber and the fluid inflow port in the flow control plate are spaced from each other by a predetermined distance, air mixed into the fluid to be detected is moved through the space toward the outside of the flow control plate and is discharged to the outside of the liquid type detecting chamber through the fluid discharge port.

Therefore, the air does not enter the inside of the flow control plate, and, thus, air does not stay around the liquid type detecting sensor. This can realize the prevention of the influence of air on the detection and thus can contribute to accurate detection.

Even though air enters the inside of the flow control plate, this air can be reliably discharged from the fluid discharge port in the liquid type detecting chamber through the fluid outflow port in the flow control plate. Therefore, the air does not stay around the liquid type detecting sensor. This can realize the prevention of the influence of air on the detection and thus can contribute to accurate detection.

Further, the present invention is characterized in that the side wall in the vicinity of the fluid discharge port in said liquid type detecting chamber is provided in an approximately arc form.

Since the side wall in the vicinity of the fluid discharge port in the liquid type detecting chamber is provided in an approximately arc form, air mixed into the fluid to be detected is guided along the approximately arc-shaped side wall in the liquid type detecting chamber to the fluid discharge port in the liquid type detecting chamber and is then discharged.

Therefore, the air does not stay around the fluid discharge port in the liquid type detecting chamber and does not stay around the liquid type detecting sensor. This can realize the prevention of the influence of air on the detection and thus can contribute to accurate detection.

Further, the present invention is characterized in that said liquid type detecting chamber is provided with an approximately circular tube side wall, and the fluid introduction port and the fluid discharge port in said liquid type detecting chamber are provided so as to confront said side wall.

In such a construction, the liquid type detecting chamber has an approximately circular tube-shaped side wall and the fluid introduction port and the fluid discharge port in the liquid type detecting chamber are provided so as to confront the side wall. Therefore, in the vicinity of the fluid introduction port in the liquid type detecting chamber, air which has entered through the fluid introduction port in the liquid type detecting chamber is guided outward along the approximately arc-shaped side wall. Therefore, air does not enter the inside of the flow control plate through the fluid inflow port in the flow control plate.

Further, in the vicinity of the fluid discharge port in the liquid type detection chamber, the air mixed into the fluid to be detected is guided inward along the approximately arc-shaped side wall toward the fluid discharge port. Therefore, the air is guided to the fluid discharge port in the liquid type detecting chamber and is then discharged.

Therefore, the air does not stay around the fluid discharge port in the liquid type detecting chamber and does not stay around the liquid type detecting sensor. This can realize the prevention of the influence of air on the detection and thus can contribute to accurate detection.

Further, the present invention is characterized in that a heat insulating member is interposed between said liquid type detecting apparatus body and said liquid type detecting chamber.

Since a heat insulating member is interposed between said liquid type detecting apparatus body and said liquid type detecting chamber, external temperature, external vibration, and external noise such as external electromagnetic waves do not affect the fluid to be detected within the liquid type detecting chamber and the liquid type detecting sensor. Therefore, the liquid type and concentration of the fluid can be always detected with good accuracy.

For example, when the present invention is applied to the detection of automotive gasoline and light oils, the influence, on the detecting sensor, of the difference in temperature between winter and summer, the difference in temperature derived from direct sunlight, snow and the like, external noise such as electromagnetic waves, and, further, vibration during driving and impact caused, for example, by jumping of stone, can be prevented by this heat insulating member. Therefore, the liquid type and concentration of the fluid can be always detected with good accuracy.

Further, the present invention is characterized in that the voltage output difference $V0$ is the difference in voltage between an average initial voltage $V1$ determined by sampling the initial voltage before the application of said pulse voltage by a predetermined number of times and an average peak voltage $V2$ determined by sampling the peak voltage after the application of said pulse voltage by a predetermined number of times, that is, $$V0 = V2 - V1.$$

By such a construction, the voltage output difference $V0$ can be accurately determined based on the average value of a predetermined number of times of sampling for one pulse applied voltage. Therefore, the type and concentration of a fluid can be detected in an accurate and rapid manner.

Further, the present invention is characterized in that any one of or both the liquid type and concentration of said fluid to be detected are detected using said voltage output difference $V0$ obtained for said fluid to be detected, based on previously stored calibration curve data as a correlation between temperature and voltage output difference for predetermined reference fluids.

According to the above construction, the type and concentration of the fluid are detected using the voltage output difference $V0$ obtained for the fluid to be detected, based on previously stored calibration curve data as a correlation between temperature and voltage output difference for predetermined reference fluids. Therefore, the type and concentration of a fluid can be detected in a more accurate and rapid manner.

Further, the present invention is characterized in that:

a voltage output Vout for the voltage output difference $V0$ at a measuring temperature for said fluid to be detected is corrected in a correlation with the output voltage for the voltage output difference at the measuring temperature for a predetermined threshold reference fluid.

By adopting such a construction, a voltage output Vout for the voltage output difference $V0$ at a measuring temperature for said fluid to be detected is corrected in a correlation with the output voltage for the voltage output difference at the measuring temperature for a predetermined threshold reference fluid. Therefore, the influence of the temperature on the voltage output difference $V0$ can be eliminated to impart a more accurate correlation between the voltage output Vout and the properties of gasoline. As a result, the type and concentration of the fluid can be detected in a more accurate and rapid manner.

Furthermore, the present invention is characterized in that said flow rate/liquid type detecting sensor heater is constructed so as to come into contact with the fluid to be detected through said metallic fin.

By adopting such a construction, the flow rate/liquid type detecting sensor heater does not come into direct contact with a fluid to be detected. Therefore, malfunction derived from a deterioration with the elapse of time or the presence of foreign matter or the like in the fluid does not occur. Consequently, the type and concentration of the fluid can be detected in an accurate and rapid manner.

The liquid type detecting apparatus for an automobile according to the present invention is adapted for the detection of the type of gasoline or a light oil, comprising:

the liquid type detecting apparatuses according to any of claims 1 to 12, which is provided within a fuel tank or on the upstream side or downstream side of a fuel pump.

The liquid type detecting method for an automobile according to the present invention is adapted for detecting the type of gasoline or a light oil, comprising:

detecting the type of said gasoline or light oil within a fuel tank or on the upstream side or downstream side of a fuel pump, by using any of the above liquid type detecting methods.

By adopting such a construction, in automobiles, the type of gasoline or a light oil can be detected in an accurate and rapid manner.

The automotive exhaust gas reduction apparatus according to the present invention is adapted for reducing an exhaust gas from an automobile, comprising:

any of the above liquid type detecting apparatuses, which is provided within a fuel tank or on the upstream side or downstream side of a fuel pump; and an ignition timing control unit for regulating ignition timing based on the type of the gasoline or light oil, which is detected by said liquid type detecting apparatus.

The automotive exhaust gas reduction method according to the present invention is adopted for reducing an exhaust gas from an automobile, comprising the steps of:

detecting the type of the gasoline or light oil within a fuel tank or on the upstream side or downstream side of a fuel pump, by using any of the above liquid type detecting methods, and regulating an ignition timing based on the type of the gasoline or light oil which is detected by said liquid type detecting apparatus.

By adopting such a construction, ignition timing can be adjusted based on the results of detection of the flow rate and the type of gasoline or a light oil. Therefore, proper ignition timing depending upon the type of gasoline or a light oil can be provided.

Accordingly, in particular, even when an engine is started, particularly when an engine in which a catalyst device is not in a warmed state is started, the content of HCs and NOx in the exhaust gas can be reduced, and, at the same time, fuel consumption can be improved, without causing a reduction in torque.

The automotive exhaust gas reduction apparatus according to the present invention is adopted for reducing an exhaust gas from an automobile, comprising:

any of the above liquid type detecting apparatuses, which is provided within a fuel tank or on the upstream side or downstream side of a fuel pump; and a gasoline or light oil compression control unit for regulating the compression ratio of the gasoline or light oil based on the type of the gasoline or light oil which is detected by said liquid type detecting apparatus.

The automotive exhaust gas reduction method according to the present invention is adopted for reducing an exhaust gas from an automobile, comprising the steps of:

detecting the type of the gasoline or light oil within a fuel tank or on the upstream side or downstream side of a fuel pump, by using any of the above liquid type detecting methods, and regulating the compression ratio of the gasoline based on the type of the gasoline or light oil which is detected by said liquid type detecting apparatus.

By adopting such a construction, the compression ratio of gasoline or a light oil can be adjusted based on the results of detection of the type of gasoline or a light oil. Therefore, proper compression ratio of gasoline or a light oil depending upon the type of gasoline can be provided.

Accordingly, in particular, even when an engine is started, particularly when an engine in which a catalyst device is not in a warmed state is started, the content of HCs and NOx in the exhaust gas can be reduced. As a result, and, at the same time, fuel consumption can be improved, without causing a reduction in torque.

The automotive exhaust gas reduction apparatus according to the present invention is adopted for reducing an exhaust gas from an automobile, comprising:

a urea solution feed mechanism for feeding a urea solution to the upstream side of a catalyst device, said urea solution feed mechanism comprising a urea solution tank for storing a urea solution, a urea pump, a urea spray device for spraying the urea solution, which is supplied from said urea pump, toward the upstream side of said catalyst device, and any of the above liquid type detecting apparatuses, which is provided within said urea tank or on the upstream side or downstream side of said urea pump.

The automotive exhaust gas reduction method according to the present invention is adapted for reducing an exhaust gas from an automobile, comprising the steps of:

supplying a urea solution to the upstream side of the catalyst device, through a urea solution feed mechanism comprising a urea solution tank for storing a urea solution, a urea pump, and a urea spray device for spraying the urea solution, which is supplied from said urea pump, toward the upstream side of said catalyst device, and detecting the urea concentration of the urea solution within said urea tank or on the upstream side or downstream side of said urea pump, by using any of the above liquid type detecting methods.

According to the above construction, in order to efficiently cause a reduction reaction on the upstream side of the catalyst device without causing solidification of the urea solution, whether or not, for example, the urea solution comprises 32.5% of urea and 67.5% of $H_2O$ can be judged in an accurate and rapid manner.

Therefore, the urea concentration of the urea solution in the urea tank can be kept at a predetermined concentration, and, thus, the NOx in the exhaust gas can be decreased to a very low level by reduction.

EFFECT OF THE INVENTION

According to the above construction, in conducting any one of or both the detection of the type of said fluid to be detected and the detection of the concentration of said fluid to be detected, any one of or both the detection of the liquid type and the detection of the concentration can be carried out in an accurate and rapid manner by closing the auxiliary passage control mechanism and allowing the fluid to be detected to temporarily stay within said flow rate/liquid type detecting sensor device.

On the other hand, in detecting the flow rate of the fluid to be detected, the flow rate can be detected by opening the auxiliary passage control mechanism and allowing the fluid to be detected to flow into the flow rate/liquid type detecting sensor device.

Thus, the liquid type and concentration of a fluid can also be detected simultaneously with the detection of the flow rate of the fluid in an accurate and rapid manner. Further, simultaneous detection of the flow rate of the fluid and the detection of the liquid type and concentration of the fluid can be realized in a single flow rate/liquid type detecting apparatus. Therefore, detection in a compact manner can be realized, and, for example, when this is applied to an automotive system, the whole system can be rendered compact.

Further, according to the present invention, the non-return valve is provided on the downstream side of the flow rate/liquid type detecting sensor device in the auxiliary passage. Therefore, if backward flow is caused, for example, due to the occurrence of pulsating flow depending upon the type of a pump as a liquid feed device for the flow of a fluid, and the type of a drive system, this backward flow can be prevented.

Since the backward flow of the fluid within the flow rate/liquid type detecting sensor device can be prevented, the detection of liquid type, the detection of concentration, and the detection of flow rate can be carried out in an accurate and rapid manner without undergoing the influence of backward flow of the fluid.

Further, according to the present invention, when the flow rate of the fluid to be detected is small, closing of the main passage control mechanism allows the fluid to be detected to flow into the auxiliary passage to ensure the flow rate of the fluid necessary for the detection in the flow rate/liquid type detecting sensor device.

On the other hand, when the flow rate of the fluid to be detected is large, opening of the main passage control mechanism allows the fluid to flow into the main passage to lower the flow rate of the fluid which flows into the auxiliary passage and thus to ensure the flow rate of the fluid necessary for the detection in the flow rate/liquid type detecting sensor device.

Accordingly, the present invention can be utilized even when the dynamic range of the flow rate is large, and, thus, it is possible to provide a flow rate/liquid type detecting apparatus and a flow rate/liquid type detecting method with a wide sensitivity range.

Further, according to the present invention, since an orifice is provided in the main passage, even when the pressure loss within the main passage is so small that the fluid is less likely to flow into the auxiliary passage, the pressure loss in the main passage can be increased by the orifice. As a result, the fluid can be allowed to flow at a given flow rate necessary for detection into the auxiliary passage and, thus, the above detection can be reliably carried out.

Further, according to the present invention, in the case where the introduction of the fluid to be detected into the liquid type detecting apparatus body is stopped to allow the fluid to be detected to temporarily stay within the liquid type detecting chamber, the flow of the fluid to be detected within the liquid type detecting chamber is suppressed by the flow control plate. As a result, the flow of the fluid to be detected around the liquid type detecting sensor, which is located within the flow control plate surrounded by this flow control plate, is instantaneously stopped.

Therefore, in detecting the liquid type and concentration with the liquid type detecting sensor, the flow of the fluid to be detected does not occur, and, further, turbulence of the fluid to be detected by the vibration does not occur. Thus, the influence on the detection of the liquid type and concentration of the fluid to be detected can be prevented. Consequently, the liquid type and concentration of the fluid to be detected can be accurately measured.

Further, since a liquid type detecting chamber is provided, the amount of stay of the fluid to be detected is increased. Therefore, the type and concentration of the fluid to be detected can be accurately detected without undergoing the influence of ambient environment such as external temperature.

Accordingly, when the present invention is applied, for example, to fluids such as automotive gasoline and light oils, upon stop of an automobile, for example, due to waiting for a signal, a fuel pump can be stopped and the liquid type and concentration of the fluid to be detected can be instantaneously detected. In this case, after the completion of the detection, the fuel pump can be started to again start the automobile. Therefore, the detection is not an obstacle to the driving of the automobile.

Further, according to the present invention, the fluid to be detected is reliably introduced, from the fluid introduction port in the liquid type detecting chamber, into the flow control plate surrounded by the flow control plate, through the fluid inflow port in the flow control plate and reliably enters the circumference of the liquid type detecting sensor located within the fluid control plate. As a result, the liquid type and concentration of the fluid to be detected can be detected with the liquid type detecting sensor.

After the detection of the liquid type and concentration of the fluid to be detected with the liquid type detecting sensor, the fluid after the detection can be reliably discharged from the liquid discharge port in the liquid type detecting chamber through the fluid outflow port in the flow control plate. Therefore, the detection of the fluid to be detected can be successively carried out with good accuracy.

Further, in this detection, air mixed into the fluid to be detected can be reliably discharged from the fluid discharge port in the liquid type detecting chamber through the fluid outflow port in the flow control plate. Therefore, air does not stay around the liquid type detecting sensor, and the influence on the detection can be prevented, contributing to accurate detection.

Further, according to the present invention, since the fluid introduction port in the liquid type detecting chamber and the fluid inflow port in the flow control plate are spaced from each other by a predetermined distance, air mixed into the fluid to be detected is moved through the space toward the outside of the flow control plate and is discharged to the outside of the liquid type detecting chamber through the fluid discharge port.

Therefore, the air does not enter the inside of the flow control plate, and, thus, air does not stay around the liquid type detecting sensor. This can realize the prevention of the influence of air on the detection and thus can contribute to accurate detection.

Even though air enters the inside of the flow control plate, this air can be reliably discharged from the fluid discharge port in the liquid type detecting chamber through the fluid outflow port in the flow control plate. Therefore, the air does not stay around the liquid type detecting sensor. This can realize the prevention of the influence of air on the detection and thus can contribute to accurate detection.

Further, according to the present invention, since the side wall in the vicinity of the fluid discharge port in the liquid type detecting chamber is provided in an approximately arc form, air mixed into the fluid to be detected is guided along the approximately arc-shaped side wall in the liquid type detecting chamber to the fluid discharge port in the liquid type detecting chamber and is then discharged.

Therefore, the air does not stay around the fluid discharge port in the liquid type detecting chamber and does not stay around the liquid type detecting sensor. This can realize the prevention of the influence of air on the detection and thus can contribute to accurate detection.

Further, according to the present invention, the liquid type detecting chamber has an approximately circular tube-shaped side wall and the fluid introduction port and the fluid discharge port in the liquid type detecting chamber are provided so as to confront the side wall. Therefore, in the vicinity of the fluid introduction port in the liquid type detecting chamber, air which has entered through the fluid introduction port in the liquid type detecting chamber is guided outward along the approximately arc-shaped side wall. Therefore, air does not enter the inside of the flow control plate through the fluid inflow port in the flow control plate.

Further, in the vicinity of the fluid discharge port in the liquid type detection chamber, the air mixed into the fluid to be detected is guided inward along the approximately arc-shaped side wall toward the fluid discharge port. Therefore, the air is guided to the fluid discharge port in the liquid type detecting chamber and is then discharged.

Therefore, the air does not stay around the fluid discharge port in the liquid type detecting chamber and does not stay around the liquid type detecting sensor. This can realize the prevention of the influence of air on the detection and thus can contribute to accurate detection.

Further, according to the present invention, since a heat insulating member is interposed between said liquid type detecting apparatus body and said liquid type detecting chamber, external temperature, external vibration, and external noise such as external electromagnetic waves do not affect the fluid to be detected within the liquid type detecting chamber and the liquid type detecting sensor. Therefore, the liquid type and concentration of the fluid can be always detected with good accuracy.

For example, when the present invention is applied to the detection of automotive gasoline and light oils, the influence, on the detecting sensor, of the difference in temperature between winter and summer, the difference in temperature derived from direct sunlight, snow and the like, external noise such as electromagnetic waves, and, further, vibration during driving and impact caused, for example, by jumping of stone, can be prevented by this heat insulating member. Therefore, the liquid type and concentration of the fluid can be always detected with good accuracy.

Further, according to the present invention, what is required is only to apply a pulse voltage for a predetermined period of time. Therefore, the type and concentration of a fluid such as gasoline can be detected in an accurate and rapid manner by heating for a short period of time, and, further, without heating the fluid to a temperature at which the fluid ignites.

Specifically, since the above construction utilizes a correlation between the kinematic viscosity of the fluid and the sensor output, utilizes natural convection, and one pulse applied voltage, the type and concentration of the fluid can be detected in an accurate and rapid manner.

Further, according to the present invention, the voltage output difference V0 can be accurately determined based on the average value of a predetermined number of times of sampling for one pulse applied voltage. Therefore, the type and concentration of a fluid can be detected in an accurate and rapid manner.

Further, according to the present invention, the type and concentration of the fluid are detected using the voltage output difference V0 obtained for the fluid to be detected, based on previously stored calibration curve data as a correlation between temperature and voltage output difference for predetermined reference fluids. Therefore, the type and concentration of a fluid can be detected in a more accurate and rapid manner.

Further, according to the present invention, a voltage output Vout for the voltage output difference V0 at a measuring temperature for said fluid to be detected is corrected in a correlation with the output voltage for the voltage output difference at the measuring temperature for a predetermined threshold reference fluid. Therefore, the influence of the temperature on the voltage output difference V0 can be eliminated to impart a more accurate correlation between the voltage output Vout and the properties of gasoline. As a result, the type and concentration of the fluid can be detected in a more accurate and rapid manner.

Further, according to the present invention, since the flow rate/liquid type detecting sensor heater is a laminated flow rate/liquid type detecting sensor heater in which a heater and a flow rate/liquid type detecting liquid temperature sensor are laminated through an insulating layer, any mechanically moved mechanism part does not exist. Therefore, malfunction derived from a deterioration with the elapse of time or the presence of foreign matter in the fluid or the like does not occur. Consequently, the liquid type, concentration, and flow rate of the fluid can be detected in an accurate and rapid manner.

Furthermore, since the sensor part can be constructed in a very small size, the thermal response is very good and the liquid type and concentration of the fluid can be accurately detected.

Further, according to the present invention, the heater in said liquid type detecting sensor heater and said liquid type detecting liquid temperature sensor each are constructed so as to come into contact with the fluid to be detected through a metallic fin. Therefore, the heater of the liquid type detecting sensor heater and the liquid type detecting liquid temperature sensor do not come into direct contact with a fluid to be detected. Therefore, malfunction derived from a deterioration with the elapse of time or the presence of foreign matter or the like in the fluid does not occur. Consequently, the type and concentration of the fluid can be detected in an accurate and rapid manner.

Further, according to the present invention, the liquid temperature sensor is constructed so as to come into contact with the fluid to be detected through a metallic fin. Therefore, the liquid temperature sensor does not come into direct contact with a fluid to be detected. Therefore, malfunction derived from a deterioration with the elapse of time or the presence of foreign matter or the like in the fluid does not occur. Consequently, the type and concentration of the fluid can be detected in an accurate and rapid manner.

Further, according to the present invention, in automobiles, the flow rate and type of gasoline or a light oil can be detected in an accurate and rapid manner, and, in addition, ignition timing can be adjusted based on the results of the detection of the flow rate and type of the gasoline or light oil. Therefore, proper ignition timing depending upon the flow rate and type of gasoline or a light oil can be realized.

Further, according to the present invention, in automobiles, the flow rate and type of gasoline or a light oil can be detected in an accurate and rapid manner, and, in addition, the compression ratio of the gasoline can be adjusted based on the results of the detection of the flow rate and type of the gasoline or light oil, proper compression ratio of gasoline or a light oil depending upon the flow rate and type of gasoline or a light oil can be realized.

Accordingly, in particular, even when an engine is started, particularly when an engine in which a catalyst device is not in a warmed state is started, the content of HCs and NOx in the exhaust gas can be reduced. As a result, and, at the same time, fuel consumption can be improved, without causing a reduction in torque.

Further, according to the present invention, in order to efficiently cause a reduction reaction on the upstream side of the catalyst device without causing solidification of the urea solution, whether or not, for example, the urea solution comprises 32.5% of urea and 67.5% of $H_2O$ can be judged in an accurate and rapid manner.

Therefore, the urea concentration of the urea solution in the urea tank can be kept at a predetermined concentration, and, thus, the NOx in the exhaust gas can be decreased to a very low level by reduction. Thus, the present invention is an excellent invention which has various significant and inherent function and effect.

DETAILED DESCRIPTION OF THE INVENTION

The mode for carrying out the invention (embodiments) will be described in more detail in conjunction with the accompanying drawings.

Figure 1:
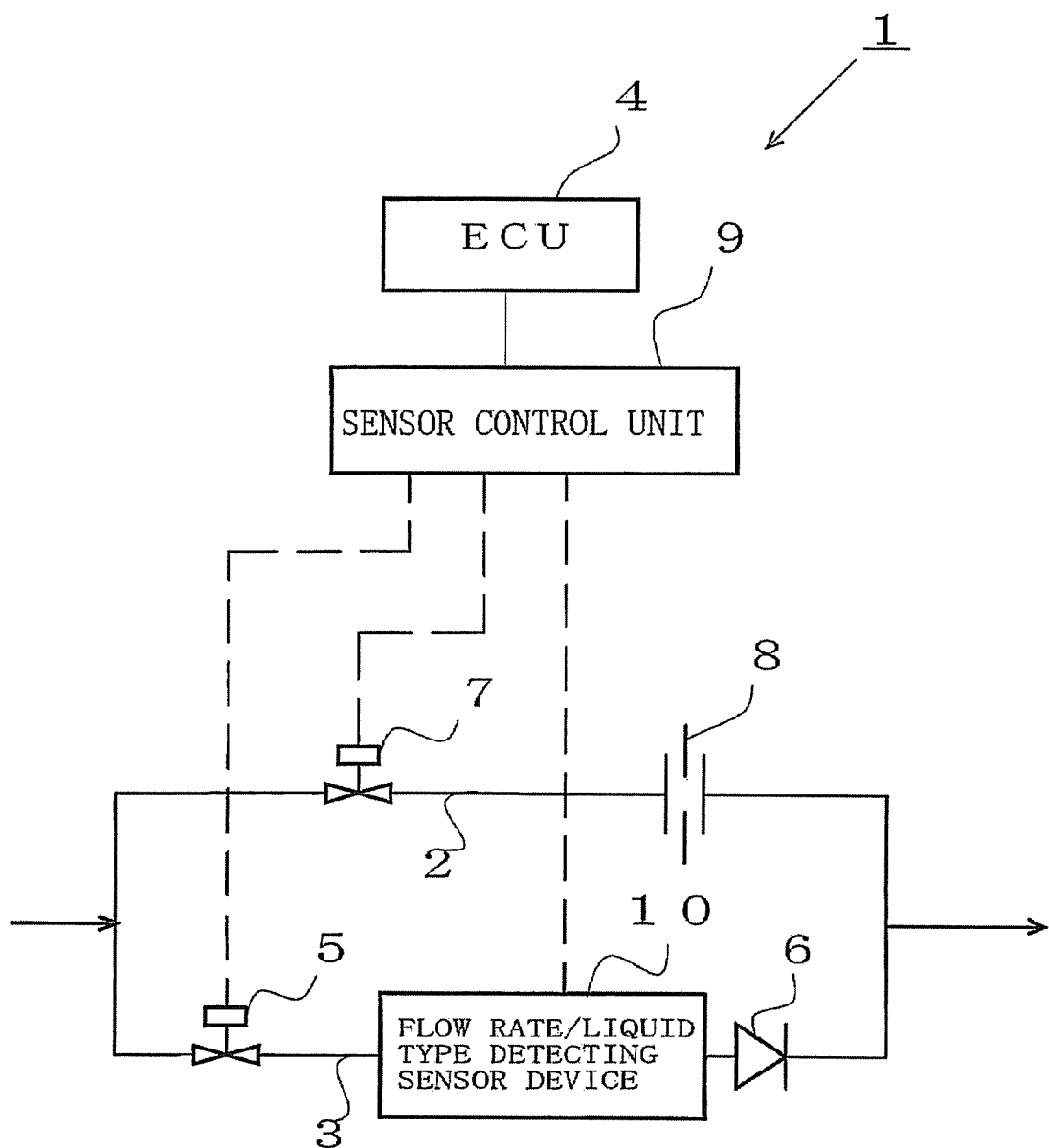
FIG. 1 is a schematic diagram showing an embodiment of a flow rate/liquid type detectingapparatus according to the present invention.

In FIG. 1, numeral 1 designates a flow rate/liquid type detecting apparatus as a whole. The flow rate/liquid type detecting apparatus 1 comprises a main passage 2 through which, for example, a fluid to be detected such as gasoline, a light oil, or a urea solution flows. An auxiliary passage 3 is branched from the main passage 2.

A flow rate/liquid type detecting sensor device 10 is provided in the auxiliary passage 3, and an auxiliary passage opening/closing valve 5 as an auxiliary passage control mechanism for controlling the flow of the fluid to be detected into the flow rate/liquid type detecting sensor device 10 is provided on the upstream side of the flow rate/liquid type detecting sensor device 10. Further, in the auxiliary passage 3, a non-return valve 6 is provided on the downstream side of the flow rate/liquid type detecting sensor device 10.

On the other hand, a main passage opening/closing valve 7 as a main passage control mechanism for controlling the flow of the fluid to be detected into the main passage is provided in the main passage 2, and an orifice 8 is provided on the downstream side of the main passage opening/closing valve 7.

Further, a sensor control unit 9 comprising a communication device for controlling the flow rate/liquid type detecting sensor device 10, the auxiliary passage opening/closing valve 5, and the main passage opening/closing valve 7 is provided. When the flow rate/liquid type detecting apparatus is applied to automobiles, ECU (an engine control unit) 4 is connected to the sensor control unit 9.

In this case, the auxiliary passage opening/closing valve 5 and the main passage opening/closing valve 7 are not particularly limited, and for example, a solenoid valve may be used.

The orifice 8 is also not particularly limited, and, for example, a flange tap orifice, a variable orifice, and an orifice with a plurality of capillaries can be adopted.

The flow rate/liquid type detecting apparatus 1 having the above construction is operated as follows.

In conducting any one of or both the detection of the type of the fluid to be detected and the detection of the concentration of the fluid to be detected, control is carried out by the sensor control unit 9 (or ECU 4) in such a manner that, after opening the auxiliary passage opening/closing valve 5, the auxiliary passage opening/closing valve 5 is closed to allow the fluid to be detected to temporarily stay within the flow rate/liquid type detecting sensor device 10 and to conduct any one of or both the detection of the liquid type and the detection of the concentration.

On the other hand, in detecting the flow rate of the fluid to be detected, control is carried out by the sensor control unit 9 (or ECU 4) in such a manner that the auxiliary passage opening/closing valve 5 is opened to allow the fluid to be detected to flow into the flow rate/liquid type detecting sensor device 10 and, in this state, the flow rate is detected.

The sensor control unit 9 (or ECU 4) is constructed so that, in this case, control is carried out in such a manner that, when the flow rate of the fluid to be detected is small, the main passage opening/closing valve 7 is closed, while, when the flow rate of said fluid to be detected is large, the main passage opening/closing valve 7 is opened.

That is to say, where the flow rate of the fluid to be detected is small, the main passage opening/closing valve 7 is closed. As a result, he fluid to be detected is flew into the auxiliary passage 3 so that the flow rate of the fluid necessary for the detection in the flow rate/liquid type detecting sensor device 10 can be ensured.

On the other hand, where the flow rate of the fluid to be detected is large, the main passage opening/closing valve 7 is opened so that the fluid is flew into the main passage 2, so that the flow rate of the fluid which flows into the auxiliary passage 3 is lowered. As a result, the flow rate of the fluid necessary for the detection in the flow rate/liquid type detecting sensor device 10 can be ensured.

Accordingly, the present invention can be utilized even when the dynamic range of the flow rate is large, and, thus, the sensitivity range can be broadened.

The provision of the non-return valve 6 on the downstream side of the flow rate/liquid type detecting sensor device 10 in the auxiliary passage 3 can prevent backward flow caused, for example, due to the occurrence of pulsating flow depending upon the type of a pump as a liquid feed device for the flow of a fluid, and the type of a drive system.

Since the backward flow within the flow rate/liquid type detecting sensor device 10 can be prevented, the detection of liquid type, the detection of concentration, and the detection of flow rate can be carried out in an accurate and rapid manner without undergoing the influence of backward flow of the fluid.

Since an orifice 8 is provided in the main passage 2, even when the pressure loss within the main passage 2 is so small that the fluid is less likely to flow into the auxiliary passage 3, the pressure loss in the main passage 2 can be increased by the orifice 8. As a result, the fluid can be allowed to flow at a given flow rate necessary for detection into the auxiliary passage 3 and, thus, the above detection can be reliably carried out.

The flow rate/liquid type detecting sensor device 10 used in the flow rate/liquid type detecting apparatus 1 according to the present invention will be described.

Figure 2:
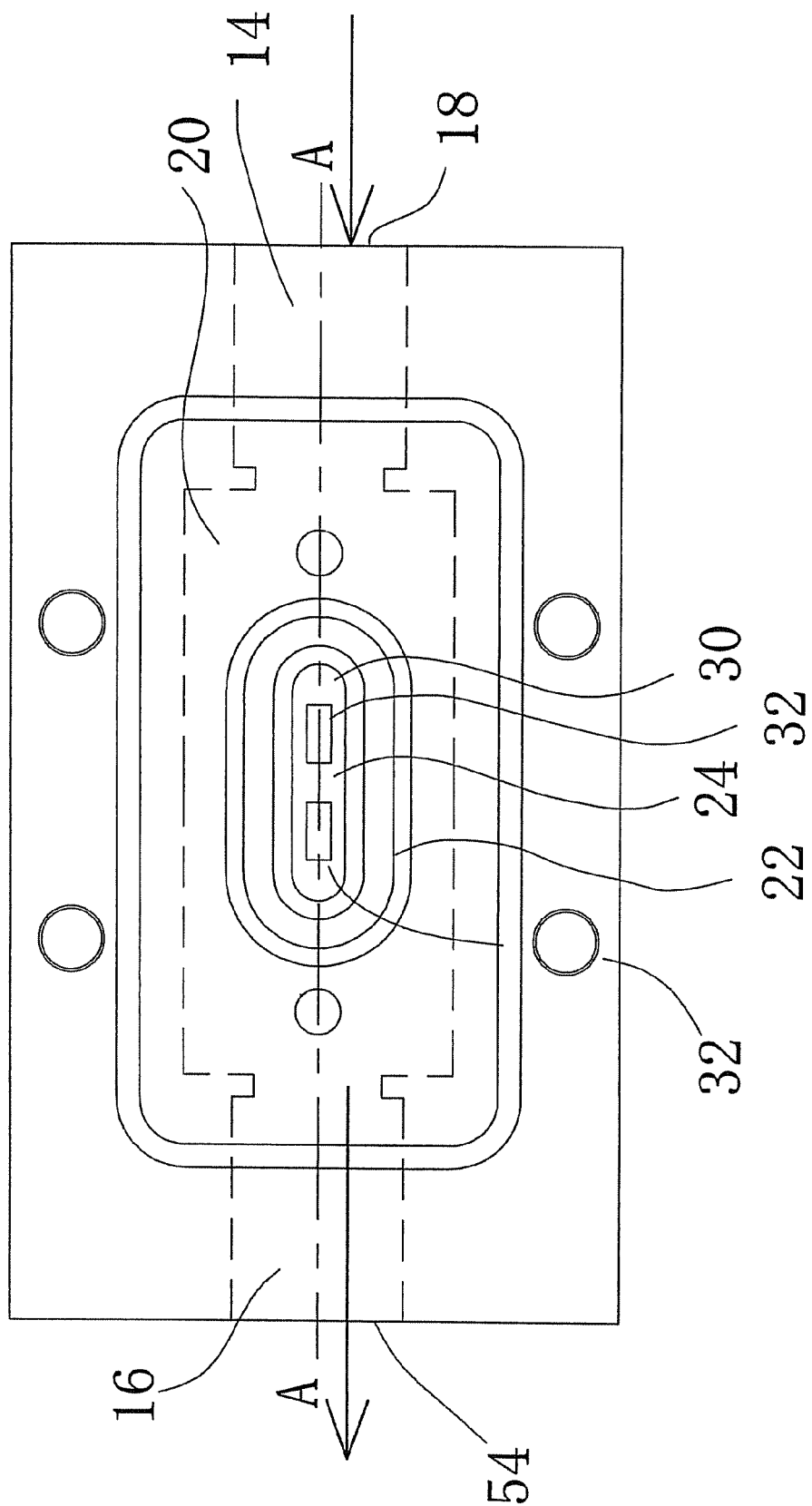
FIG. 2 is a schematic top view showing an embodiment of a flow rate/liquid typedetecting sensor device in a flow rate/liquid type detecting apparatus according to the presentinvention.
Figure 3:
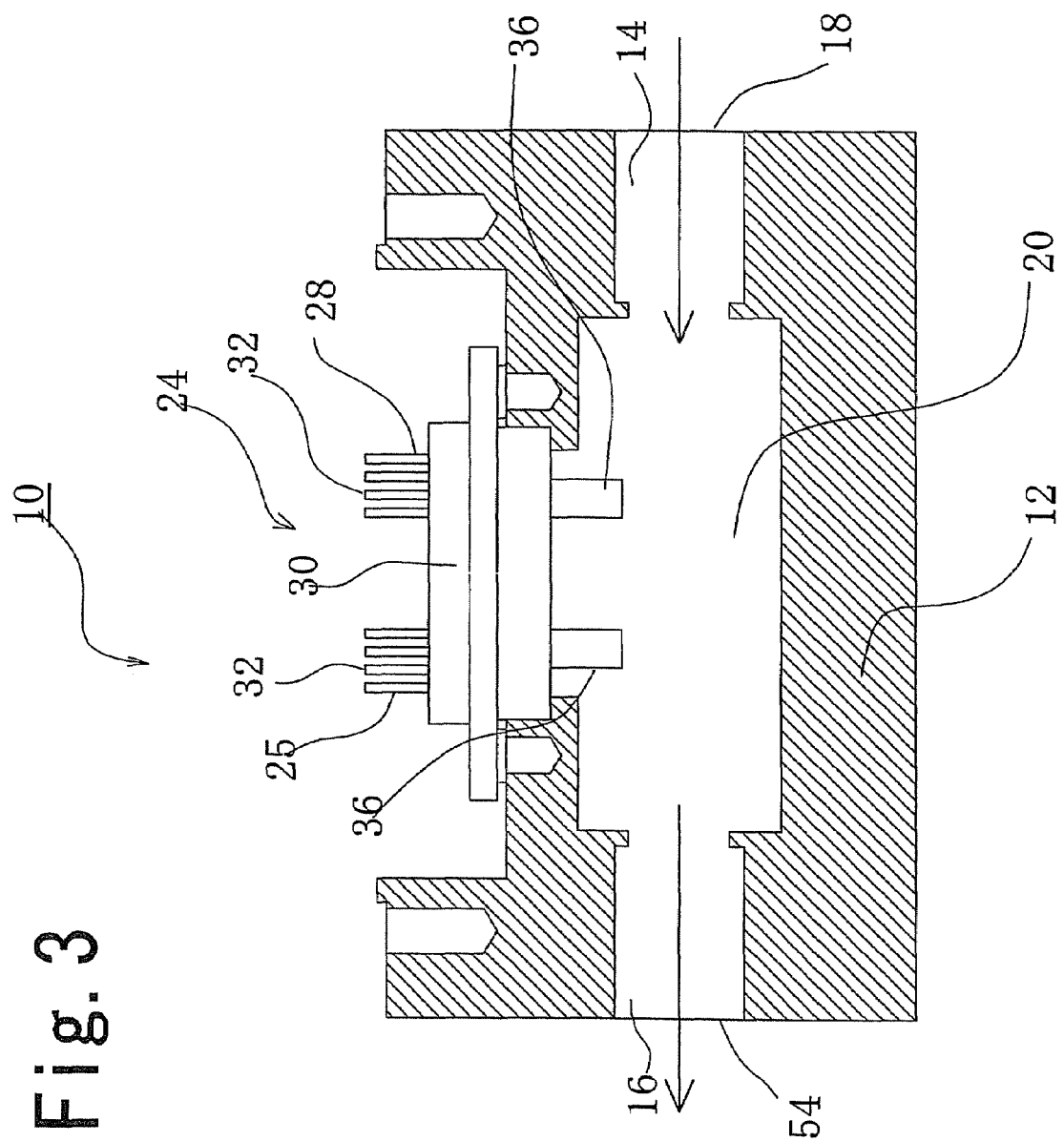
FIG. 3 is a cross-sectional view taken along line A-A of FIG. 2.

As shown in FIGS. 2 and 3, the flow rate/liquid type detecting sensor device 10 according to the present invention comprises a flow rate/liquid type detecting sensor device body 12 and a first passage 14 and a second passage 16 provided within the flow rate/liquid type detecting sensor device body 12.

As indicated by an arrow shown in FIG. 2, a fluid is introduced through a fluid inflow port 18, is passed through a first passage 14, and temporarily stays within a flow rate/liquid type detecting chamber 20. In this flow rate/liquid type detecting chamber 20, a substantially track-shaped flow rate/liquid type detecting sensor opening part 22 is provided on its upper part.

As shown in FIG. 3, a flow rate/liquid type detecting sensor 24 is mounted in the flow rate/liquid type detecting sensor opening part 22.

Figure 4:
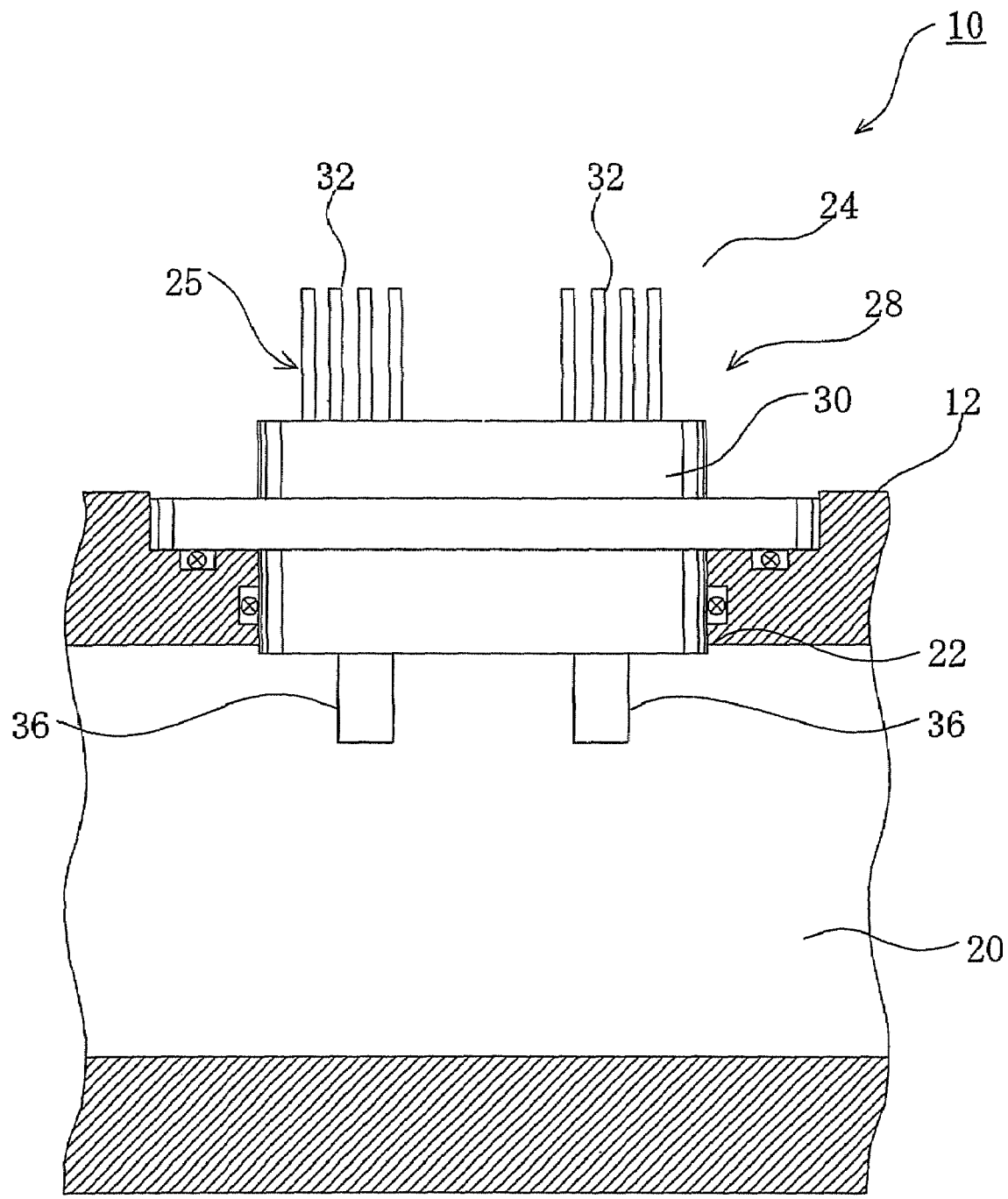
FIG. 4 is a partially enlarged cross-sectional view showing the mounted state of the flowrate/liquid type detecting sensor shown in FIG. 3.

As shown in FIG. 4, the flow rate/liquid type detecting sensor 24 comprises a flow rate/liquid type detecting sensor heater 25 and a liquid temperature sensor 28 disposed by a given distance from the flow rate/liquid type detecting sensor heater 25. The flow rate/liquid type detecting sensor heater 25 and the liquid temperature sensor 28 are formed integrally with a mold resin 30.

Figure 5:
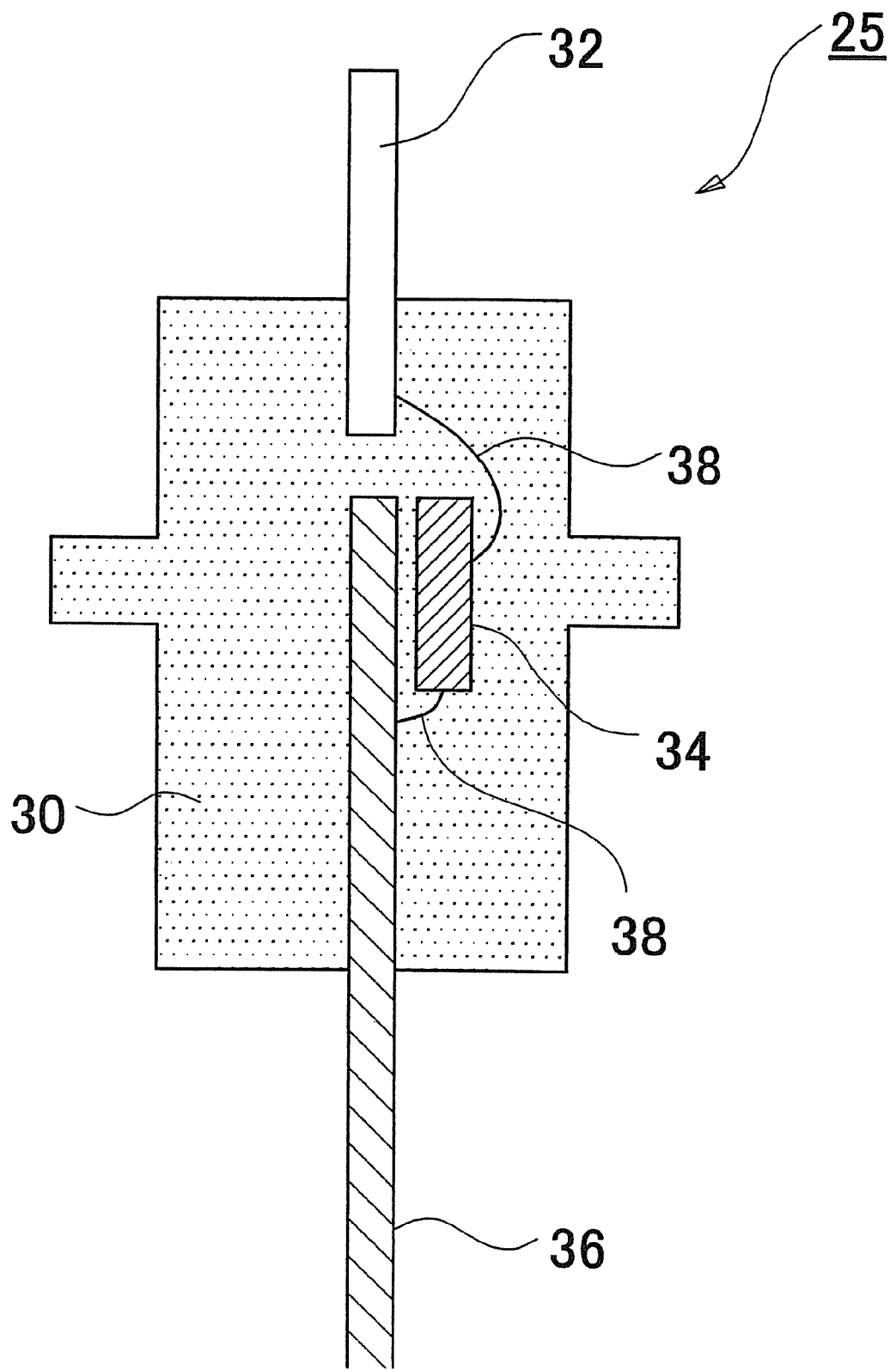
FIG. 5 is a cross-sectional view of a flow rate/liquid type detecting sensor.

Further, as shown in FIG. 5, the flow rate/liquid type detecting sensor heater 25 comprises lead electrodes 32 and a thin-film chip part 34. In the flow rate/liquid type detecting sensor heater 25, metallic fins 36 are provided. The metallic fins 36 are protruded from the mold resin 30 into the flow rate/liquid type detecting chamber 20 through the opening part 22 for a flow rate/liquid type detecting sensor so as to come into direct contact with the fluid to be detected. These lead electrodes 32, thin-film chip part 34, and fins 36 are electrically connected to each other through a bonding wire 38.

On the other hand, the liquid temperature sensor 28 has the same construction as the flow rate/liquid type detecting sensor heater 25 and comprises a lead electrode 32, a thin-film chip part 34, fins 36 and a bonding wire 38.

Figure 6:
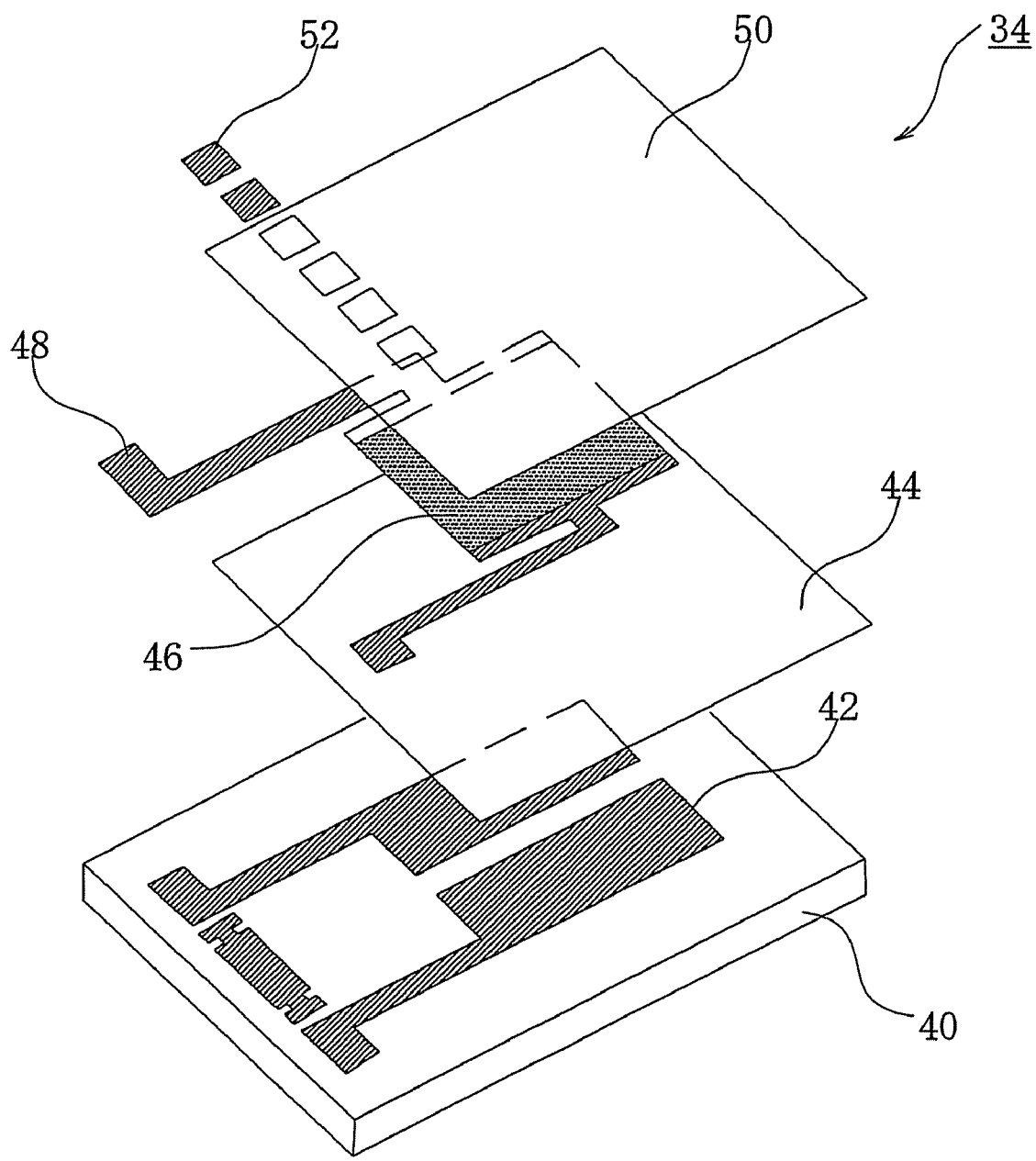
FIG. 6 is a partially enlarged exploded perspective view showing the state of stacking ofa thin-film chip part in a flow rate/liquid type detecting sensor.

As shown in FIG. 6, the thin-film chip part 34 comprises a thin-film chip comprising, for example, a substrate 40 formed of $Al_2O_3$, a temperature sensor (a temperature detector) 42 formed of Pt, an interlayer insulation film 44 formed of $SiO_2$, a heater (a heating element) 46 formed of $TaSiO_2$, a heating element electrode 48 formed of Ni, a protective film 50 formed of $SiO_2$, and an electrode pad 52 formed of Ti/Au stacked in that order.

The thin-film chip part 34 in the liquid temperature sensor 28 also has the same structure, except that only the temperature sensor (temperature detector) 42 is allowed to act without allowing the heater (heating element) 46 to act.

After the liquid type, concentration, and flow rate of the fluid to be detected are detected with this flow rate/liquid type detecting sensor 24, the detected fluid is discharged from a flow rate/liquid type detecting chamber 20, is passed through a second passage 16, and is discharged into the outside of the apparatus through a fluid discharge port 54.

In FIGS. 2 and 3, a circuit substrate member connected to the flow rate/liquid type detecting sensor 24 and a lid member covering this are omitted.

Figure 7:
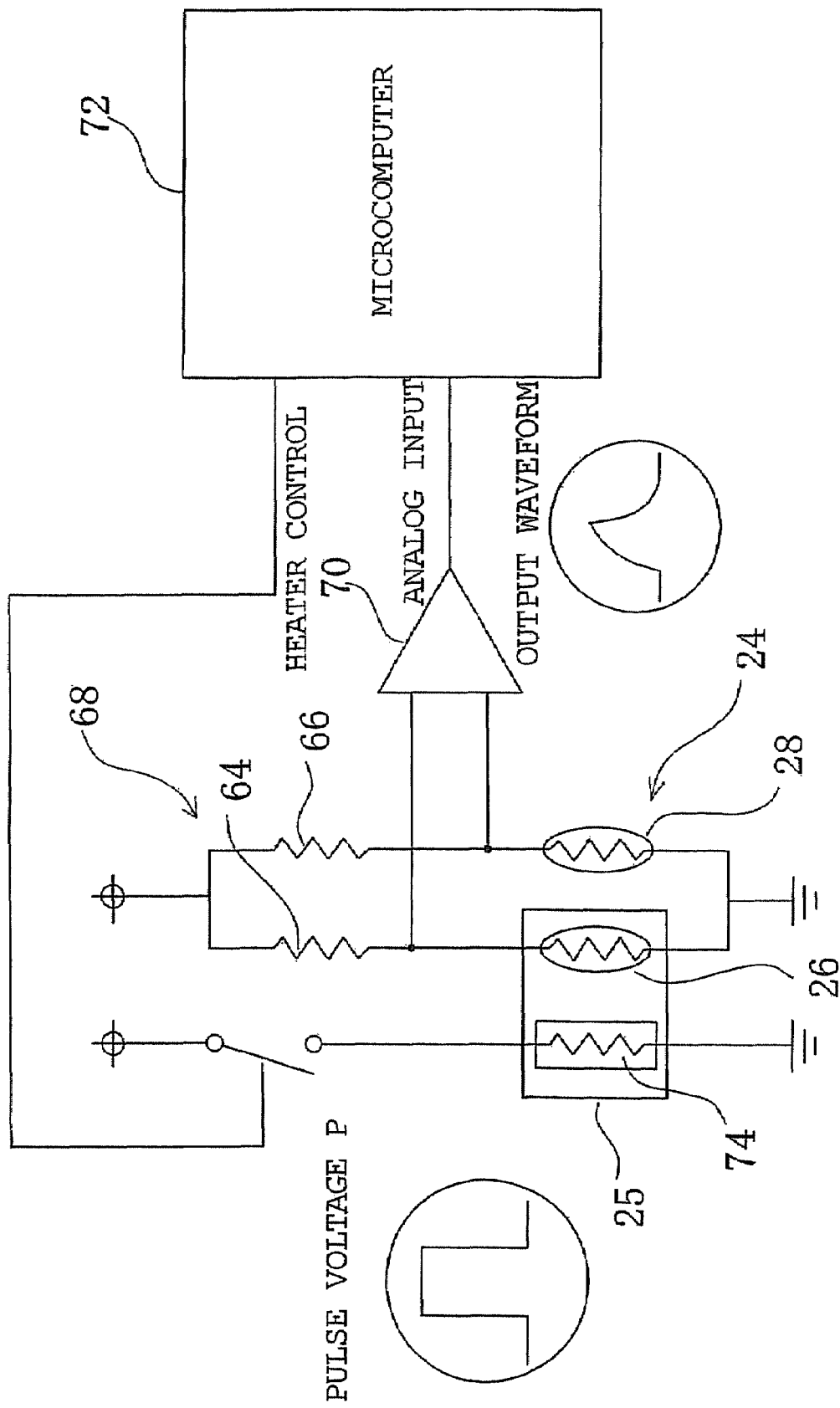
FIG. 7 is a schematic circuit block diagram of an embodiment of a flow rate/liquid typedetecting sensor device in a flow rate/liquid type detecting apparatus according to the presentinvention.

In the flow rate/liquid type detecting sensor device 10 according to the present invention, the circuit construction is as shown in FIG. 7.

In FIG. 7, a flow rate/liquid type detecting liquid temperature sensor 26 in a flow rate/liquid type detecting sensor heater 25 of a flow rate/liquid type detecting sensor 24 is connected to a liquid temperature sensor 28 through two resistors 64, 66 to constitute a bridge circuit 68. The output of the bridge circuit 68 is connected to the input of an amplifier 70. The output of this amplifier 70 is connected to the input of a computer 72 constituting a detecting control unit.

A heater 74 in the flow rate/liquid type detecting sensor heater 25 is constructed so that the applied voltage is controlled by the control of the computer 72.

In the flow rate/liquid type detecting sensor device 10 having the above construction, for example, the liquid type of gasoline is detected as follows.

First of all, control is carried out by the sensor control unit 9 (or ECU 4) in such a manner that, after the auxiliary passage opening/closing valve 5 is opened, the auxiliary passage opening/closing valve 5 is closed. As a result, the fluid to be detected is flew into the flow rate/liquid type detecting chamber 20 through the fluid inflow port 18 in the first passage 14 in the flow rate/liquid type detecting sensor device 10. Consequently, the fluid is temporarily stayed within the flow rate/liquid type detecting chamber 20.

Figure 8:
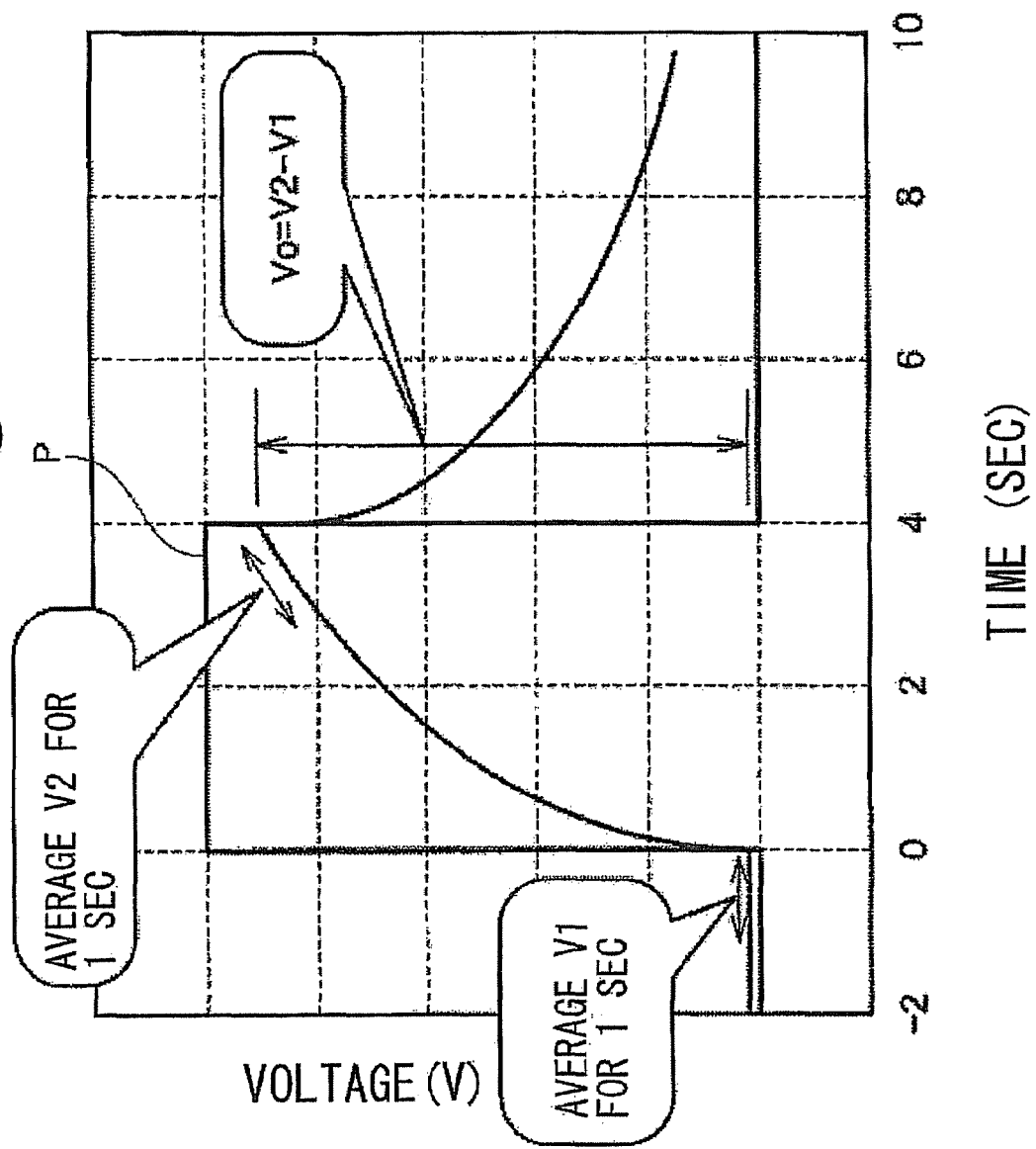
FIG. 8 is a graph showing a time vs. voltage relationship illustrating a liquid typedetecting method using a flow rate/liquid type detecting apparatus according to the presentinvention.

As shown in FIGS. 7 and 8, a pulse voltage P is applied to the heater 74 in the flow rate/liquid type detecting sensor heater 25 for a predetermined period of time, for example, for 4 sec in the case of this embodiment, by controlling the computer 72. Moreover, a change in temperature of the analog output of a sensing part, that is, a sensor bridge circuit 68 is measured as shown in FIG. 7.

That is, as shown in FIG. 8, a voltage difference in a sensor bridge circuit 68 before the application of a pulse voltage P to the heater 74 in the flow rate/liquid type detecting sensor heater 25 is sampled a predetermined number of times in one sec, for example, 256 times in the case of this embodiment. As a result, and the average value thereof is determined as an average initial voltage V1. The value of the average initial voltage V1 corresponds to the initial temperature of the flow rate/liquid type detecting liquid temperature sensor 26.

Thereafter, as shown in FIG. 8, a predetermined pulse voltage P (in this embodiment, a voltage of 10 V for 4 sec) is applied to the heater 74 in the flow rate/liquid type detecting sensor heater 25. Next, after a predetermined period of time (in this embodiment, after 3 sec), the peak voltage is sampled a predetermined number of times (in this embodiment, 256 times for one sec), and the average of sampled data is determined as an average peak voltage V2. This average peak voltage V2 corresponds to a peak temperature of the flow rate/liquid type detecting liquid temperature sensor 26.

An voltage output difference V0 is obtained from the voltage difference between an average initial voltage V1 and an average peak voltage V2, that is, $$V0=V2-V1.$$

Figure 9:
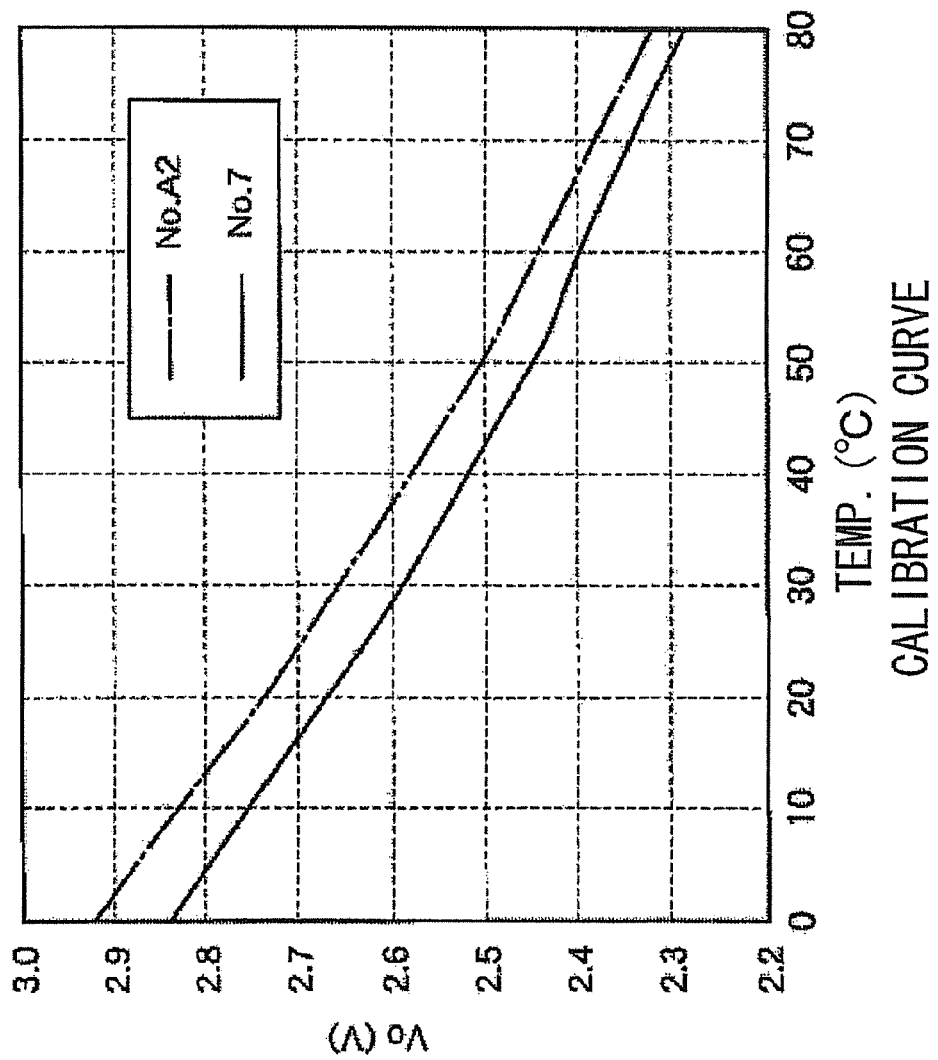
FIG. 9 is a graph showing calibration curve illustrating a liquid type detecting methodusing a flow rate/liquid type detecting apparatus according to the present invention.

Specifically, in this way, as shown in FIG. 9, for predetermined reference fluids, for example, for the heaviest (difficult to evaporate) gasoline A2 and the lightest (easy to evaporate) gasoline No. 7 in this embodiment, calibration curve data for a temperature vs. voltage output difference correlation are previously obtained and are stored in the computer 72 constituting the control unit.

Thereafter, a proportional calculation is carried out with the computer 72 based on the calibration curve data. As a result, and the type of the gasoline is detected based on the voltage output difference V0 obtained for the fluid to be detected.

Figure 10:
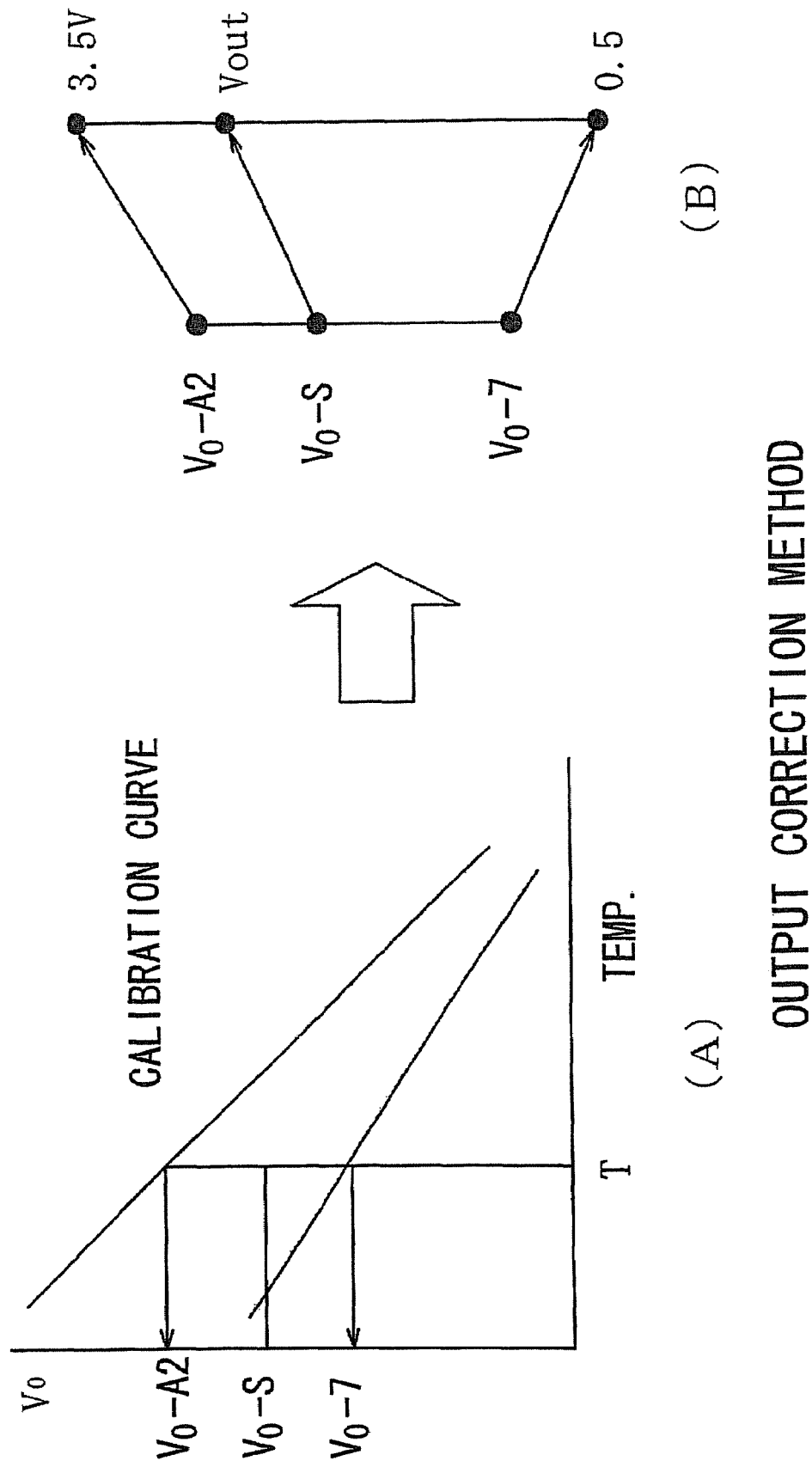
FIG. 10 is a graph illustrating an output correction method in a liquid type detectingmethod using a flow rate/liquid type detecting apparatus according to the present invention.

Specifically, as shown in FIG. 10, the voltage output Vout for the voltage output difference V0 at the measuring temperature T of the fluid to be detected is correlated with the output voltage for the voltage output difference at the measuring temperature for a predetermined threshold reference fluid (in this embodiment, gasoline A2 and gasoline No. 7) for correction.

Specifically, as shown in FIG. 10 (A), based on the calibration curve data, at a temperature T, the voltage output difference V0–A2 for gasoline A2, the voltage output difference V0–7 for gasoline No. 7, and the voltage output difference V0–S for the fluid to be detected are obtained.

As shown in FIG. 10 (B), a correlation with the properties of gasoline can be established by bringing the liquid type output of the threshold reference fluid in this case to a predetermined voltage, that is, by, in this embodiment, bringing the liquid type output of gasoline A2 to 3.5 V and bringing the liquid type output of gasoline No. 7 to 0.5 V, and obtaining the voltage output Vout of the fluid to be detected.

The liquid type of gasoline can be detected in an accurate and rapid (instantaneous) manner by comparing the voltage output Vout of the fluid to be detected with the data previously stored in the computer 72 based on the calibration curve data.

In the above case, regarding the pulse width (pulse application time), in case of the detection of liquid type and the detection of conconcentration, since the fluid to be detected stays, avoiding overheating is preferred. For this reason, the pulse width is preferably less than 5 sec. On the other hand, in the case of the detection of flow rate, the fluid to be detected does not stay. Therefore, the flow rate can be detected when the pulse width (pulse application time) is not less than 1 sec.

Figure 24:
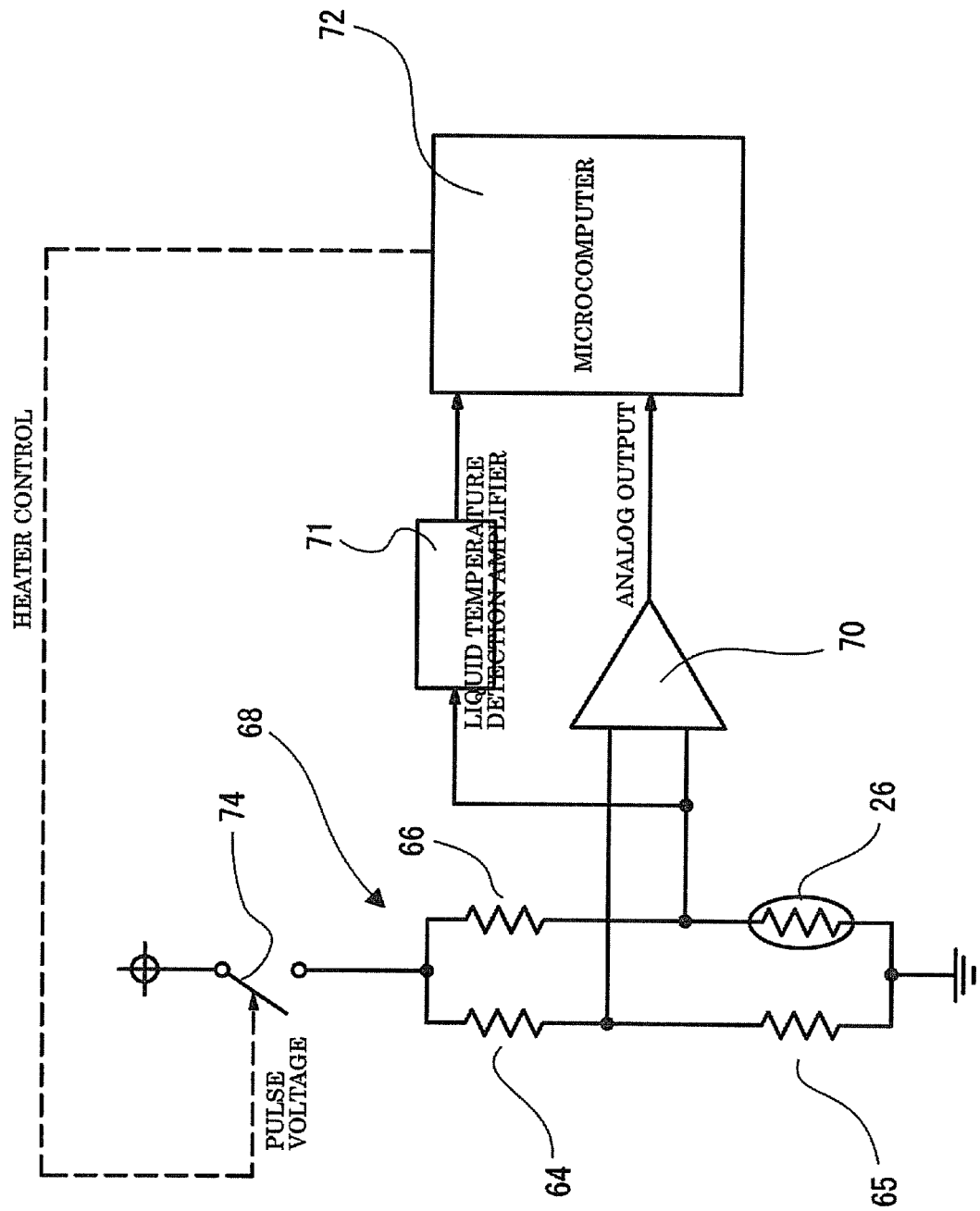
FIG. 24 is a schematic circuit block diagram of another embodiment of a flow rate/liquidtype detecting sensor device in a flow rate/liquid type detecting apparatus according to thepresent invention.

FIG. 24 shows the circuit block diagram of another embodiment of this invention.

This embodiment is the composition basically similar to the circuit for the fluid identification shown in FIG. 8, the same reference is numbering to the same member, and the detailed explanation is omitted.

In this embodiment, energizing to the sensor bridge circuit (the fluid identification circuit) 68 formed with the flow rate/liquid type detecting liquid temperature sensor as the flow rate/liquid type detecting sensor heater 26, and three resistances 64, 65, and 66 is controlled opening/closing the switch 74 according to the energizing control signal output by microcomputer 72.

In this embodiment moreover, the flow rate/liquid type detecting liquid temperature sensor 26 of the flow rate/liquid type detecting sensor 24 is composed of the material that changes the electric resistance value depending on the temperature such as Pt. Ni, Cr, and W as a metal material, NiCr, FeCr as an alloy material, NiO, FeO, CuO, Ni2O3 as an oxide material, and TaSiO2, CrSiO2 as a cermet.

By adopting such a construction, the resistance value of the flow rate/liquid type detecting liquid temperature sensor 26 changes by self-generation of heat of the flow rate/liquid type detecting liquid temperature sensor 26, the equilibrium of the bridge circuit 68 is altered, and the output voltage (sensor output) Q is obtained through the differential amplifier 70 as well as FIG. 8.

Therefore, as well as the embodiment shown in FIG. 8, the fluid to be detected is identified by obtaining on the average initial voltage V1, the average first voltage V2, and the average second voltage V3 as well as the embodiment mentioned above.

In this embodiment, in detecting temperature T of the fluid to be detected, an electric output based on the resistance value of the flow rate/liquid type detecting liquid temperature sensor 26 is obtained through the liquid temperature detection amplifier 71.

In this embodiment, the different material from the resistance 65 is used as the material of the flow rate/liquid type detecting liquid temperature sensor 26, and output voltage Q is obtained by producing the difference of the temperature alteration of the resistance value of the flow rate/liquid type detecting liquid temperature sensor 26 and the resistance 65. However, not apply only to this, for example, the resistance value of the flow rate/liquid type detecting liquid temperature sensor 26 is enlarged more than the resistance value of the resistance 65, and the calorific value of the flow rate/liquid type detecting liquid temperature sensor 26 is enlarged more than the calorific value of the resistance 65. Consequently, the equilibrium of the bridge circuit 68 is altered along with energizing to the bridge circuit 68, and output voltage Q is obtained.

Furthermore, the resistance 65 is able to be soaked as a liquid temperature sensor in the liquid where the flow rate/liquid type detecting liquid temperature sensor 26 is soaked to improve accuracy.

The above liquid type detecting method for gasoline utilize natural convection and utilizes such a principle that the kinematic viscosity of gasoline has a correlation with the sensor output.

Figure 18:
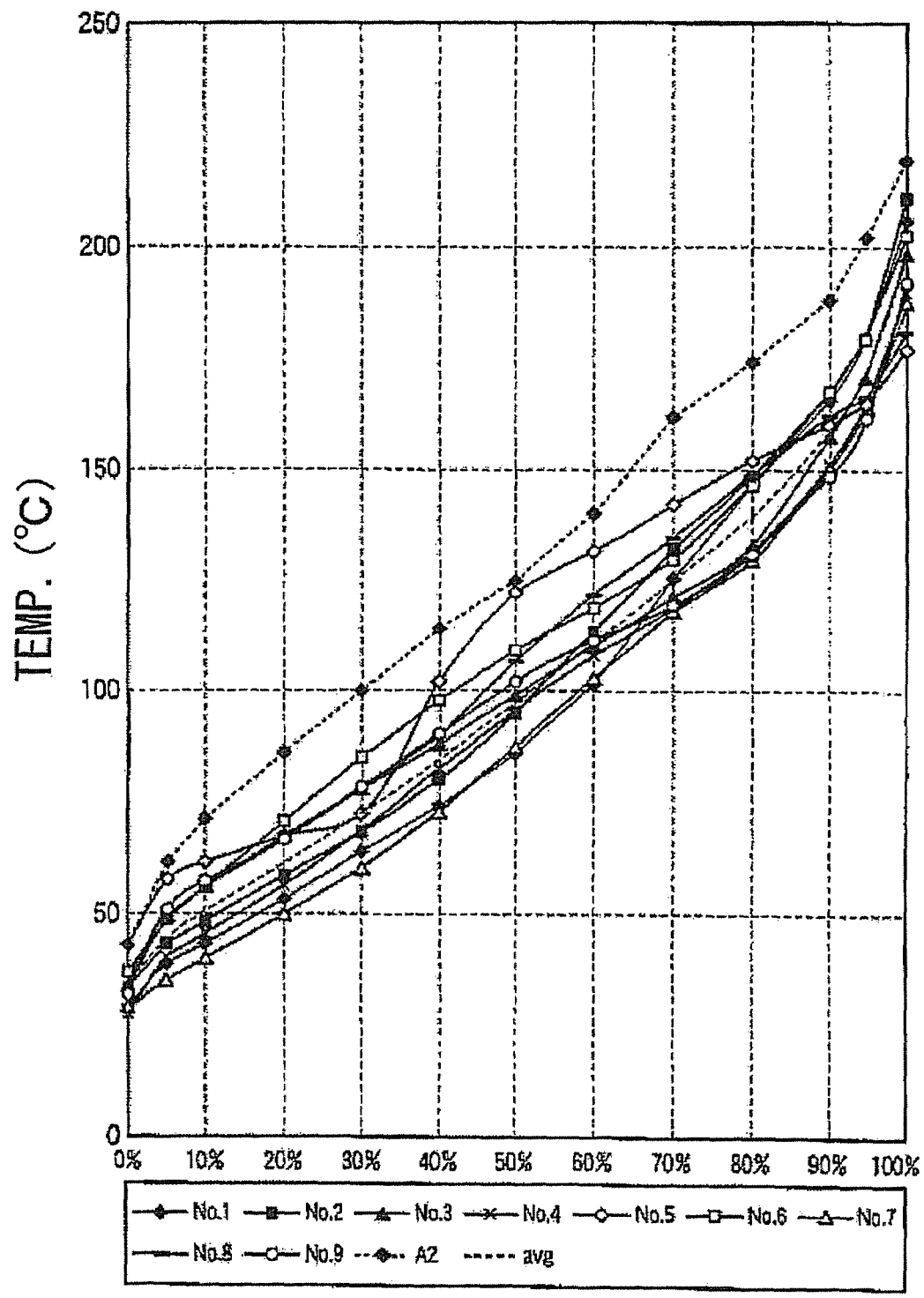
FIG. 18 is a graph showing distillation properties of gasoline.

Further, regarding the flow rate/liquid type detecting method for gasoline, in the distillation properties of gasoline shown in FIG. 18, distillation properties T30 to T70 have been found to provide a better correlation and thus are preferred.

On the other hand, in the flow rate/liquid type detecting sensor device 10, for example, the detection of the flow rate of gasoline is carried out as follows. In detecting the flow rate of the fluid to be detected, by controlling of the sensor control unit 9 (or ECU 4), the auxiliary passage opening/closing valve 5 is opened and the fluid to be detected is flew into the flow rate/liquid type detecting sensor device 10 through the fluid inflow port 18 in the first passage 14 of the flow rate/liquid type detecting sensor device 10. Thereafter, the introduced fluid is discharged from the flow rate/liquid type detecting chamber 20, is passed through the second passage 16 and is discharged through the fluid discharge port 54 into the outside of the apparatus. As a result, the fluid to be detected is such a state that the fluid is allowed to flow into the flow rate/liquid type detecting sensor device 10.

Figure 11:
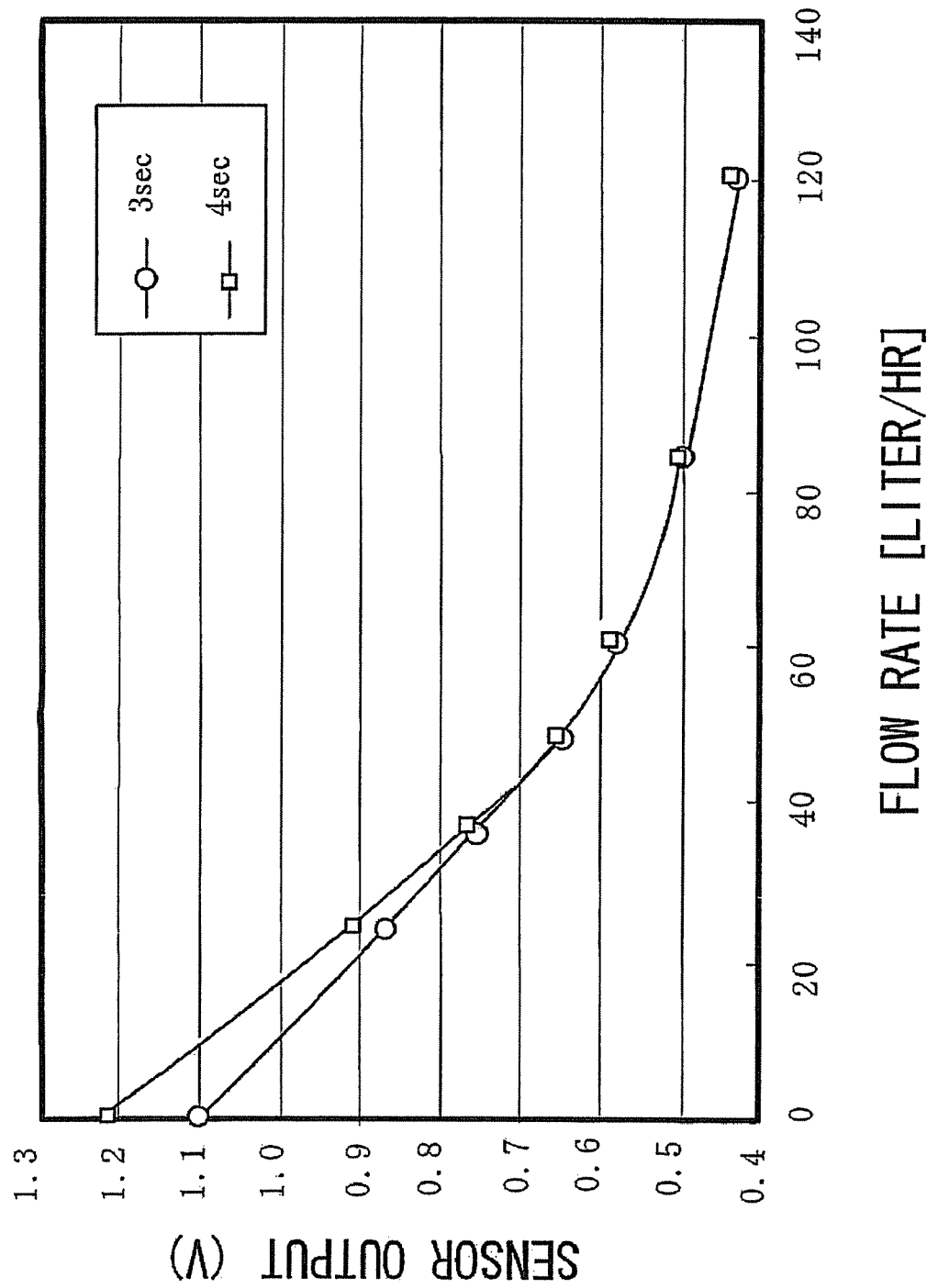
FIG. 11 is a graph showing a calibration curve illustrating a flow rate detecting methodusing a flow rate/liquid type detecting apparatus according to the present invention.

In this state, as with the detection of the liquid type, a voltage output Vout of the fluid to be detected is obtained, and the flow rate of gasoline can be detected in an accurate and rapid (instantaneous) manner by comparing voltage output Vout of the fluid to be detected with the data stored in the computer 72 based on previously measured calibration curve data for flow rate as shown in FIG. 11.

Figure 12:
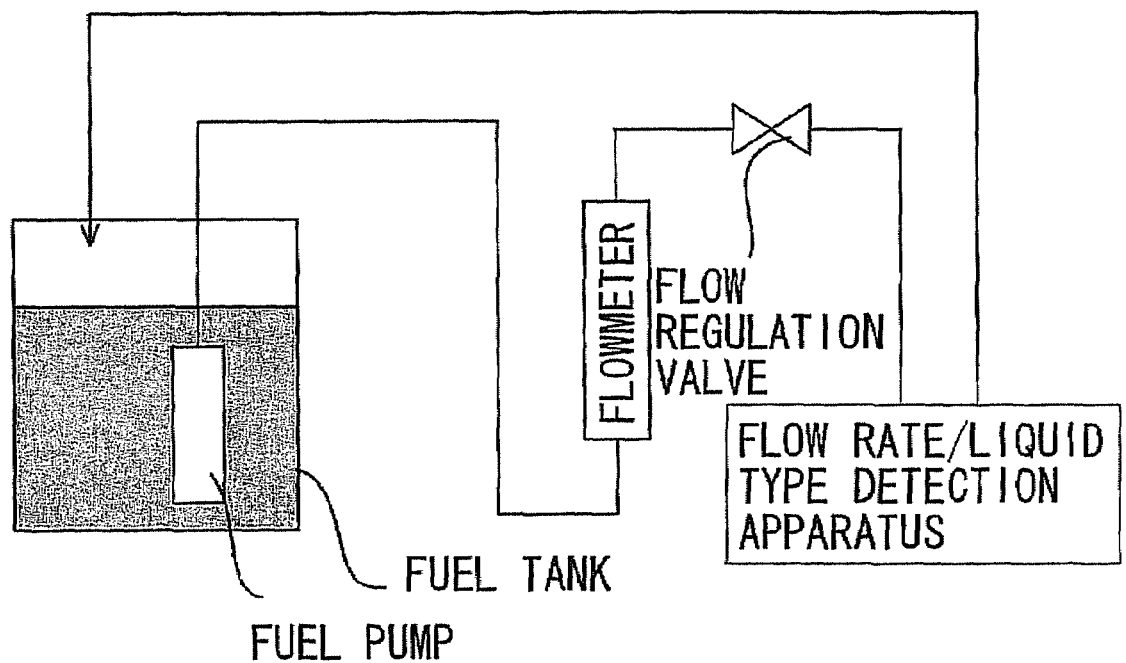
FIG. 12 is a schematic diagram of the whole measuring apparatus used for obtainingcalibration curve data shown in FIG. 11.

The calibration curve data shown in FIG. 11 are an example of the results of measurement for commercially available high-octane gasoline with a commercially available flowmeter in a measuring apparatus as shown in FIG. 12.

In this case, the flow rate is 0 to 180 liters/hr, and the measurement in the flow rate/liquid type detecting sensor device 10 is carried out under conditions of a pulse time of 3 to 5 sec, preferably 4 sec, a pulse voltage of 10 V (corresponding to 250 mV), a pulse application time of 5 to 12 sec, and a temperature of 0 to 80° C.

Further, when the concentration of the fluid to be detected is measured, for example, in the case of an identification urea solution, as with the detection of the liquid type, the voltage output Vout can be obtained and correlated with the properties of urea.

Figure 13:
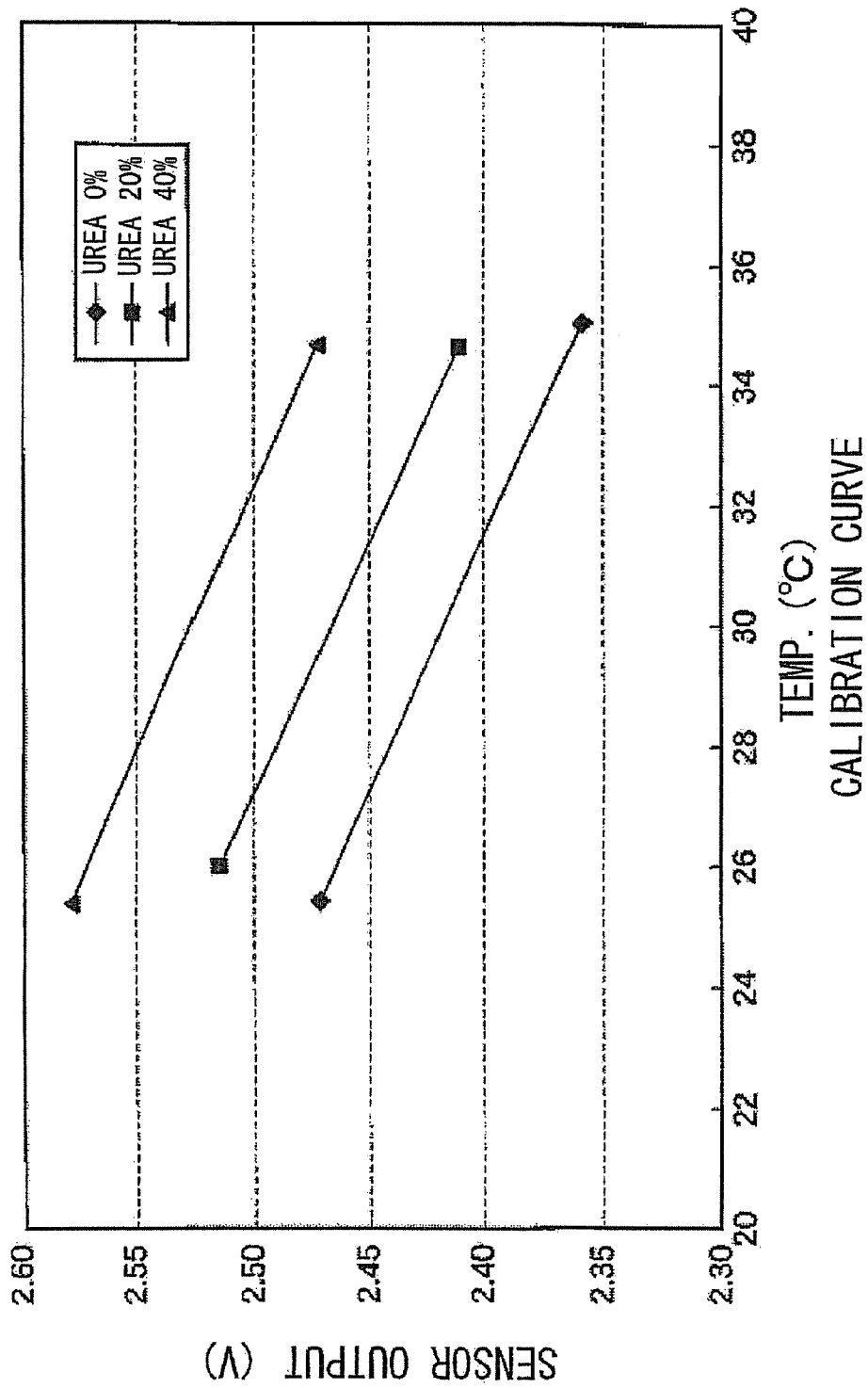
FIG. 13 is a graph showing a calibration curve illustrating a concentration detectingmethod using a flow rate/liquid type detecting apparatus according to the present invention.

The content of urea in the urea solution can be identified in an accurate and rapid (instantaneous) manner by comparing the voltage output Vout of the urea solution to be identified with data stored in the computer 72 based on previously measured calibration data for a urea solution as shown in FIG. 13. In FIG. 1, numeral 10 designates a liquid type detecting apparatus according to the present invention as a whole. The liquid type detecting apparatus 10 comprises an approximately box-shaped liquid type detecting apparatus body 12 through which a fluid to be detected such as gasoline, a light oil, or a urea solution flows.

Figure 20:
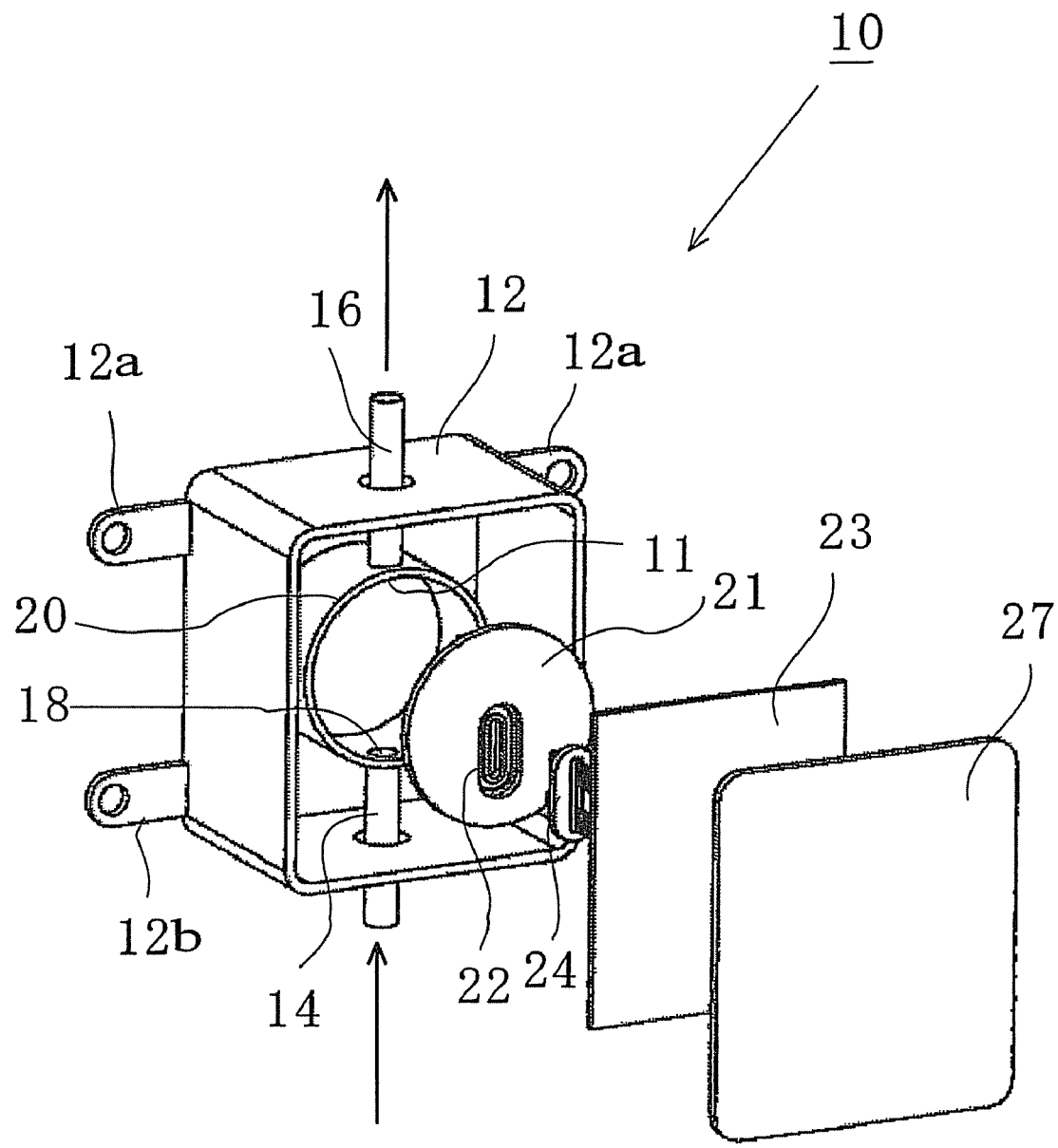
FIG. 20 i s an exploded perspective view of the whole liquid type detecting apparatusaccording to the present invention.
Figure 21:
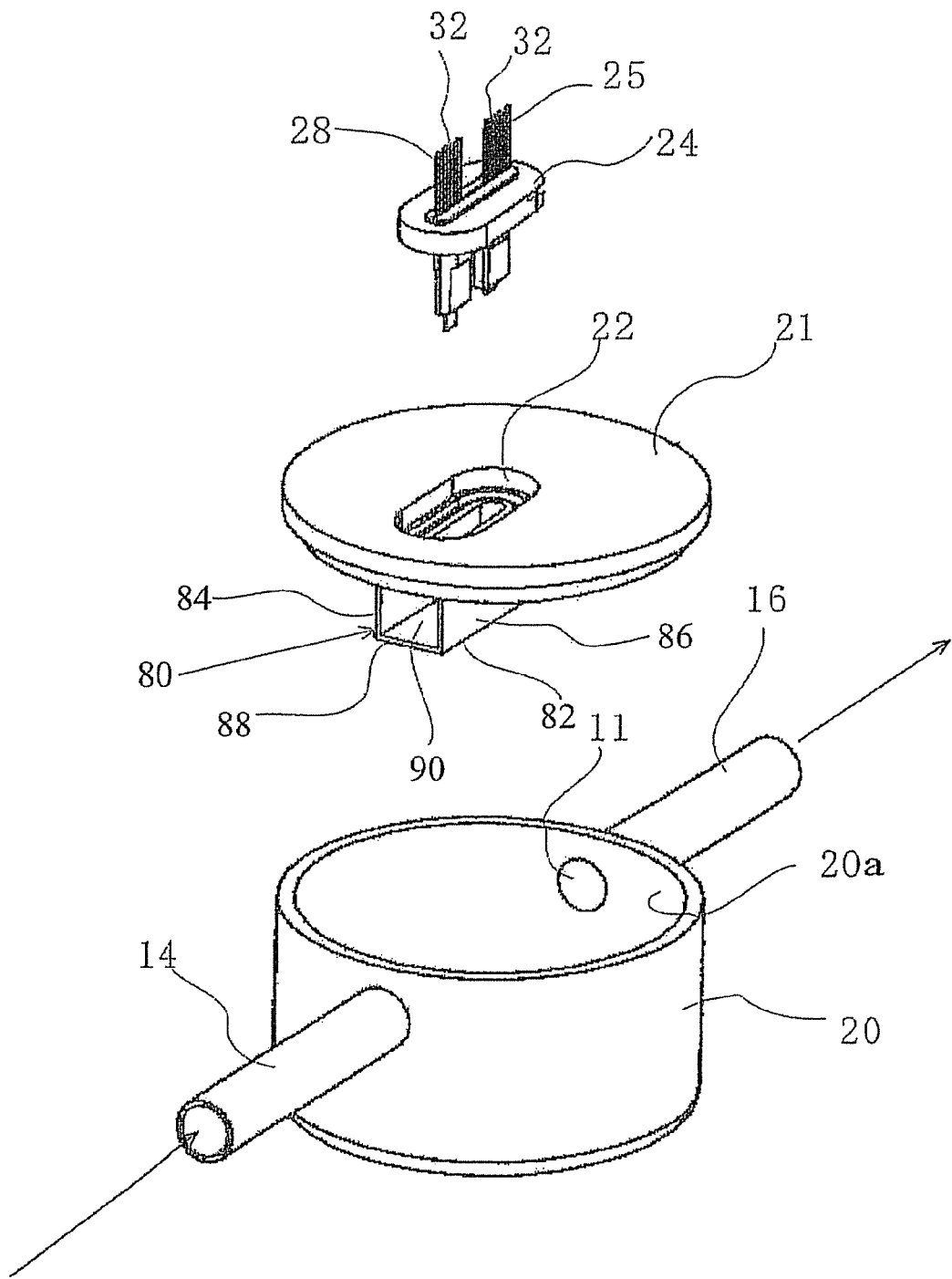
FIG. 21 is an exploded perspective view of a liquid type detecting chamber in a liquidtype detecting apparatus according to the present invention.

FIG. 20 is an exploded perspective view of the whole liquid type detecting apparatus according to the present invention, and FIG. 21 an exploded perspective view of a liquid type detecting chamber in the liquid type detecting apparatus according to the present invention.

The liquid type detecting apparatus in this embodiment basically uses the same constituent members as used in the flow rate/liquid type detecting sensor device 10 shown in FIGS. 3 to 10. Accordingly, the liquid type detecting apparatus will be described in detail while changing the term "flow rate/liquid type detecting" in the flow rate/liquid type detecting sensor device 10 shown in FIGS. 3 to 10 to the term "liquid type detecting".

As shown in FIG. 20, an approximately circular tube-shaped liquid type detecting chamber 20 is provided within a liquid type detecting apparatus body 12 in this apparatus. Further, a first passage 14 and a second passage 16 are provided in the liquid type detecting apparatus body 12.

The first passage 14 is connected to a fluid introduction port 18 provided in the liquid type detecting chamber 20. The second passage 16 is connected to a fluid discharge port 11 provided in the liquid type detecting chamber 20.

The liquid type detecting apparatus is constructed so that, as indicated by an arrow in FIG. 21, the fluid to be detected introduced into the liquid type detecting apparatus body 12 is introduced from the first passage 14 through the fluid introduction port 18 into the liquid type detecting chamber 20 where the fluid temporarily stays.

A lid member 21 for a liquid type detecting chamber is mounted on the upper part of the liquid type detecting chamber 20. An approximately track-shaped opening 22 for a liquid type detecting sensor is provided in the lid member 21 for a liquid type detecting chamber.

As shown in FIG. 3, a liquid type detecting sensor 24 is mounted in the liquid type detecting sensor opening part 22.

As shown in FIG. 4, the liquid type detecting sensor 24 comprises a liquid type detecting sensor heater 25 and a liquid temperature sensor 28 disposed by a given distance from the liquid type detecting sensor heater 25. The liquid type detecting sensor heater 25 and the liquid temperature sensor 28 are formed integrally with a mold resin 30.

Further, as shown in FIG. 5, the liquid type detecting sensor heater 25 comprises lead electrodes 32 and a thin-film chip part 34. In the liquid type detecting sensor heater 25, metallic fins 36 are provided. The metallic fins 36 are protruded from the mold resin 30 into the liquid type detecting chamber 20 through the opening part 22 for a liquid type detecting sensor so as to come into direct contact with the fluid to be detected. These lead electrodes 32, thin-film chip part 34, and fins 36 are electrically connected to each other through a bonding wire 38.

On the other hand, the liquid temperature sensor 28 has the same construction as the liquid type detecting sensor heater 25 and comprises a lead electrode 32, a thin-film chip part 34, fins 36 and a bonding wire 38.

As shown in FIG. 6, the thin-film chip part 34 comprises a thin-film chip comprising, for example, a substrate 40 formed of $Al_2O_3$, a temperature sensor (a temperature detector) 42 formed of Pt, an interlayer insulation film 44 formed of $SiO_2$, a heater (a heating element) 46 formed of $TaSiO_2$, a heating element electrode 48 formed of Ni, a protective film 50 formed of $SiO_2$, and an electrode pad 52 formed of Ti/Au stacked in that order.

The thin-film chip part 34 in the liquid temperature sensor 28 also has the same structure, except that only the temperature sensor (temperature detector) 42 is allowed to act without allowing the heater (heating element) 46 to act.

After the liquid type and concentration of the fluid to be detected are detected with this liquid type detecting sensor 24, the detected fluid is discharged from a liquid type detecting chamber 20, is passed through a second passage 16 through a fluid discharge port 11 in the liquid type detecting chamber 20, and is discharged into the outside of the apparatus.

Further, as shown in FIG. 20, the liquid type detecting sensor 24 is provided with a circuit board member 23 and an outer lid member 27 covering the circuit board member 23. In FIGS. 21 and 3, the circuit board member 23 and the outer lid member 27 are not shown for the convenience of explanation.

In FIG. 20, reference characters 12a, 12b each designate a mounting flange for mounting the liquid type detecting apparatus 10 provided in the liquid type detecting apparatus body 12, for example, on automobiles.

On the other hand, as shown in FIG. 21, a flow control plate 1 is provided on the inner side of the lid member 21 for a liquid type detecting chamber so that the flow control plate 1 surrounds a liquid type detecting sensor 24, which is provided so as to be protruded into the liquid type detecting chamber 20.

This flow control plate 1 is formed of a plate member 2 of a substantially U shape in section. This plate member 2 comprises a pair of side plate members 3, 4, which surrounds the liquid type detecting sensor 24 from both sides thereof and extends from the fluid introduction port 18 in the liquid type detecting chamber 20 toward the fluid discharge port 11. Moreover, this plate member 2 comprises a covering plate member 5 connected to these side plate members 3, 4.

The flow control plate 1 has a fluid inflow port 6 which confronts the fluid introduction port 18 in the liquid type detecting chamber 20 and a fluid outflow port 7 which confronts the fluid discharge port 11 in the liquid type detecting chamber 20.

The fluid introduction port 18 in the liquid type detecting chamber 20 and the fluid inflow port 6 in the flow control plate 1 are spaced from each other by a predetermined distance L1. Moreover, the fluid discharge port 11 in the liquid type detecting chamber 20 and the fluid outflow port 7 in the flow control plate 1 are spaced from each other by a predetermined distance L2.

According to the above construction, in the case where the introduction of the fluid to be detected into the liquid type detecting apparatus body 12 is stopped to allow the fluid to be detected to temporarily stay within the liquid type detecting chamber 20, the flow of the fluid to be detected within the liquid type detecting chamber 20 is suppressed by the flow control plate 1. Consequently, the flow of the fluid to be detected around the liquid type detecting sensor 24, which is located within the flow control plate 1 surrounded by this flow control plate 1, is instantaneously stopped.

Specifically, the fluid to be detected is reliably introduced, from the fluid introduction port 18 in the liquid type detecting chamber 20, into the flow control plate 1 surrounded by the flow control plate 1, through the fluid inflow port 6 in the flow control plate 1. As a result, the fluid to be detected is reliably entereed the circumference of the liquid type detecting sensor 24 which is located within the fluid control plate 1, so that the liquid type and concentration of the fluid to be detected can be detected with the liquid type detecting sensor 24.

After the liquid type and concentration of the fluid to be detected is detected with the liquid type detecting sensor 24, the fluid after the detection can be reliably discharged from the liquid discharge port 11 in the liquid type detecting chamber 20 through the fluid outflow port 7 in the flow control plate 1. Therefore, the detection of the fluid to be detected can be successively carried out with good accuracy.

Therefore, in detecting the liquid type and concentration with the liquid type detecting sensor 24, the flow of the fluid to be detected does not occur, and, further, turbulence of the fluid to be detected by the vibration does not occur. Thus, the influence on the detection of the liquid type and concentration of the fluid to be detected can be prevented, and the liquid type and concentration of the fluid to be detected can be accurately measured.

Further, since a liquid type detecting chamber 20 is provided, the amount of stay of the fluid to be detected is increased. Therefore, the type and concentration of the fluid to be detected can be accurately detected without undergoing the influence of ambient environment such as external temperature.

Accordingly, when the present invention is applied, for example, to fluids such as automotive gasoline and light oils, upon stop of an automobile, for example, due to waiting for a signal, a fuel pump can be stopped and the liquid type and concentration of the fluid to be detected can be instantaneously detected. In this case, after the completion of the detection, the fuel pump can be started to again start the automobile. Therefore, the detection is not an obstacle to the driving of the automobile.

Figure 22:
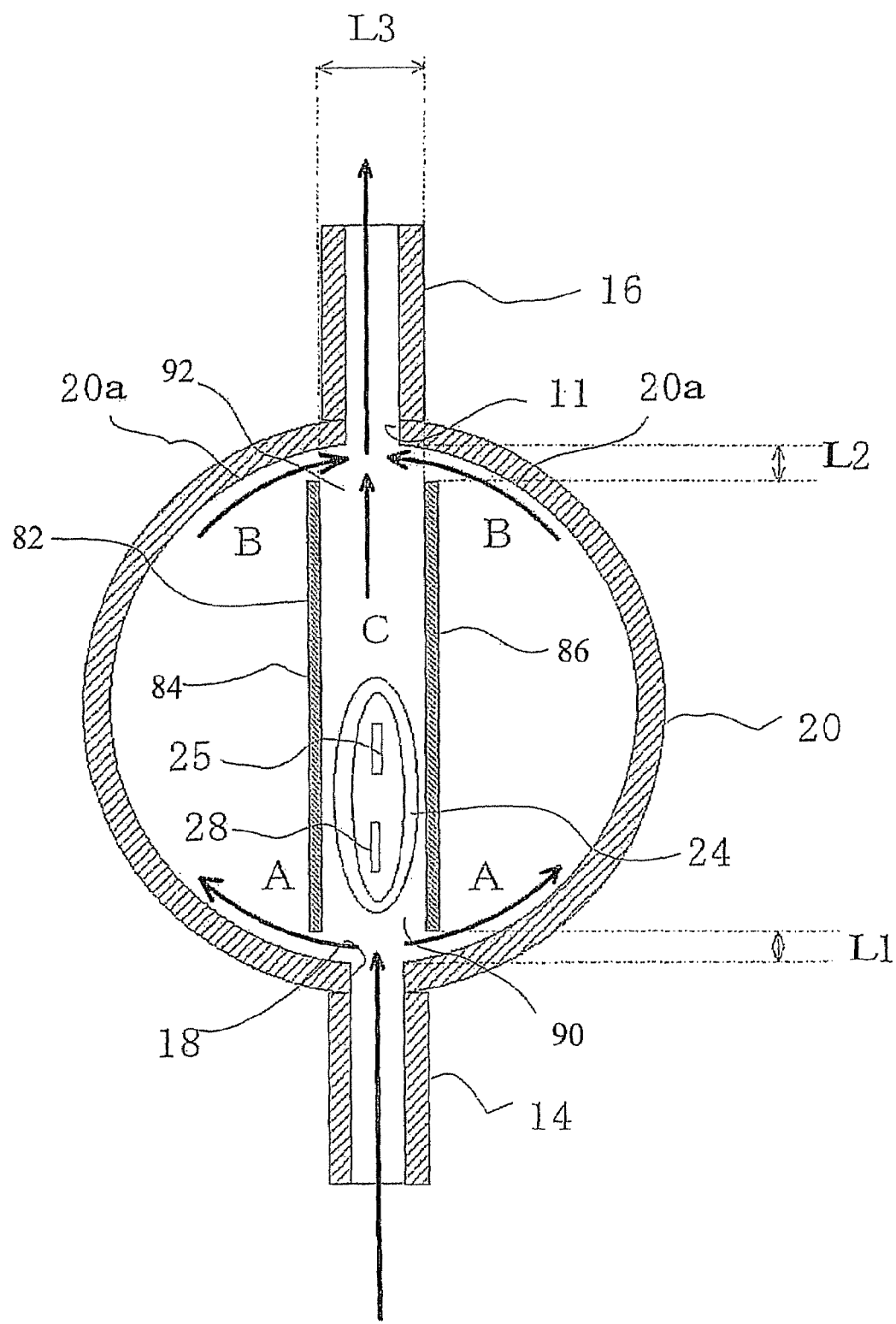
FIG. 22 is a schematic diagram illustrating the state of detection of a liquid type detectingchamber in a liquid type detecting apparatus according to the present invention.

Further, as indicated by an arrow B in FIG. 22, in this detection, air mixed into the fluid to be detected can be reliably discharged from the fluid discharge port 11 in the liquid type detecting chamber 20 through the fluid outflow port 7 in the flow control plate 1. Therefore, air does not stay around the liquid type detecting sensor 24, and the influence on the detection can be prevented, contributing to accurate detection.

Since the fluid introduction port 18 in the liquid type detecting chamber 20 and the fluid inflow port 6 in the flow control plate 1 are spaced from each other by a predetermined distance L1, as indicated by an arrow A in FIG. 22, air mixed into the fluid to be detected is moved through the space toward the outside of the flow control plate 1 and is discharged to the outside of the liquid type detecting chamber 20 through the fluid discharge port 11.

Therefore, the air does not enter the inside of the flow control plate 1, and, thus, air does not stay around the liquid type detecting sensor 24. This can realize the prevention of the influence of air on the detection and thus can contribute to accurate detection.

Even though air enters the inside of the flow control plate 1, as indicated by an arrow C in FIG. 22, this air can be reliably discharged from the fluid discharge port 11 in the liquid type detecting chamber 20 through the fluid outflow port 7 in the flow control plate 1. Therefore, the air does not stay around the liquid type detecting sensor 24. This can realize the prevention of the influence of air on the detection and thus can contribute to accurate detection.

Further, as indicated by an arrow B in FIG. 22, the side wall in the vicinity of the fluid discharge port 11 in the liquid type detecting chamber 20 is provided in an approximately circular tube form, that is, in an approximately arc form. Therefore, air mixed into the fluid to be detected is guided inward along the approximately arc-shaped side wall 20a in the liquid type detecting chamber 20 to the fluid discharge port 11 in the liquid type detecting chamber 20 and is then discharged.

Therefore, the air does not stay around the fluid discharge port 11 in the liquid type detecting chamber 20 and does not stay around the liquid type detecting sensor 24. This can realize the prevention of the influence of air on the detection and thus can contribute to accurate detection.

In order to realize the above function and effect, as shown in FIG. 22, the above predetermined distance L1, L2 is preferably 1.5 mm to 5 mm, more preferably 2 mm to 3.5 mm. Further, the distance L3 between the pair of side plate members 3, 4 in the flow control plate 1 and the liquid type detecting sensor 24 is preferably 5 mm to 10 mm, more preferably 6 mm to 8 mm.

The size of the liquid type detecting chamber 20 is not particularly limited.

Further, the material for constituting the liquid type detecting chamber 20 is not particularly limited. For example, metals such as stainless steel including SUS 304, synthetic resins such as polyacetal (POM), and fiber reinforced resins such as FRPs are usable.

The material for constituting the flow control plate 1 is also not particularly limited. For example, metals such as stainless steel including SUS 304, synthetic resins such as polyacetal (POM), fiber reinforced resins such as FRPs, and ceramics are usable.

In the liquid type detecting apparatus 10 according to the present invention, the circuit construction is as shown in FIG. 7.

In FIG. 7, a liquid type detecting liquid temperature sensor 26 in a liquid type detecting sensor heater 25 of a liquid type detecting sensor 24 is connected to a liquid temperature sensor 28 through two resistors 64, 66 to constitute a bridge circuit 68. The output of the bridge circuit 68 is connected to the input of an amplifier 70. The output of this amplifier 70 is connected to the input of a computer 72 constituting a detecting control unit.

A heater 74 in the liquid type detecting sensor heater 25 is constructed so that the applied voltage is controlled by the control of the computer 72.

In the liquid type detecting apparatus 10 having the above construction, for example, the liquid type of gasoline is detected as follows.

First of all, control is carried out by a control unit (not shown) in such a manner that the fluid to be detected is introduced into the liquid type detecting apparatus body 12, is passed through the first passage 14 and the fluid introduction port 18, and is allowed to flow into the liquid type detecting chamber 20. Thereafter, the inflow of the fluid to be detected is stopped to allow the fluid to temporarily stay in the liquid type detecting chamber 20.

In this state, when the introduction of the fluid to be detected into the liquid type detecting apparatus body 12 is stopped to allow the fluid to temporarily stay in the liquid type detecting chamber 20. In addition, the flow of the fluid to be detected within the liquid type detecting chamber 20 is hindered by the flow control plate 1. Consequently, the flow of the fluid to be detected around the liquid type detecting sensor 24, which is located within the flow control plate 1 surrounded by the flow control plate 1, is instantaneously stopped.

In this state, as shown in FIGS. 7 and 8, a pulse voltage P is applied to the heater 74 in the liquid type detecting sensor heater 25 for a predetermined period of time, for example, for 4 sec in the case of this embodiment, by controlling the computer 72. Thereafter, a change in temperature of the analog output of a sensing part, that is, a sensor bridge circuit 68 is measured as shown in FIG. 7.

That is, as shown in FIG. 8, a voltage difference in a sensor bridge circuit 68 before the application of a pulse voltage P to the heater 74 in the liquid type detecting sensor heater 25 is sampled a predetermined number of times in one sec, for example, 256 times in the case of this embodiment. As a result, and the average value thereof is determined as an average initial voltage V1. The value of the average initial voltage V1 corresponds to the initial temperature of the liquid type detecting liquid temperature sensor 26.

Thereafter, as shown in FIG. 8, a predetermined pulse voltage P (in this embodiment, a voltage of 10 V for 4 sec) is applied to the heater 74 in the liquid type detecting sensor heater 25. Next, after a predetermined period of time (in this embodiment, after 3 sec), the peak voltage is sampled a predetermined number of times (in this embodiment, 256 times for one sec), and the average of sampled data is determined as an average peak voltage V2. This average peak voltage V2 corresponds to a peak temperature of the liquid type detecting liquid temperature sensor 26.

An voltage output difference V0 is obtained from the voltage difference between an average initial voltage V1 and an average peak voltage V2, that is, $$V0 = V2 - V1.$$

Specifically, in this way, as shown in FIG. 9, for predetermined reference fluids, for example, for the heaviest (difficult to evaporate) gasoline A2 and the lightest (easy to evaporate) gasoline No. 7 in this embodiment, calibration curve data for a temperature vs. voltage output difference correlation are previously obtained and are stored in the computer 72 constituting the control unit.

Thereafter, a proportional calculation is carried out with the computer 72 based on the calibration curve data, and the type of the gasoline is detected based on the voltage output difference V0 obtained for the fluid to be detected.

Specifically, as shown in FIG. 10, the voltage output Vout for the voltage output difference V0 at the measuring temperature T of the fluid to be detected is correlated with the output voltage for the voltage output difference at the measuring temperature for a predetermined threshold reference fluid (in this embodiment, gasoline A2 and gasoline No. 7) for correction.

Specifically, as shown in FIG. 10 (A), based on the calibration curve data, at a temperature T, the voltage output difference V0–A2 for gasoline A2, the voltage output difference V0–7 for gasoline No. 7, and the voltage output difference V0–S for the fluid to be detected are obtained.

As shown in FIG. 10 (B), a correlation with the properties of gasoline can be established by bringing the liquid type output of the threshold reference fluid in this case to a predetermined voltage, that is, by, in this embodiment, bringing the liquid type output of gasoline A2 to 3.5 V and bringing the liquid type output of gasoline No. 7 to 0.5 V, and obtaining the voltage output Vout of the fluid to be detected.

The liquid type of gasoline can be detected in an accurate and rapid (instantaneous) manner by comparing the voltage output Vout of the fluid to be detected with the data previously stored in the computer 72 based on the calibration curve data.

In the above case, regarding the pulse width (pulse application time), in case of the detection of liquid type and the detection of concentration, since the fluid to be detected stays, avoiding overheating is preferred. For this reason, the pulse width is preferably less than 5 sec. On the other hand, in the case of the detection of flow rate, the fluid to be detected does not stay. Therefore, the flow rate can be detected when the pulse width (pulse application time) is not less than 1 sec.

The above liquid type detecting method for gasoline utilize natural convection and utilizes such a principle that the kinematic viscosity of gasoline has a correlation with the sensor output.

Further, regarding the liquid type detecting method for gasoline, in the distillation properties of gasoline shown in FIG. 18, distillation properties T30 to T70 have been found to provide a better correlation and thus are preferred.

Further, when the concentration of the fluid to be detected is measured, for example, in the case of an identification urea solution, as with the detection of the liquid type, the voltage output Vout can be obtained and correlated with the properties of urea.

The content of urea in the urea solution can be identified in an accurate and rapid (instantaneous) manner by comparing the voltage output Vout of the urea solution to be identified with data stored in a computer 72 based on previously measured calibration curve data for a urea solution as shown in FIG. 13.

Figure 23:
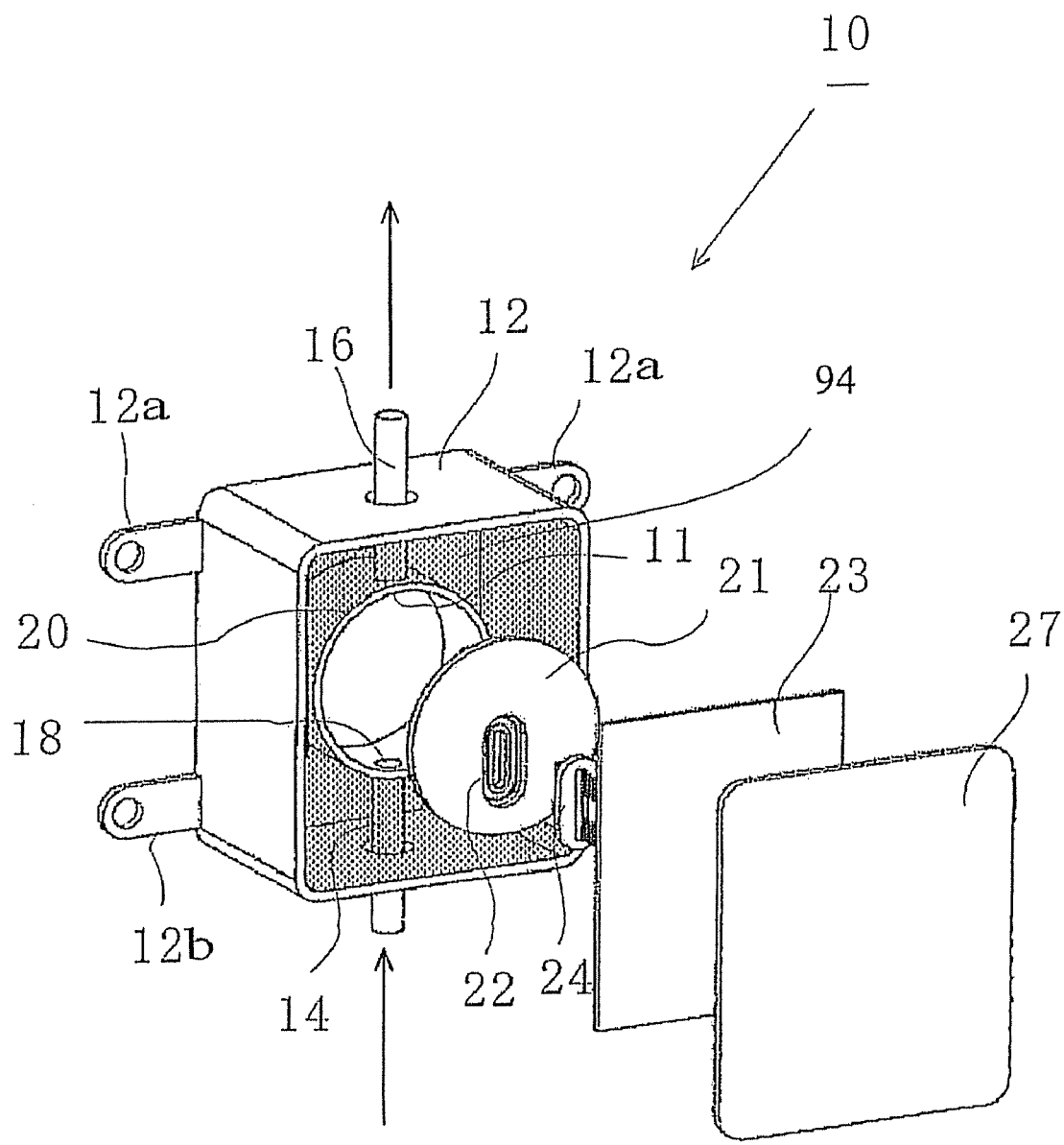
FIG. 23 is a perspective view showing another embodiment of a liquid type detectingapparatus according to the present invention.

FIG. 23 is a perspective view of another embodiment of the liquid type detecting apparatus according to the present invention.

The construction of the liquid type detecting apparatus 10 in this embodiment is basically the same as the construction of the liquid type detecting apparatus 10 in the embodiment shown in FIG. 20. Accordingly, in FIGS. 23 and 20, like parts are identified with the same reference numerals, and detailed explanation will be omitted.

In the liquid type detecting apparatus 10 in this embodiment, a heat insulating member 8 is interposed between the liquid type detecting apparatus body 12 and the liquid type detecting chamber 20.

Since a heat insulating member is interposed between the liquid type detecting apparatus body 12 and the liquid type detecting chamber 20, external temperature, external vibration, and external noise such as external electromagnetic waves do not affect the fluid to be detected within the liquid type detecting chamber 20 and the liquid type detecting sensor 24. Therefore, the liquid type and concentration of the fluid can be always detected with good accuracy.

For example, when the present invention is applied to the detection of automotive gasoline and light oils, the influence, on the detecting sensor, of the difference in temperature between winter and summer, the difference in temperature derived from direct sunlight, snow and the like, external noise such as electromagnetic waves, and, further, vibration during driving and impact caused, for example, by jumping of stone, can be prevented by this heat insulating member. Therefore, the liquid type and concentration of the fluid can be always detected with good accuracy.

The heat insulating member 8 is not particularly limited. For example, foamed synthetic resins such as polyethylene, polypropylene, and urethane, and glass wool are usable.

Figure 14:
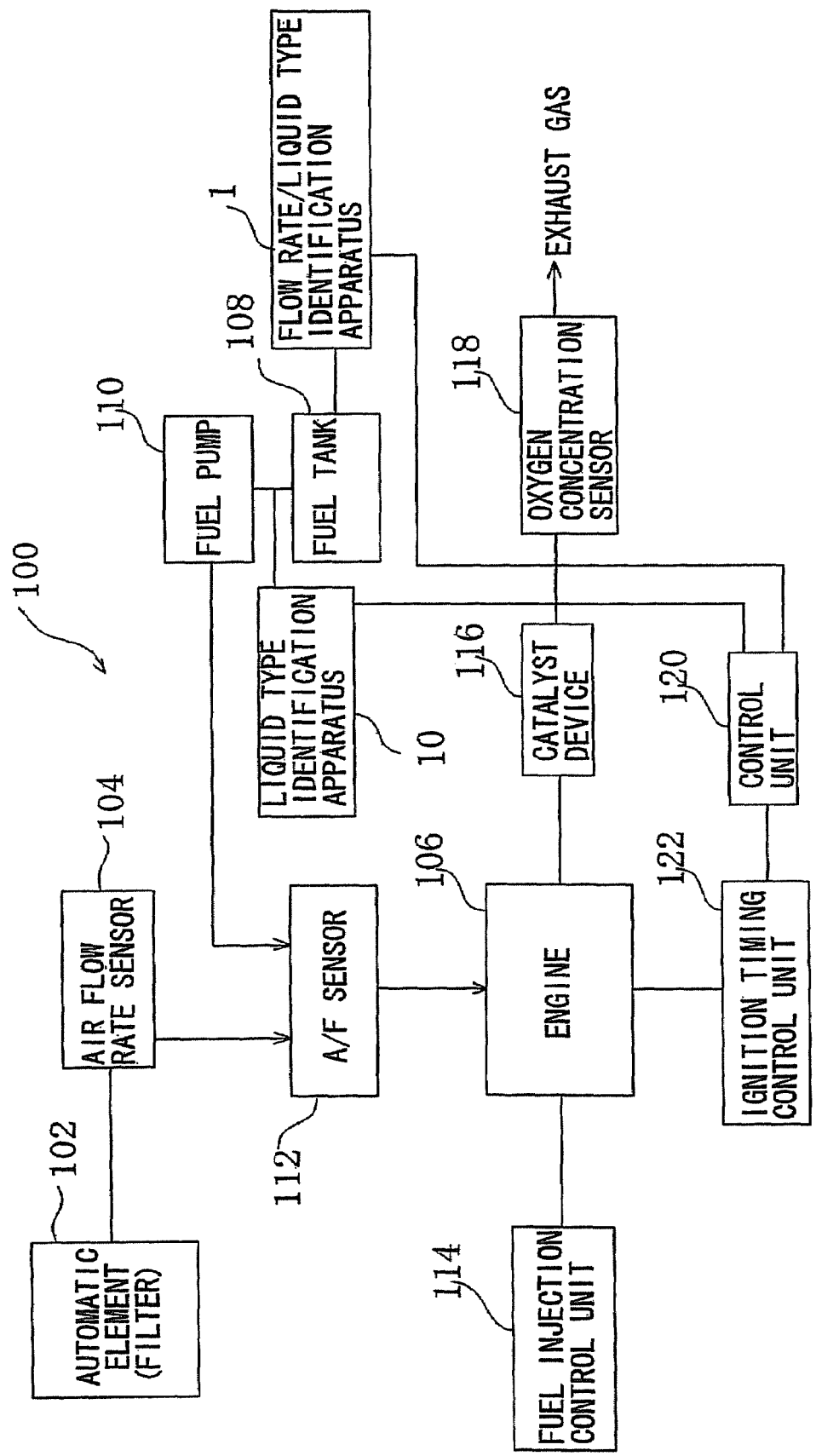
FIG. 14 is the same schematic diagram as FIG. 17, illustrating an embodiment in which aflow rate/liquid type detecting apparatus 1 having the above construction is applied to anautomotive system.
Figure 17:
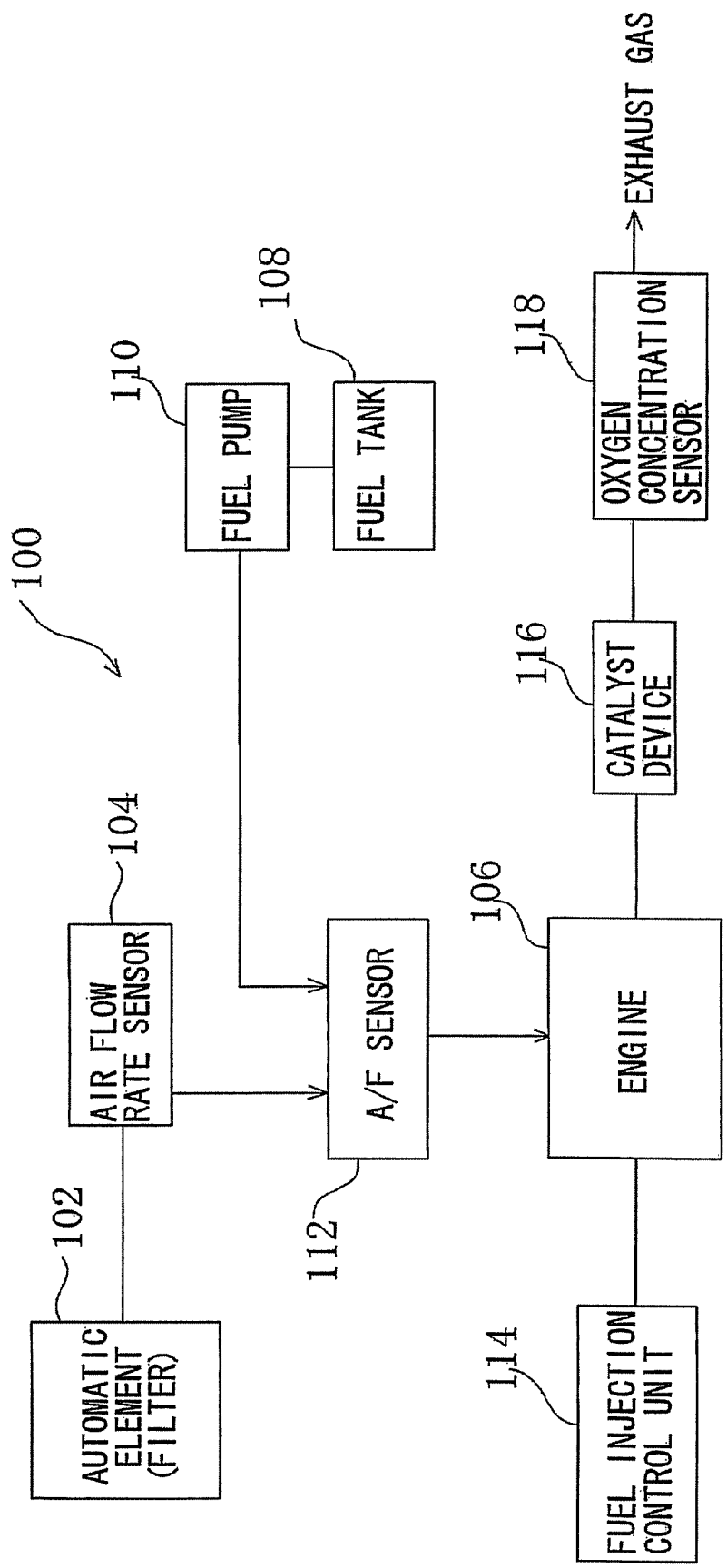
FIG. 17 is a schematic diagram of a conventional automotive system.

FIG. 14 is the same schematic diagram as FIG. 17, illustrating an embodiment in which a flow rate/liquid type detecting apparatus 1 having the above construction is applied to an automotive system.

The same component as those in FIG. 17 have the same reference numerals, and the detailed description thereof will be omitted.

In this automotive system 100, a flow rate/liquid type detecting apparatus 1 as shown in FIGS. 1 and 2 is provided within a fuel tank 108 or on the upstream side of a fuel pump 110.

In this automotive system 100, a liquid type detecting apparatus 10 as shown in FIGS. 20 and 21 is provided within a fuel tank 108 or on the upstream side of a fuel pump 110.

This automotive system 100 is constructed so that the liquid type and flow rate of the gasoline within the fuel tank 108 or on the upstream side or downstream side of the fuel pump 110 (in this embodiment, the case of the upstream side is shown for convenience of explanation) is detected by the flow rate/liquid type detecting apparatus 1. As a result, and ignition timing is adjusted by an ignition timing control unit 122 through the control of a control unit 120 depending upon the type of the gasoline.

This automotive system 100 is constructed so that the liquid type of the gasoline within the fuel tank 108 or on the upstream side or downstream side of the fuel pump 110 (in this embodiment, the case of the upstream side is shown for convenience of explanation) is detected by the liquid type detecting apparatus 10. As a result, ignition timing is adjusted by an ignition timing control unit 122 through the control of a control unit 120 depending upon the type of the gasoline.

Specifically, for example, when light (easy to evaporate) gasoline No. 7 has been detected, the ignition timing is controlled to earlier one, while, when heavy (difficult to evaporate) gasoline A2 has been detected, the ignition timing is controlled to delayed one.

Accordingly, in particular, even when an engine is started, particularly when an engine in which a catalyst device is not in a warmed state is started, the content of HCs in the exhaust gas can be reduced, and, at the same time, fuel consumption can be improved, without causing a reduction in torque.

Figure 15:
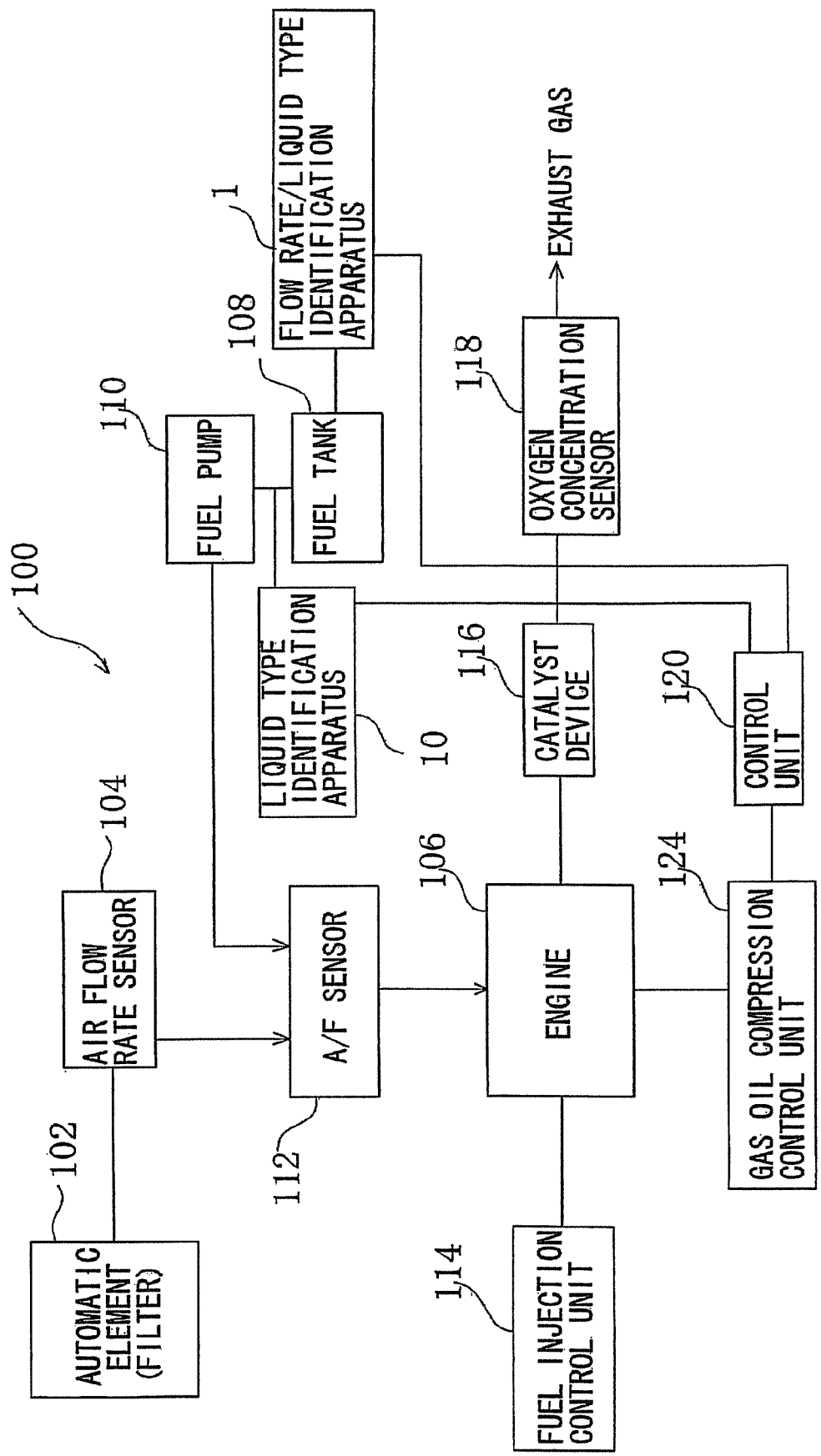
FIG. 15 is the same schematic diagram as FIG. 17, illustrating an embodiment in which aflow rate/liquid type detecting apparatus 1 having the above construction is applied to anautomotive system.

FIG. 15 is the same schematic diagram as FIG. 17, illustrating an embodiment in which a flow rate/liquid type detecting apparatus 1 having the above construction is applied to an automotive system.

The same component as those in FIG. 17 have the same reference numerals, and the detailed description thereof will be omitted.

In this automotive system 100, a flow rate/liquid type detecting apparatus 1 as shown in FIGS. 1 and 2 is provided within a fuel tank 108 or on the upstream side of a fuel pump 110.

In this automotive system 100, a liquid type detecting apparatus 10 as shown in FIGS. 20 and 21 is provided within a fuel tank 108 or on the upstream side of a fuel pump 110.

This automotive system 100 is constructed so that the liquid type and flow rate of the gasoline within the fuel tank 108 or on the upstream side or downstream side of the fuel pump 110 (in this embodiment, the case of the upstream side is shown for convenience of explanation) is detected by the flow rate/liquid type detecting apparatus 1. As a result, and the compression ratio of gasoline is regulated by a gasoline compression control unit 124 through the control of a control unit 120 depending upon the type of the gasoline.

This automotive system 100 is constructed so that the liquid type of the gasoline within the fuel tank 108 or on the upstream side or downstream side of the fuel pump 110 (in this embodiment, the case of the upstream side is shown for convenience of explanation) is detected by the liquid type detecting apparatus 10. As a result, and the compression ratio of gasoline is regulated by a gasoline compression control unit 124 through the control of a control unit 120 depending upon the type of the gasoline.

Specifically, for example, when light (easy to evaporate) gasoline No. 7 has been detected, the compression ratio is controlled to be lowered, while, when heavy (difficult to evaporate) gasoline A2 has been detected, the compression ratio is controlled to be enhanced.

Accordingly, in particular, even when an engine is started, particularly when an engine in which a catalyst device is not in a warmed state is started, the content of HCs in the exhaust gas can be reduced, and, at the same time, fuel consumption can be improved, without causing a reduction in torque.

Figure 16:
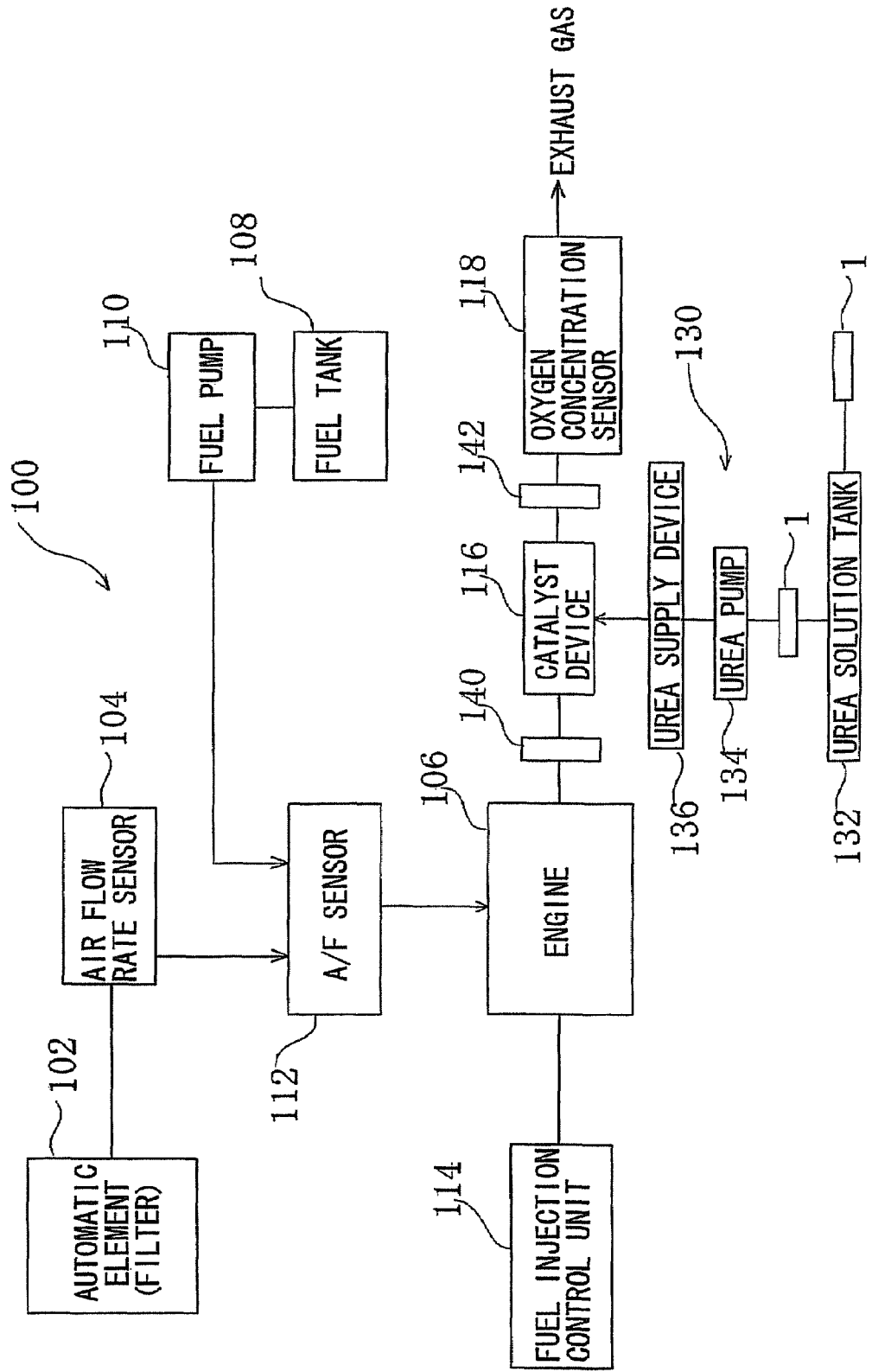
FIG. 16 is the same schematic diagram as FIG. 19, illustrating an embodiment in which aflow rate/liquid type detecting apparatus 1 having the above construction is applied to anautomotive system using a urea solution.
Figure 19:
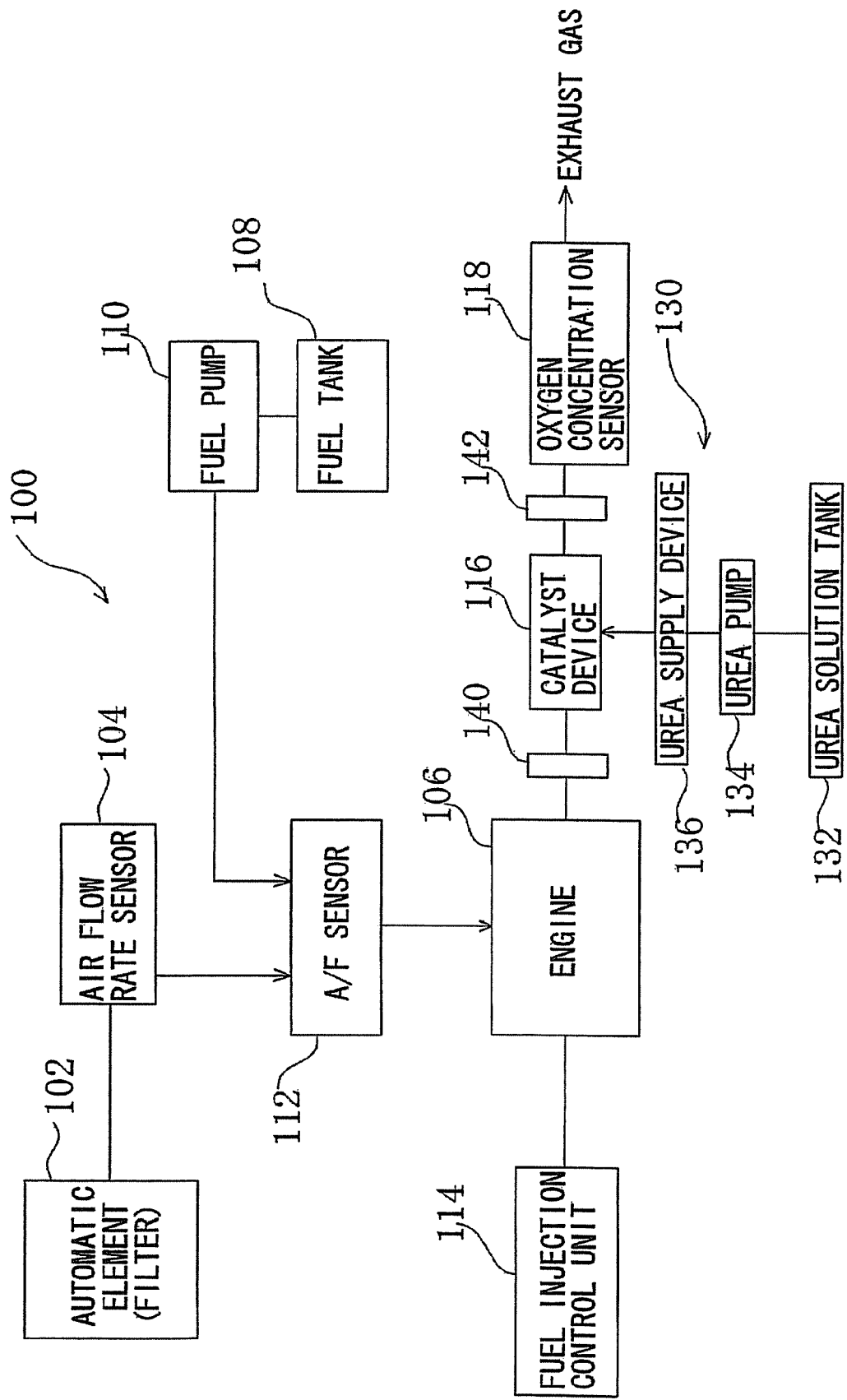
FIG. 19 is a schematic diagram of a conventional automotive system using a ureasolution.

FIG. 16 is the same schematic diagram as FIG. 19, illustrating an embodiment in which a flow rate/liquid type detecting apparatus 1 having the above construction is applied to an automotive system using a urea solution.

The same component as those in FIG. 19 have the same reference numerals, and the detailed description thereof will be omitted.

In this automotive system 100, a flow rate/liquid type detecting apparatus 1 as shown in FIGS. 1 and 2 is provided within a urea solution tank 132 or on the upstream side of a fuel pump 134.

The urea concentration of the urea solution within the urea solution tank 132 or on the upstream side or downstream side of the urea pump 134 (in this embodiment, the case of the upstream side is shown for convenience of explanation) is identified by the flow rate/liquid type detecting apparatus 1. As a result, the concentration of urea sprayed toward the upstream side of the catalyst device 116 is regulated so that, in order to efficiently cause a reduction reaction on the upstream side of the catalyst device 116 without causing solidification of the urea solution, for example, constantly, the urea solution comprises 32.5% of urea and 67.5% of $H_2O$.

Therefore, the urea concentration of the urea solution in the urea tank can be kept at a predetermined concentration, and, thus, the NOx in the exhaust gas can be decreased to a very low level by reduction.

In this automotive system 100, within the urea solution tank 132 or on the upstream side of the urea pump 134, a liquid type detecting device 10 as shown in FIGS. 20 and 21 may be provided instead of the flow rate/liquid type detecting apparatus 1 as shown in FIGS. 1 and 2.

Also in this case, the urea concentration of the urea solution within the urea solution tank 132 or on the upstream side or downstream side of the urea pump 134 (in this embodiment, the case of the upstream side is shown for convenience of explanation) is identified by the liquid type detecting apparatus 10. As a result, the concentration of urea sprayed toward the upstream side of the catalyst device 116 is regulated so that, in order to efficiently cause a reduction reaction on the upstream side of the catalyst device 116 without causing solidification of the urea solution, for example, constantly, the urea solution comprises 32.5% of urea and 67.5% of $H_2O$.

Therefore, the urea concentration of the urea solution in the urea tank can be kept at a predetermined concentration, and, thus, the NOx in the exhaust gas can be decreased to a very low level by reduction.

Preferred embodiments of the present invention have been described above. However, it should be noted that the present invention is not limited to these preferred embodiments, and, for example, pulse voltage P and number of times of sampling may be properly changed.

In the above embodiments, explanation has been made about gasoline and urea solutions in an automotive system. However, various variations and modifications may be made without departing from the object of the present invention. For example, the present invention can be applied to automotive system using light oils or kerosene, as well as to cases using fluids other than these fluids, for example, the case where, for example, in plants, the type, concentration, and flow rate of a fluid are detected in apparatuses where an organic solution of a substance dissolved in an organic solvent is allowed to flow.

According to the present invention, the type, concentration and flow rate of fluids, for example, gasoline or a light oil as a fuel in automobiles, and organic solutions in plants or the like can be detected.

The invention claimed is:

1. A flow rate/liquid type detecting apparatus for detecting at least one among the flow rate of a fluid, the type of the fluid, and the concentration of the fluid, comprising:
    a main passage through which a fluid to be detected flows;
    an auxiliary passage branched from said main passage;
    a flow rate/liquid type detecting sensor device provided in said auxiliary passage;
    an auxiliary passage control mechanism provided in said auxiliary passage, for controlling the flow of the fluid to be detected into said flow rate/liquid type detecting sensor device; and
    a control unit for controlling said flow rate/liquid detecting sensor device and said auxiliary passage control mechanism,
    said control unit being constructed so as to conduct control in such a manner that:
    in conducting any one of or both the detection of the type of said fluid to be detected and the detection of the concentration of said fluid to be detected, said auxiliary passage control mechanism is closed, and said fluid to be detected is allowed to temporarily stay within said flow rate/liquid type detecting sensor device to conduct any one of or both the detection of the liquid type and the detection of the concentration, and
    in detecting the flow rate of said fluid to be detected, said auxiliary passage control mechanism is opened to allow the fluid to be detected to flow into said flow rate/liquid detecting sensor device to detect the flow rate, and
    said flow rate/liquid type detecting sensor device comprises:
    a flow rate/liquid type detecting chamber for allowing the fluid to be detected which has been introduced into a flow rate/liquid type detecting sensor device body to temporarily stay therein,
    a flow rate/liquid type detecting sensor heater provided within said flow rate/liquid type detecting chamber, and
    said flow rate/liquid type detecting apparatus is constructed so that:
    in conducting any one of or both the detection of the type of said fluid to be detected and the detection of the concentration of said fluid to be detected,
    a pulse voltage is applied to said flow rate/liquid type detecting sensor heater for a predetermined period of time,
    the fluid to be detected which temporarily stays within said flow rate/liquid type detecting chamber is heated with said flow rate/liquid type detecting sensor heater, and
    any one of or both the liquid type of the fluid and the concentration of the fluid are detected, by a voltage output difference V0, corresponding to a difference in temperature between the initial temperature and the peak temperature of said flow rate/liquid type detecting liquid temperature sensor,
    in detecting the flow rate of said fluid to be detected,
    a pulse voltage is applied to said flow rate/liquid type detecting sensor heater for a predetermined period of time,
    the fluid to be detected which flows through said flow rate/liquid type detecting chamber is heated with said flow rate/liquid type detecting sensor heater, and
    the flow rate is detected, by a voltage output difference V0, corresponding to a difference in temperature between the initial temperature and the peak temperature of said flow rate/liquid type detecting sensor heater.

2. The flow rate/liquid type detecting apparatus according to claim 1, characterized in that a non-return valve is provided on the downstream side of said flow rate/liquid type detecting sensor device in said auxiliary passage.

3. The flow rate/liquid type detecting apparatus according to claim 1, characterized in that a main passage control mechanism for controlling the flow of said fluid to be detected into said main passage is provided in said main passage.

4. The flow rate/liquid type detecting apparatus according to claim 3, characterized in that said control unit is constructed so as to conduct control in such a manner that:
    when the flow rate of said fluid to be detected is small, said main passage control mechanism is closed, and
    when the flow rate of said fluid to be detected is large, said main passage control mechanism is opened.

5. The flow rate/liquid type detecting apparatus according to claim 1, characterized in that an orifice is provided in the main passage.

6. The flow rate/liquid type detecting apparatus according to claim 1, characterized in that the voltage output difference V0 is the difference in voltage between an average initial voltage V1, which is determined by sampling the initial voltage before the application of said pulse voltage by a predetermined number of times, and an average peak voltage V2, which is determined by sampling the peak voltage after the application of said pulse voltage by a predetermined number of times, that is, $$V0 = V2 - V1.$$

7. The flow rate/liquid type detecting apparatus according to claim 1, characterized in that said control unit is constructed so that:

based on calibration curve data as a correlation between temperature and voltage output difference, for predetermined reference fluids previously stored in said control unit, any one of or both the liquid type and concentration of said fluid to be detected are detected using said voltage output difference V0 obtained for said fluid to be detected.

8. The flow rate/liquid type detecting apparatus according to claim 1, characterized in that said control unit is constructed so that:

a voltage output Vout for the voltage output difference V0 at a measuring temperature for said fluid to be detected is corrected in a correlation with the output voltage for the voltage output difference at the measuring temperature for a predetermined threshold reference fluid.

9. The flow rate/liquid type detecting apparatus according to claim 1, characterized in that said control unit is constructed so that:

based on calibration curve data as a correlation between temperature and voltage output difference, for predetermined reference fluids previously stored in said control unit, the flow rate of said fluid to be detected is detected using said voltage output difference V0 obtained for said fluid to be detected.

10. The flow rate/liquid type detecting apparatus according to claim 1, characterized in that said flow rate/liquid type detecting sensor heater is constructed so as to come into contact with the fluid to be detected through said metallic fin.

11. A flow rate/liquid type detecting apparatus for an automobile, for detecting the flow rate and type of gasoline or a light oil, characterized in that:

the flow rate/liquid type detecting apparatuses according to claim 1 is provided within a fuel tank or on the upstream side or downstream side of a fuel pump.

12. An automotive exhaust gas reduction apparatus comprising:

the flow rate/liquid type detecting apparatus according to claim 1, which is provided within a fuel tank or on the upstream side or downstream side of a fuel pump; and an ignition timing control unit for regulating ignition timing based on the flow rate and type of the gasoline or light oil, which is detected by said flow rate/liquid type detecting apparatus.

13. An automotive exhaust gas reduction apparatus, comprising:

the flow rate/liquid type detecting apparatus according to claim 1, which is provided within a fuel tank or on the upstream side or downstream side of a fuel pump; and a gasoline or light oil compression control unit for regulating the compression ratio of the gasoline or light oil based on the flow rate and type of the gasoline or light oil, which is detected by said flow rate/liquid type detecting apparatus.

14. An automotive exhaust gas reduction apparatus, comprising:

a urea solution feed mechanism for feeding a urea solution to the upstream side of a catalyst device, said urea solution feed mechanism comprising a urea solution tank for storing a urea solution, a urea pump, a urea spray device for spraying the urea solution, which is supplied from said urea pump, toward the upstream side of said catalyst device, and the flow rate/liquid type detecting apparatus according to claim 1, which is provided within a urea tank or on the upstream side or downstream side of said urea pump.

15. A flow rate/liquid type detecting method for detecting at least one among the flow rate of a fluid, the type of the fluid, and the concentration of the fluid, characterized in that:

providing a flow rate/liquid type detecting apparatus comprising, a main passage through which a fluid to be detected flows, an auxiliary passage branched from said main passage, and a flow rate/liquid type detecting sensor device comprising a flow rate/liquid type detecting chamber for allowing the fluid to be detected which has been introduced into a flow rate/liquid type detecting sensor device body to temporarily stay therein, an auxiliary passage control mechanism provided in said auxiliary passage, for controlling the flow of the fluid to be detected into said flow rate/liquid type detecting sensor device, and a flow rate/liquid type detecting sensor heater provided within said flow rate/liquid type detecting chamber;

detecting the type of said fluid to be detected, closing said auxiliary passage control mechanism if opened, and said fluid to be detected is allowed to temporarily stay within said flow rate/liquid type detecting sensor device, detecting the concentration of said fluid to be detected and said fluid to be detected is allowed to temporarily stay within said flow rate/liquid type detecting sensor device, applying a pulse voltage to said flow rate/liquid type detecting sensor heater for a predetermined period of time, heating with the heater, the fluid to be detected which temporarily stays within said flow rate/liquid type detecting chamber, detecting any one of or both the liquid type of the fluid, the concentration of the fluid, by a voltage output difference V0, corresponding to a difference in temperature between the initial temperature and the peak temperature of said flow rate/liquid type detecting sensor heater, detecting the flow rate of the fluid to be detected, opening said auxiliary passage control mechanism if closed to allow the fluid to be detected to flow into said flow rate/liquid detecting sensor device.

16. The flow rate/liquid type detecting method according to claim 15, further comprising the steps of providing a non-return valve on the downstream side of said flow rate/liquid type detecting sensor device in said auxiliary passage.

17. The flow rate/liquid type detecting method according to claim 15, wherein said flow rate/liquid type detecting apparatus further comprises a main passage control mechanism for controlling the flow of said fluid to be detected into said main passage.

18. The flow rate/liquid type detecting method according to claim 17, further comprising the steps of:

closing said main passage control mechanism when the flow rate of said fluid to be detected is small is closed, and opening said main passage control mechanism when the flow rate of said fluid to be detected is large is opened.

19. The flow rate/liquid type detecting method according to claim 15, further comprising providing an orifice in the main passage.

20. The flow rate/liquid type detecting method according to claim 15, further comprising the voltage output difference V0 is the difference in voltage between an average initial voltage V1, which is determined by sampling the initial voltage before the application of said pulse voltage by a predetermined number of times, and an average peak voltage V2, which is determined by sampling the peak voltage after the application of said pulse voltage by a predetermined number of times, that is, $$V0=V2-V1.$$

21. The flow rate/liquid type detecting method according to claim 15,
    wherein detecting any one of or both the liquid type or concentration of said fluid to be detected further comprises using said voltage output difference V0 obtained for said fluid to be detected based on calibration curve data as a correlation between temperature and voltage output difference for predetermined reference fluids previously stored in said control unit.

22. The flow rate/liquid type detecting method according to claim 15, further comprises the steps of correcting
    a voltage output Vout for the voltage output difference V0 at a measuring temperature for said fluid to be detected in a correlation with the output voltage for the voltage output difference at the measuring temperature for a predetermined threshold reference fluid.

23. The flow rate/liquid type detecting method according to claim 15, wherein
    detecting the flow rate of said fluid to be detected further comprises using said voltage output difference V0 obtained for said fluid to be detected based on previously stored calibration curve data as a correlation between temperature and voltage output difference for predetermined reference fluids.

24. The flow rate/liquid type detecting method according to claim 15, wherein said flow rate/liquid type detecting sensor heater comprises a laminated flow rate/liquid type detecting sensor heater in which a heater and a flow rate/liquid type detecting liquid temperature sensor are laminated through an insulating layer.

25. The flow rate/liquid type detecting method according to claim 15, further comprising constructing the heater in said flow rate/liquid type detecting sensor heater and said flow rate/liquid type detecting liquid temperature sensor each so as to come into contact with the fluid to be detected through a metallic fin.

26. The flow rate/liquid type detecting method according to claim 15, further comprising constructing said liquid temperature sensor so as to come into contact with the fluid to be detected through said metallic fin.

27. The flow rate/liquid type detecting method according to claim 15, further comprising:
    detecting the flow rate and type of said gasoline or light oil within a fuel tank or detecting the flow rate and type of said gasoline or light oil on the upstream side or downstream side of a fuel pump.

28. A flow rate/liquid type detecting method for an automobile, for detecting the flow rate and type of gasoline or a light oil, the flow rate/liquid type detecting method according to claim 15, further comprising:
    detecting the flow rate and type of said gasoline or light oil within a fuel tank or detecting the flow rate and type of said gasoline or light oil on the upstream side or downstream side of a fuel pump,
    regulating an ignition timing based on the flow rate and type of the gasoline or light oil which is detected by said flow rate/liquid type detecting apparatus.

29. A flow rate/liquid type detecting method for an automobile, for detecting the flow rate and type of gasoline or a light oil, the flow rate/liquid type detecting method according to claim 15, further comprising:
    detecting the flow rate and type of said gasoline or light oil within a fuel tank or detecting the flow rate and type of said gasoline or light oil on the upstream side or downstream side of a fuel pump, and
    regulating the compression ratio of the gasoline based on the flow rate and type of the gasoline or light oil which is detected by said flow rate/liquid type detecting apparatus.

30. The flow rate/liquid type detection method of claim 15, comprising the steps of:
    supplying a urea solution to the upstream side of the catalyst device, through a urea solution feed mechanism comprising a urea solution tank for storing a urea solution, a urea pump, and a urea spray device for spraying the urea solution, which is supplied from said urea pump, toward the upstream side of said catalyst device, and
    detecting the flow rate and urea concentration of the urea solution within said urea tank or on the upstream side or downstream side of said urea pump.

31. A liquid type detecting apparatus for detecting any one of or both the liquid type and concentration of a fluid, comprising:
    a liquid type detecting chamber for allowing a fluid to be detected which has been introduced into a liquid type detecting apparatus body to temporarily stay therein,
    a liquid type detecting sensor disposed within said liquid type detecting chamber, and
    a flow control plate provided within said liquid type detecting chamber so as to surround said liquid type detecting sensor;
    said liquid type detecting sensor comprises:
    a liquid type detecting sensor heater provided within said liquid type detecting chamber, and
    in conducting any one of or both the detection of the type of said fluid to be detected and the detection of the concentration of said fluid to be detected,
    a pulse voltage is applied to said liquid type detecting sensor heater for a predetermined period of time to heat,
    the fluid to be detected which temporarily stays within said liquid type detecting chamber is heated with said liquid type detecting sensor heater, and
    any one of or both the liquid type of the fluid and the concentration of the fluid are detected, by a voltage output difference V0, corresponding to a difference in temperature between the initial temperature and the peak temperature of said liquid type detecting liquid temperature sensor.

32. The liquid type detecting apparatus according to claim 31, characterized in that said flow control plate has a fluid inflow port confronted with a fluid introduction port in said liquid type detecting chamber and a fluid outflow port confronted with a fluid discharge port in said liquid type detecting chamber.

33. The liquid type detecting apparatus according to claim 31, characterized in that the fluid introduction port in said liquid type detecting chamber and the fluid inflow port in said flow control plate are spaced from each other by a predetermined distance, and
    the fluid discharge port in said liquid type detecting chamber and the fluid outflow port in said flow control plate are spaced from each other by a predetermined distance.

34. The liquid type detecting apparatus according to claim 31, characterized in that the side wall in the vicinity of the fluid discharge port in said liquid type detecting chamber is provided in an approximately arc form.

35. The liquid type detecting apparatus according to claim 31, characterized in that said liquid type detecting chamber is provided with an approximately circular tube side wall, and the fluid introduction port and the fluid discharge port in said liquid type detecting chamber are provided so as to confront said side wall.

36. The liquid type detecting apparatus according to claim 31, characterized in that a heat insulating member is interposed between said liquid type detecting apparatus body and said liquid type detecting chamber.

37. The liquid type detecting apparatus according to claim 36, characterized in that:
a voltage output Vout for the voltage output difference V0 at a measuring temperature for said fluid to be detected is corrected in a correlation with the output voltage for the voltage output difference at the measuring temperature for a predetermined threshold reference fluid.

38. The liquid type detecting apparatus according to claim 36, characterized in that said flow rate/liquid type detecting sensor heater is constructed so as to come into contact with the fluid to be detected through said metallic fin.

39. The liquid type detecting apparatus according to claim 31, characterized in that the voltage output difference V0 is the difference in voltage between an average initial voltage V1 determined by sampling the initial voltage before the application of said pulse voltage by a predetermined number of times and an average peak voltage V2 determined by sampling the peak voltage after the application of said pulse voltage by a predetermined number of times, that is, $$V0 = V2 - V1.$$

40. The liquid type detecting apparatus according to claim 31, characterized in that any one of or both the liquid type and concentration of said fluid to be detected are detected using said voltage output difference V0 obtained for said fluid to be detected,
based on previously stored calibration curve data as a correlation between temperature and voltage output difference for predetermined reference fluids.

41. A liquid type detecting apparatus for an automobile, for detecting the type of gasoline or a light oil, comprising:
the liquid type detecting apparatus according claim 31, which is provided within a fuel tank or on the upstream side or downstream side of a fuel pump.

42. An automotive exhaust gas reduction apparatus, comprising:
the liquid type detecting apparatus according to claim 31, which is provided within a fuel tank or on the upstream side or downstream side of a fuel pump; and
an ignition timing control unit for regulating ignition timing based on the type of the gasoline or light oil, which is detected by said liquid type detecting apparatus.

43. An automotive exhaust gas reduction apparatus, comprising:
the liquid type detecting apparatus according to claim 31, which is provided within a fuel tank or on the upstream side or downstream side of a fuel pump; and
a gasoline or light oil compression control unit for regulating the compression ratio of the gasoline or light oil based on the type of the gasoline or light oil which is detected by said liquid type detecting apparatus.

44. An automotive exhaust gas reduction apparatus, comprising:
a urea solution feed mechanism for feeding a urea solution to the upstream side of a catalyst device,
said urea solution feed mechanism comprising a urea solution tank for storing a urea solution, a urea pump, a urea spray device for spraying the urea solution, which is supplied from said urea pump, toward the upstream side of said catalyst device, and
the liquid type detecting apparatus according to claim 31, which is provided within said urea tank or on the upstream side or downstream side of said urea pump.

45. A liquid type detecting method for detecting any one of or both the liquid type and concentration of a fluid, comprising the steps of:
providing a liquid type detecting apparatus comprising:
a liquid type detecting chamber for allowing a fluid to be detected which has been introduced into a liquid type detecting apparatus body to temporarily stay therein,
a liquid type detecting sensor disposed within said liquid type detecting chamber, said liquid type detecting sensor including a liquid type detecting sensor heater and
a flow control plate provided within said liquid type detecting chamber so as to surround said liquid type detecting sensor;
applying a pulse voltage to said liquid type detecting sensor heater for a predetermined period of time to heat;
heating the fluid to be detected which temporarily stays within said liquid type detecting chamber with said liquid type detecting sensor heater and
any one of or both the liquid type of the fluid and/or the concentration of the fluid detecting by a voltage output difference V0, corresponding to a difference in temperature between the initial temperature and the peak temperature of said liquid type detecting liquid temperature sensor.

46. The liquid type detecting method according to claim 45, wherein said flow control plate includes a fluid inflow port confronted with a fluid introduction port in said liquid type detecting chamber and a fluid outflow port confronted with a fluid discharge port in said liquid type detecting chamber.

47. The liquid type detecting method according to claim 46, wherein the fluid introduction port in said liquid type detecting chamber and the fluid inflow port in said flow control plate are spaced from each other by a predetermined distance, and
the fluid discharge port in said liquid type detecting chamber and the fluid outflow port in said flow control plate are spaced from each other by a predetermined distance.

48. The liquid type detecting method according to claim 46, further comprises providing a side wall in the vicinity of the fluid discharge port in said liquid type detecting chamber is provided in an approximately arc form.

49. The liquid type detecting apparatus according to claim 48, wherein said liquid type detecting chamber further includes an approximately circular tube side wall, and the fluid introduction port and the fluid discharge port in said liquid type detecting chamber are provided so as to confront said side wall.

50. The liquid type detecting method according to claim 45, further comprising the steps of providing a heat insulating member interposed between said liquid type detecting apparatus and said liquid type detecting chamber.

51. The liquid type detecting method according to claim 45, further comprises the voltage output difference V0 is the difference in voltage between an average initial voltage V1 determined by sampling the initial voltage before the application of said pulse voltage by a predetermined number of times and an average peak voltage V2 determined by sampling the peak voltage after the application of said pulse voltage by a predetermined number of times, that is, $$V0 = V2 - V1.$$

52. The liquid type detecting method according to claim 45, wherein detecting any one of or both the liquid type and/or concentration of said fluid to be detected further comprises using said voltage output difference V0 obtained for said fluid to be detected based on previously stored calibration curve data as a correlation between temperature and voltage output difference for predetermined reference fluids.

53. The liquid type detecting method according to claim 45, further comprising the steps of correcting a voltage output Vout for the voltage output difference V0 at a measuring temperature for said fluid to be detected in a correlation with the output voltage for the voltage output difference at the measuring temperature for a predetermined threshold reference fluid.

54. The liquid type detecting method according to claim 45, further comprises constructing said flow rate/liquid type detecting sensor heater so as to come into contact with the fluid to be detected through said metallic fin.

55. The liquid type detecting method according to claim 45, further comprising detecting the type of said gasoline or light oil within a fuel tank or detecting the type of said gasoline or light oil on the upstream side or downstream side of a fuel pump.

56. A liquid type detecting method for an automobile, for detecting the type of gasoline or a light oil, the liquid type detecting method according to claim 45, further comprising:

detecting the type of said gasoline or light oil within a fuel tank or detecting the type of said gasoline or light oil on the upstream side or downstream side of a fuel pump, regulating an ignition timing based on the type of the gasoline or light oil which is detected by said liquid type detecting apparatus.

57. A liquid type detecting method for an automobile, for detecting the type of gasoline or a light oil the liquid type detecting method according to claim 45, further comprising:

detecting the type of said gasoline or light oil within a fuel tank or detecting the type of said gasoline or light oil on the upstream side or downstream side of a fuel pump, regulating the compression ratio of the gasoline based on the type of the gasoline or light oil which is detected by said liquid type detecting apparatus.

58. The liquid type detecting method according to claim 45, further comprising:

supplying a urea solution to the upstream side of the catalyst device, through a urea solution feed mechanism comprising a urea solution tank for storing a urea solution, a urea pump, and a urea spray device for spraying the urea solution, which is supplied from said urea pump, toward the upstream side of said catalyst device, and detecting the urea concentration of the urea solution within said urea tank or on the upstream side or downstream side of said urea pump.

* * * * *

UNITED STATES PATENT AND TRADEMARK OFFICE
CERTIFICATE OF CORRECTION

PATENT NO. : 7,647,844 B2
APPLICATION NO. : 11/956650
DATED : January 19, 2010
INVENTOR(S) : Kawanishi et al.

It is certified that error appears in the above-identified patent and that said Letters Patent is hereby corrected as shown below:

Columns 20, 21 and 22, Under "BRIEF DESCRIPTION OF THE DRAWINGS", please replace the existing "BRIEF DESCRIPTION OF THE DRAWINGS" with the following:

--BRIEF DESCRITION OF THE DRAWINGS
Fig. 1 is a schematic diagram showing an embodiment of a flow rate/liquid type detecting apparatus according to the present invention;
Fig. 2 is a schematic top view showing an embodiment of a flow rate/liquid type detecting sensor device in a flow rate/liquid type detecting apparatus according to the present invention;
Fig. 3 is a cross-sectional view taken along line A-A of Fig. 2;
Fig. 4 is a partially enlarged cross-sectional view showing the mounted state of the flow rate/liquid type detecting sensor shown in Fig. 3;
Fig. 5 is a cross-sectional view of a flow rate/liquid type detecting sensor;
Fig. 6 is a partially enlarged exploded perspective view showing the state of stacking of a thin-film chip part in a flow rate/liquid type detecting sensor;
Fig. 7 is a schematic circuit block diagram of an embodiment of a flow rate/liquid type detecting sensor device in a flow rate/liquid type detecting apparatus according to the present invention;
Fig. 8 is a graph showing a time vs. voltage relationship illustrating a liquid type detecting method using a flow rate/liquid type detecting apparatus according to the present invention;
Fig. 9 is a graph showing calibration curve illustrating a liquid type detecting method using a flow rate/liquid type detecting apparatus according to the present invention;
Fig. 10 is a graph illustrating an output correction method in a liquid type detecting method using a flow rate/liquid type detecting apparatus according to the present invention;
Fig. 11 is a graph showing a calibration curve illustrating a flow rate detecting method using a flow rate/liquid type detecting apparatus according to the present invention;

Signed and Sealed this

Twenty-second Day of June, 2010

David J. Kappos
*Director of the United States Patent and Trademark Office*

Fig. 12 is a schematic diagram of the whole measuring apparatus used for obtaining calibration curve data shown in Fig. 11;

Fig. 13 is a graph showing a calibration curve illustrating a concentration detecting method using a flow rate/liquid type detecting apparatus according to the present invention;

Fig. 14 is the same schematic diagram as Fig. 17, illustrating an embodiment in which a flow rate/liquid type detecting apparatus 1 having the above construction is applied to an automotive system;

Fig. 15 is the same schematic diagram as Fig. 17, illustrating an embodiment in which a flow rate/liquid type detecting apparatus 1 having the above construction is applied to an automotive system;

Fig. 16 is the same schematic diagram as Fig. 19, illustrating an embodiment in which a flow rate/liquid type detecting apparatus 1 having the above construction is applied to an automotive system using a urea solution;

Fig. 17 is a schematic diagram of a conventional automotive system;

Fig. 18 is a graph showing distillation properties of gasoline;

Fig. 19 is a schematic diagram of a conventional automotive system using a urea solution;

Fig. 20 is an exploded perspective view of the whole liquid type detecting apparatus according to the present invention;

Fig. 21 is an exploded perspective view of a liquid type detecting chamber in a liquid type detecting apparatus according to the present invention;

Fig. 22 is a schematic diagram illustrating the state of detection of a liquid type detecting apparatus according to the present invention;

Fig. 23 is a perspective view showing another embodiment of a liquid type detecting apparatus according to the present invention; and Fig. 24 is a schematic circuit block diagram of another embodiment of a flow rate/liquid type detecting sensor device in a flow rate/liquid type detecting apparatus according to the present invention.--